US012735445B2

(12) United States Patent
Birkus et al.

(10) Patent No.: US 12,735,445 B2
(45) Date of Patent: Sep. 15, 2026

(54) 3'3' CYCLIC DINUCLEOTIDES CONTAINING ISONUCLEOTIDIC UNITS

(71) Applicant: INSTITUTE OF ORGANIC CHEMISTRY AND BIOCHEMISTRY AS CR, V. V. I., Prague (CZ)

(72) Inventors: Gabriel Birkus, South Lake Tahoe, CA (US); Milan Dejmek, Prague (CZ); Radim Nencka, Roztoky (CZ); Michal Sala, Kladno (CZ)

(73) Assignee: INSTITUTE OF ORGANIC CHEMISTRY AND BIOCHEMISTRY AS CR, V. V. I., Prague (CZ)

( * ) Notice: Subject to any disclaimer, the term of this patent is extended or adjusted under 35 U.S.C. 154(b) by 499 days.

(21) Appl. No.: 18/280,527

(22) PCT Filed: Mar. 1, 2022

(86) PCT No.: PCT/CZ2022/050023
§ 371 (c)(1),
(2) Date: Sep. 6, 2023

(87) PCT Pub. No.: WO2022/188903
PCT Pub. Date: Sep. 15, 2022

(65) Prior Publication Data

US 2024/0166681 A1 May 23, 2024

(30) Foreign Application Priority Data

Mar. 11, 2021 (EP) .................................... 21162177

(51) Int. Cl.
*C07H 21/00* (2006.01)
*A61K 39/39* (2006.01)
*A61K 39/00* (2006.01)

(52) U.S. Cl.
CPC ............. *C07H 21/00* (2013.01); *A61K 39/39* (2013.01); *A61K 2039/55561* (2013.01)

(58) Field of Classification Search
USPC ........................................................... 514/47
See application file for complete search history.

(56) References Cited

FOREIGN PATENT DOCUMENTS

WO WO-2019193543 A1 * 10/2019 ............. C07H 21/04

OTHER PUBLICATIONS

International Search Report and Written Opinion for PCT Application No. PCT/CZ2022/050023, mailed Jul. 7, 2022.
International Application Status Report generated Aug. 30, 2023.

* cited by examiner

*Primary Examiner* — Traviss C Mcintosh, III
(74) *Attorney, Agent, or Firm* — Notaro, Michalos & Zaccaria P.C.

(57) ABSTRACT

The present disclosure relates to 3'3' cyclic dinucleotides containing isonucleotidic units, their pharmaceutically acceptable salts, their pharmaceutical composition and combinations of substances and other medicaments or pharmaceuticals. The disclosure also relates to the compounds for the treatment or prevention of diseases or conditions modifiable by STING protein modulation, such as cancer or viral, allergic and inflammatory diseases. In addition, these substances can be used as adjuvants in vaccines.

17 Claims, No Drawings

Specification includes a Sequence Listing.

3'3' CYCLIC DINUCLEOTIDES CONTAINING ISONUCLEOTIDIC UNITS

FIELD OF INVENTION

The present disclosure relates to 3'3' cyclic dinucleotides and derivatives thereof that are useful in the treatments of diseases in which modulation of STING adaptor protein (Stimulator of Interferon Genes) is beneficial, for example, inflammation, allergic and autoimmune diseases, cancer, and diseases caused by viruses such as hepatitis B virus, human immunodeficiency virus, coronaviruses (e.g. SARS-CoV-2) and flaviviruses, and in the preparation of immunogenic compositions or vaccine adjuvants.

BACKGROUND ART

The innate immune system recognizes the presence of pathogen or disruption of the homeostasis of the host by a battery of Pattern Recognition Receptors (PRRs) which detect a small set of ligands associated with pathogens or damage. These ligands are generally called Pathogen or Damage Associated Molecular Patterns (PAMPs and DAMPs) (Takeuchi O et al, *Cell,* 2010:140, 805). A number of PRRs have been identified over the past two decades including Toll-like receptors, retinoic acids inducible gene (RIG-I)-like receptors, nucleotide-binding oligomerization domain-like (NOD) receptors, C-type lectin receptors and cytosolic DNA sensors. Recognition of PAMPs and DAMPs by PRRs ultimately leads to the upregulation of cytokines and chemokines, including interferons, and recruitment of immune cells to the sites of infection. All these processes slow down pathogen replication and contribute to the development of adaptive immunity.

Cellular DNA is normally restricted to the nucleus and mitochondria of healthy cells. DNA present in cytosol, therefore, represents a signal indicating the presence of pathogen or disruption of the host homeostasis. The sensing of exogenous DNA is initiated by several DNA sensors such as DNA-dependent activator of IRFs (DAI) or DEAD box polypeptide 41 (DDX41). They signal via adaptor protein STING (Stimulator Of Interferon Genes, also called TMEM173, MITA, ERIS) (Unterholzner L, *Immunology,* 2013: 218, 1312) by recruiting protein kinase TBK1 that triggers activation of the transcription factors NFκ-B (nuclear factor kappa B) and IRF-3 (interferon regulatory factor 3). Activation of STING ultimately results in release of type I and III interferons and variety of cytokines and chemokines such as IL-6, TNF-α and INF-γ.

Alternatively, STING can be activated by the second messenger cyclic dinucleotides (CDNs)(Burdette et al. Nature 2011: 478,515). CDNs with affinity to STING contain two purine nucleotide monophosphates linked with either two 3'-5' (3'3'-CDNs), two 2'-5' (2'2'-CDNs) or 2'-5' and 3'-5' phosphodiester bonds (2'3'-CDNs). The prototype 2'3' cGAMP (c[G(2',5')pA(3',5')p]) is a product of the activation of host cGAS in the presence of pathogen or self dsDNA and it has the highest binding affinity to STING of all linkage isomers (Zhang et al, Molecular Cell 2013:51, 226).

The type I interferons (IFNs) are immune-regulatory cytokines that play a pivotal role in viral immunity. They induce dendritic cell (DC) and macrophage maturation and activation (Galluci et al, Nat Med, 1999:5, 1249) and promote T- and B-cell survival, activation and differentiation. Furthermore, they activate numerous intracellular pathways that inhibit virus replication. The clinical utility of type I interferons has been demonstrated by their usefulness in treatment of chronic hepatitis B and C (Lin and Young, *Cytokine Growth Factor Rev,* 2014:25,369).

In addition, interferons have shown utility in treatment of human cancers (Cohen et al, *N Engl J Med,* 2005:353, 2477, Tsao et al, *N Engl J Med,* 2004:351, 998). They can directly inhibit proliferation of tumor cells and may be synergistic with many approved anticancer agents. Furthermore, type-I-IFNs can act on immune cells to induce antitumor response (Musella et al, Oncoimmunology 2017:6, e1314424). Type I IFN signaling was shown to be important in tumor-initiated T cell priming in mice and animals lacking the IFN-α/β receptor in dendritic cells were unable to reject immunogenic tumors, and were defective in antigen cross-presentation to CD8+ T cells (Fuertes et al, *J Exp Med,* 2011:208, 2005, Diamond et al, *J Exp Med,* 2011:208, 1989). Consistently with these observations, intratumoral injection of STING agonists has been recently shown to induce regression of established tumors in mice and generated substantial systemic immune responses capable of rejecting distant metastases and providing long-lived immunologic memory (Corrales et al, Cell Rep, 2015:11, 1018).

CDNs are believed to promote priming of both cellular and humoral immunity. For example, CDNs were shown to be an effective adjuvant in animal models (Dubensky et al, Ther Adv Vaccines, 2013:1, 131).

There continues to be a need for novel CDNs that activate STING.

DESCRIPTION OF THE INVENTION

In an aspect, this disclosure describes novel 3'3' cyclic di-nucleotides and derivatives thereof that bind to and activate protein STING and, consequently, stimulate the signal transduction pathway that induces interferons and other cytokines/chemokines. One advantage compared to previously disclosed CDNs arises from the replacement of one or both of the nucleotide unit(s) with an isonucleotide—a nucleotide with a nucleobase shifted from 1' position to 2'. Such compounds may find utility as an anti-viral and anti-cancer agent, act as adjuvants in vaccines or may be used in the treatment of allergic or other inflammatory diseases.

In one embodiment, the present disclosure provides a compound of formula (J):

(J)

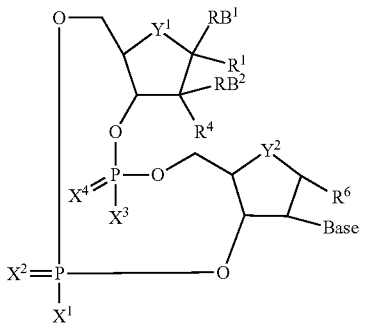

or an enantiomer, hydrate, solvate, or pharmaceutically acceptable salt or addition salt thereof, wherein $Y^1$ and $Y^2$ are each independently —O— or —$CH_2$—;

$X^1$ and $X^3$ are each independently OH, SH, $OR^{15}$, or $SR^{15}$;

$X^2$ and $X^4$ are each independently O or S;

$RB^1$ is selected from Base' and H, $RB^2$ is selected from Base' and H, wherein one of $RB^1$ and $RB^2$ is Base';

$R^1$ is H or CN or F or Cl;

$R^4$ is H or OH or F;

$R^6$ is selected from H, CN, $N_3$, F, Cl, $COOR^{15}$, $CON(R^{15})_2$, $C_1$-$C_6$ alkyl, $C_2$-$C_6$ alkenyl, $C_2$-$C_6$ alkynyl, $OR^{15}$, $SR^{15}$, and $N(R^{15})_2$;

each $R^{15}$ is independently H, —C(=Z)$R^{16}$, —C(=Z)$OR^{16}$, —C(=Z)$SR^{16}$, —C(=Z)N($R^{16}$)$_2$, —$CH_2$—Z—C(=Z)$R^{16}$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each $R^{16}$ is independently H, $C_1$-$C_{12}$ alkyl, $C_2$-$C_{12}$ alkenyl, $C_2$-$C_{12}$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl; preferably each $R^{16}$ is independently H, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each Z is independently O or S;

Base' and Base are each independently:

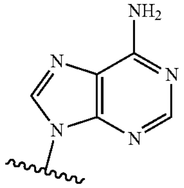
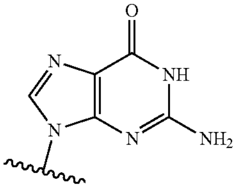
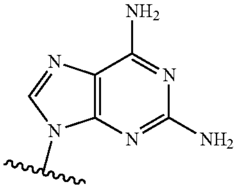
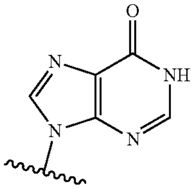
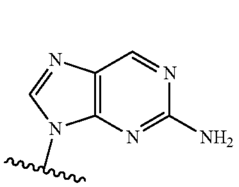
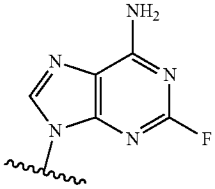
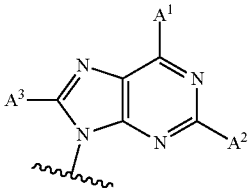
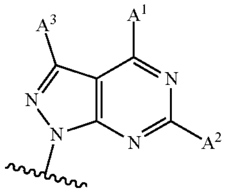
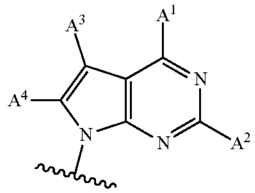
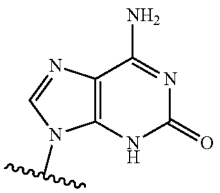
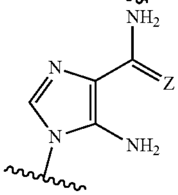
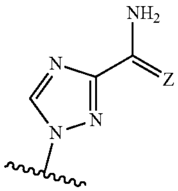
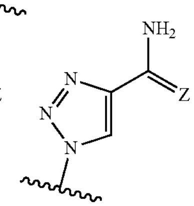

-continued

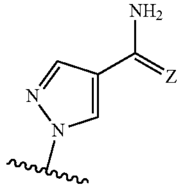
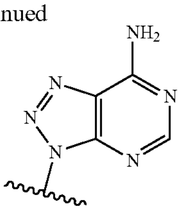
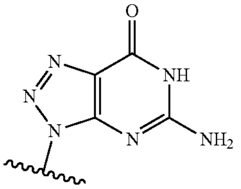
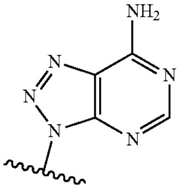

or

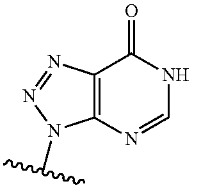

wherein $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$; and wherein the $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl independently in each instance is optionally substituted with 1, 2, or 3 substituents independently selected from —OH; —SH; —$NH_2$; =O; =NH; =S; halogen; —$N_3$; $C_6$-$C_{10}$ aryl optionally substituted with 1, 2, or 3 substituents independently selected from —OH, —CN, —O(C=O)$OR^B$, —O(C=O)$R^B$, and —$COOR^B$; unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino; unsubstituted $C_1$-$C_6$ dialkylamino; —CN; —O(C=O)$OR^B$; —O(C=O)$R^B$; and —$COOR^B$; wherein $R^B$ is H or unsubstituted $C_1$-$C_6$ alkyl.

In some embodiments of formula (J), $R^6$ is H.

In some embodiments of formula (J), $R^{15}$ is —$CH_2$—Z—C(=Z)$R^{16}$.

In some embodiments, $Y^1$ is —O— and $Y^2$ is —$CH_2$—, or $Y^1$ is —$CH_2$— and $Y^2$ is —O—.

In some embodiments, the present disclosure provides a compound of formula (J) for use as a medicament.

Preferably, the present disclosure provides a compound of formula (J) for use in treatment of inflammation, allergic and autoimmune diseases, cancer, and diseases caused by viruses such as hepatitis B virus, human immunodeficiency virus, coronaviruses (e.g. SARS-CoV-2) and flaviviruses.

In some embodiments, the present disclosure provides a compound of formula (J) for use as component of immunogenic compositions or for use as vaccine adjuvant.

In some embodiments, a pharmaceutical composition comprises the compound of formula (J), or an enantiomer, hydrate, solvate, or pharmaceutically acceptable salt thereof, and a pharmaceutically acceptable carrier, excipient, and/or diluent.

In some embodiments, the invention provides a method of treating or preventing a disease or disorder, e.g., a method of treating or preventing a viral infection, hepatitis B virus infection, HIV infection, coronavirus infection, flavivirus infection, hyperproliferative disease or cancer, comprises administering to a human or animal in need thereof a therapeutically effective amount of a compound of formula (J), or an enantiomer, hydrate, solvate, or pharmaceutically acceptable salt thereof, or a pharmaceutical composition of any of the foregoing.

In some embodiments, the invention provides a method of enhancing the efficacy of a vaccine comprises administering a therapeutically effective amount of a compound of formula (J), or an enantiomer, hydrate, solvate, or pharmaceutically acceptable salt thereof, or a pharmaceutical composition of any of the foregoing.

In some embodiments, the invention provides a method of modulating the activity of STING adaptor protein to induce production of a type I interferon, cytokine and/or chemokine dependent on the STING adaptor protein, e.g., inducing a STING adaptor protein-dependent type I interferon, cytokine or chemokine in a human or animal, comprises administering a therapeutically effective amount of a compound of Formula (J), or an enantiomer, hydrate, solvate, or pharmaceutically acceptable salt thereof, or a pharmaceutical composition of any of the foregoing.

The disclosure provides novel 3'3' cyclic dinucleotides, comprising at least one isonucleotidic unit, that bind to and modulate the activity of, e.g., activate, the STING protein. The dinucleotides have at least one nucleobase shifted from a C-1' position to a C-2' position of a sugar ring as a difference to naturally occurring nucleotides.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or "$C_u$-$C_v$" indicates that the following group has from u to v carbon atoms, where u and v are integers. For example, "$C_{1-6}$alkyl" or "$C_1$-$C_6$ alkyl" indicates that the alkyl group has from 1 to 6 carbon atoms.

"Alkyl" is a linear or branched saturated monovalent hydrocarbon. For example, an alkyl group can have 1 to 12 carbon atoms (i.e., $C_{1-12}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), and octyl ($—(CH_2)_7CH_3$).

"Alkoxy" refers to the group —O-alkyl, where alkyl is as defined above. For example, $C_{1-4}$alkoxy refers to an —O-alkyl group having 1 to 4 carbons.

"Alkenyl" is a linear or branched monovalent hydrocarbon radical with at least one carbon-carbon double bond. For example, an alkenyl group can have 2 to 8 carbon atoms (i.e., $C_{2-8}$ alkenyl) or 2 to 6 carbon atoms (i.e., $C_{2-6}$ alkenyl) or 2 to 4 carbon atoms (i.e., $C_{2-4}$ alkenyl). Examples of alkenyl groups include, but are not limited to, ethenyl ($—CH{=}CH_2$), allyl ($—CH_2CH{=}CH_2$), and $—CH_2—CH{=}CH—CH_3$. Alkenyl groups can be unsubstituted or substituted.

"Alkynyl" is a linear or branched monovalent hydrocarbon radical with at least one carbon-carbon triple bond. For example, an alkynyl group can have 2 to 8 carbon atoms (i.e., $C_{2-8}$ alkynyl) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl ($—C{\equiv}CH$), propargyl ($—CH_2C{\equiv}CH$), and $—CH_2—C{\equiv}C—CH_3$. Alkynyl groups can be unsubstituted or substituted.

Alkylamino is $—HNR_b$ group, where $R_b$ is an alkyl.

Alkylthio is $—SR_b$ group, where $R_b$ is an alkyl.

"Halo" or "halogen" as used herein refers to fluoro (—F), chloro (—Cl), bromo (—Br) and iodo (—I).

"Aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. Non-limiting examples of aryl groups include, but are not limited to, phenyl, indenyl, naphthyl, 1,2,3,4-tetrahydronaphthyl, anthracenyl, and the like. Aryl groups can be unsubstituted or substituted.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl. Heteroaryl groups can be unsubstituted or substituted.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl. Cycloalkyl groups can be unsubstituted or substituted.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 3 to about 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3] heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0] hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like. Heterocyclyl groups can be unsubstituted or substituted.

"Oxo" as used herein refers to =O.

"Substituted" as used herein, and unless defined otherwise in the immediate context, refers to substitution with one or more substituents (e.g., 1, 2, 3, or 4 or more) selected from the group consisting of —OH, —SH, $—NH_2$, =O, =NH, =S, ≡N, halogen, $—N_3$, $C_{1-6}$ alkyl, $C_{1-6}$ alkoxy, $C_{1-6}$ alkylthio, $C_{1-6}$ alkylamino, $C_{1-6}$ dialkylamino, —CN, $—O(C{=}O)OR^B$, $—O(C{=}O)R^B$ and $—COOR^B$, where R B is hydrogen or $C_1$ to $C_6$ alkyl.

A "compound of the present disclosure" includes compounds disclosed herein, for example a compound of the present disclosure includes compounds of Formula (J), (Ja), (Jb), (I), (Ia), (Ib), (IIa), (IIb), (IIIa) and/or (IIIb), including the compounds of the Examples.

"Treatment" or "treat" or "treating" as used herein includes one or more of the following: decreasing one or more symptoms resulting from the disease or condition, and/or diminishing the extent of the disease or condition; ameliorating the disease state, delaying the progression of the disease, increasing the quality of life, and/or prolonging survival.

"Delaying" as used herein means to defer, hinder, slow, retard, stabilize and/or postpone development of the disease or condition. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. In some instances, prevention may be understood as a reduction of the risk of cancer, but not a complete elimination of the occurrence of a cancer.

In certain embodiments, the term "preventing HBV infection" refers to administering to a subject who does not have a detectable HBV infection an anti-HBV therapeutic substance.

"Modulation" or "modulating" the activity of a protein, e.g., a STING adaptor protein, as used herein refers to alteration of the activity such that the activity increases or decreases. In some embodiments, the modulation increases the activity.

As used herein, the term "viral infection" or "disease caused by virus" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "enhancing" refers to any form of increase in the immunogenic activity of an effective dosage of a vaccine as a result of administering to an animal or a human a therapeutically effective dose of a compound of the present disclosure, at any time prior to, simultaneous with, or just after administration to the same animal or human of the effective dosage of a vaccine.

"At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art "Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents.

In some embodiments, a therapeutically effective amount of a compound provided herein or pharmaceutically acceptable salt thereof, may (i) reduce the number of diseased cells; (ii) reduce tumor size; (iii) inhibit, retard, slow to some extent, and preferably stop the diseased cell infiltration into peripheral organs; (iv) inhibit tumor metastasis; (v) inhibit tumor growth; (vi) prevent or delay occurrence and/or recurrence of a tumor; and/or (vii) relieve to some extent one or more of the symptoms associated with cancer or hyperproliferative disease. In some embodiments, a therapeutically effective amount is sufficient to ameliorate, palliate, lessen, and/or delay one or more of symptoms of cancer or hyperproliferative disease.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved as being acceptable for use in humans or domestic animals.

Provided are also pharmaceutically acceptable salts, addition salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, y-hydroxybutyrates, glycolates, tartrates, and mandelates. Lists of other suitable pharmaceutically acceptable salts are found in Remington: The Science and Practice of Pharmacy, $21^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal, an alkaline earth metal, ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule.

Examples of isotopes that can be incorporated into the disclosed compounds also include isotopes, such as $^2H$, $^3H$, $^{11}C$, $^{13}C$, $^{14}C$, $^{13}N$, $^{15}N$, $^1O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{13}C$, $^{18}F$, $^{15}O$ and $^{13}N$, can be useful in Positron Emission Topography (PET) studies for examining substrate receptor occupancy. Isotopically-labeled compounds of Formula (J) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic and optically pure forms. When the compounds described herein contain olefinic double bonds or other centres of geometric asymmetry, and unless specified otherwise, it is intended that the compounds include both E and Z geometric isomers. Likewise, all tautomeric forms are also intended to be included. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure includes "enantiomers", which refers to two stereoisomers whose molecules are non-superimposable mirror images of one another.

"Tautomer" as used herein refers to a proton shift from one atom of a molecule to another atom of the same molecule. The present disclosure includes tautomers of any said compounds.

"Solvate" as used herein refers to the result of the interaction of a solvent and a compound. Solvates of salts of the compounds described herein are also provided. Hydrates of the compounds described herein are also provided.

"Hydrate" as used herein refers to a compound of the disclosure that is chemically associated with one or more molecules of water.

In one preferred embodiment, the compound of formula (J) is a compound of formula (Ja):

(Ja)

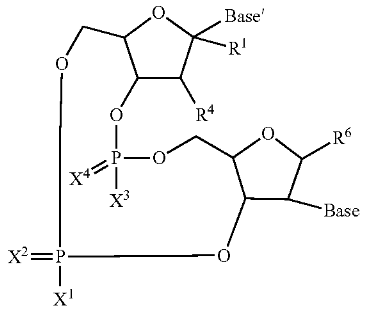

or an enantiomer, hydrate, solvate, or pharmaceutically acceptable salt or addition salt thereof, wherein $X^1$ and $X^3$ are each independently OH, SH, $OR^{15}$ or $SR^{15}$;

$X^2$ and $X^4$ are each independently O or S;

$R^1$ is H or CN or F or Cl;

$R^4$ is H or OH or F;

$R^6$ is selected from H, CN, $N_3$, F, Cl, $COOR^{15}$, $CON(R^{15})_2$, $C_1$-$C_6$ alkyl, $C_2$-$C_6$ alkenyl, $C_2$-$C_6$ alkynyl, $OR^{15}$, $SR^{15}$, and $N(R^{15})_2$;

each $R^{15}$ is independently H, —C(═Z)$R^{16}$, —C(═Z)$OR^{16}$, —C(═Z)$SR^{16}$, —C(═Z)$N(R^{16})_2$, —$CH_2$—Z—C(═Z)$R^{16}$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each $R^{16}$ is independently H, $C_1$-$C_2$ alkyl, $C_2$-$C_{12}$ alkenyl, $C_2$-$C_{12}$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl; preferably each $R^{16}$ is independently H, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each Z is independently O or S;

and the remaining substituents are as defined for formula (J).

In some embodiments, the compound of formula (J) has the structure of formula (I):

(I)

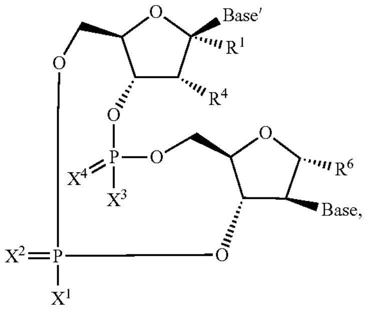

or an enantiomer, hydrate, solvate, or pharmaceutically acceptable salt thereof, wherein the substituents $R^1$, $R^4$, and $R^6$, $X^1$, $X^2$, $X^3$, $X^4$ have the meanings as defined for formula (J). Preferably, in formula (I), $R^6$ is H.

In some embodiments of the compound of formula (J), (Ja) and/or (I), $X^2$ and/or $X^4$ is/are S and $X^1$ and/or $X^3$ is/are OH.

In some embodiments of the compound of formula (J), (Ja) and/or (I), $X^2$ and/or $X^4$ is/are O and $X^1$ and/or $X^3$ is/are $SR^{15}$.

In some embodiments, the compound of formula (J) has a structure of formula (II):

(II)

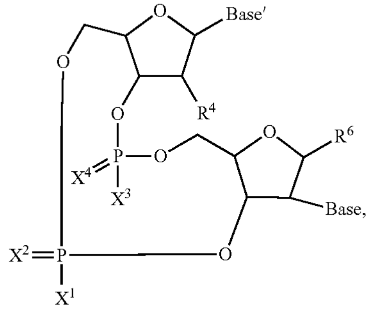

or an enantiomer, hydrate, solvate, or pharmaceutically acceptable salt thereof.

In some embodiments, the compound of formula (J) has a structure of formula (III):

(III)

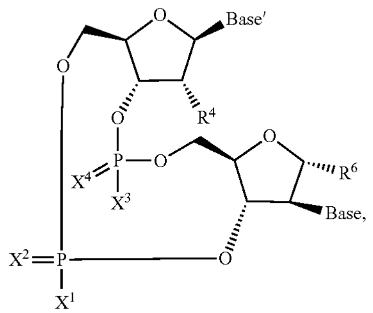

or an enantiomer, hydrate, solvate, or pharmaceutically acceptable salt thereof.

In some embodiments of the compound of formula (J), (Ja), (I), (II) and/or (III), $X^1$ and $X^3$ are each independently $OR^{15}$ or SH. In some embodiments, $X^1$ and $X^3$ are each independently $SR^{15}$ or $OR^{15}$. In some embodiments, $R^{15}$ is $C_1$-$C_6$ alkyl optionally substituted with 1 or 2 —O(C═O)$OR^B$; —O(C═O)$R^B$; or —$COOR^B$, for example, $R^{15}$ can be a $C_1$-$C_6$ alkyl substituted with a —O(C═O)$OR^B$. In some embodiments, $R^B$ is a $C_1$-$C_6$ alkyl, such as methyl, ethyl, n-propyl, isopropyl, n-butyl, tert-butyl, sec-butyl, n-pentyl, n-hexyl, sec-hexyl, or tert-hexyl. In some embodiments, $R^{15}$ is —$CH_2$—Z—C(═Z)$R^{16}$, wherein Z is O or S (preferably O) and wherein $R^{16}$ is a $C_1$-$C_{12}$ alkyl, such as methyl, ethyl, n-propyl, isopropyl, n-butyl, tert-butyl, sec-butyl, n-pentyl, sec-pentyl, tert-pentyl, n-hexyl, sec-hexyl, tert-hexyl, octyl, or methylcyclohexyl (preferably tert-butyl, tert-pentyl, octyl or methylcyclohexyl).

In some embodiments, $X^1$ and $X^3$ are each $OR^{15}$, wherein $R^{15}$ is $CH_2$ substituted with an —O(C═O)$R^B$, wherein $R^B$ is tert-butyl. In some embodiments, $X^1$ and $X^3$ are each $OR^{15}$, wherein $R^{15}$ is $CH_2$ substituted with an —O(C═O)O$R^B$, wherein $R^B$ is isopropyl. In some embodiments, $X^1$ is OH or SH, and $X^3$ is OH. In some embodiments, $X^1$ and $X^3$ are each OH. In some embodiments, $X^1$ is SH and $X^3$ is OH.

In some embodiments, $X^1$ and $X^3$ are each $OR^{15}$, wherein $R^{15}$ is —$CH_2$—O—C(═O)$R^{16}$, wherein $R^{16}$ is $C_1$-$C_{12}$ alkyl or $C_3$-$C_7$ cycloalkyl. Preferably, $R^{16}$ is tert-butyl, methylcyclohexyl, dimethylpropyl, heptyl, octyl, isopropyl.

In some embodiments of the compound of formula (J), (Ja), (I), (II) and/or (III), $R^6$ is H, OH, CN, $N_3$, or $C_1$-$C_6$ alkyl. In some embodiments, $R^6$ is H, OH, CN, or $C_1$-$C_6$ alkyl. In some embodiments, $R^6$ is H, OH. In some embodiments, $R^6$ is H. In some embodiments, $R^6$ is OH.

In some embodiments of the compound of formula (J), (Ja), (I), (II) and/or (III), Base' and Base are each independently selected from:

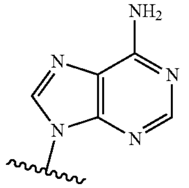
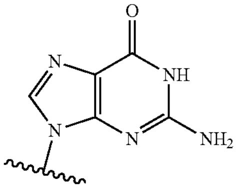
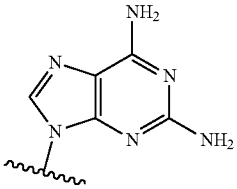
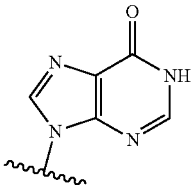
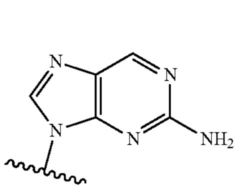
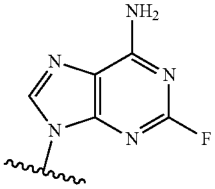
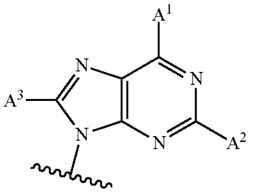
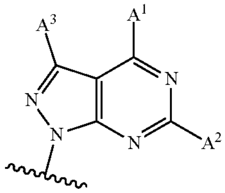
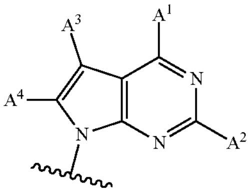
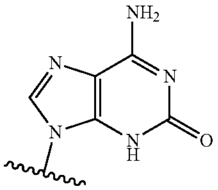

wherein

A, $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$.

In some embodiments of the compound of formula (J), (Ja), (I), (II) and/or (III), Base' and Base are each independently selected from:

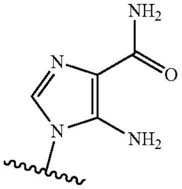
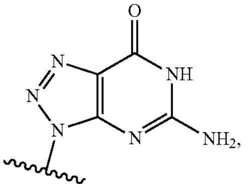
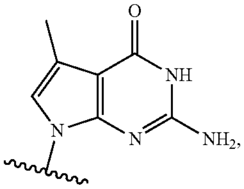
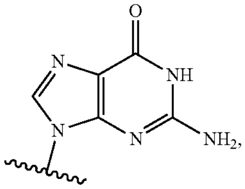
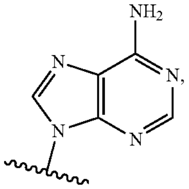
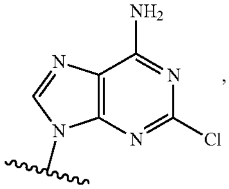 ,
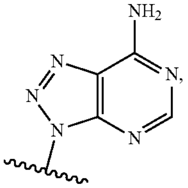
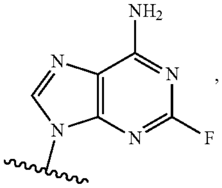 ,
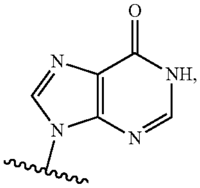
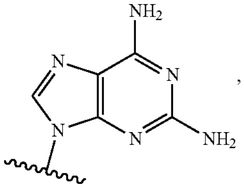 ,
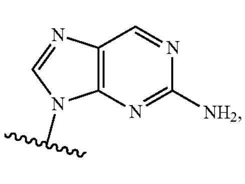
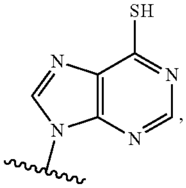
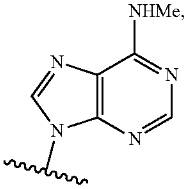
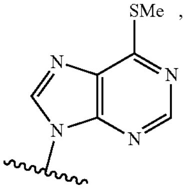 ,
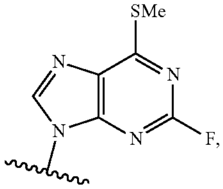
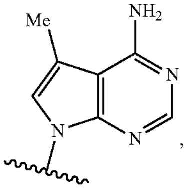
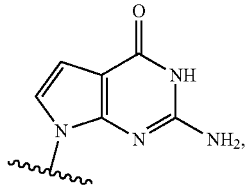
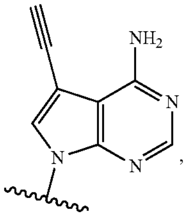

-continued
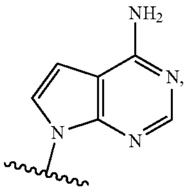
or
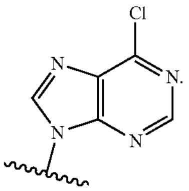
In some embodiments, Base' is:
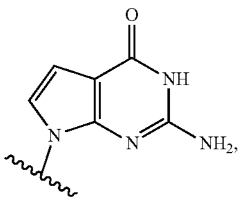
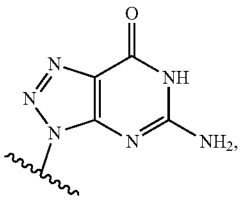
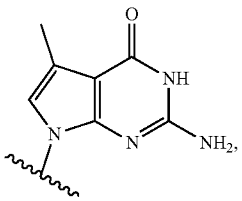
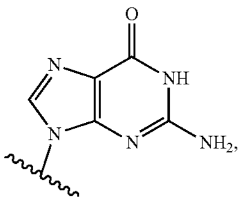
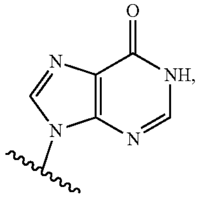
or
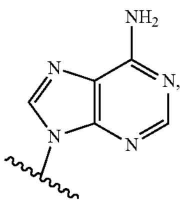
and Base is
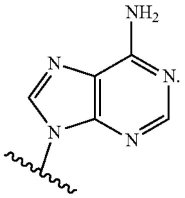 [SMILES: *n1cnc2c(N)ncnc21]
In some embodiments, Base' is
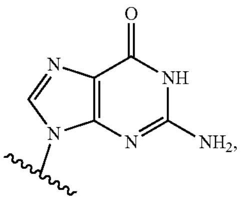 [SMILES: *n1cnc2c(=O)[nH]c(N)nc21]
and Base is:
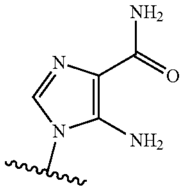
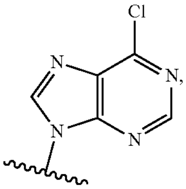
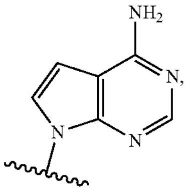
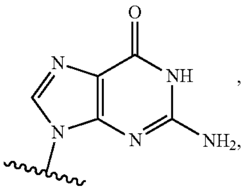
,
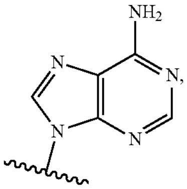
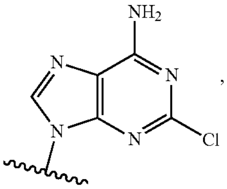
,
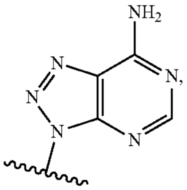
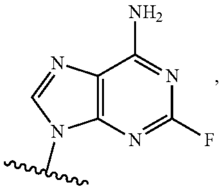
,
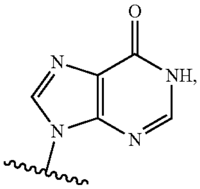
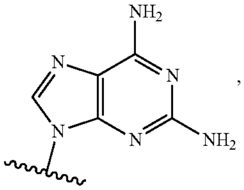
, -continued
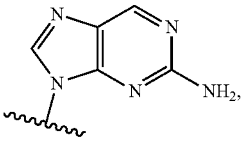
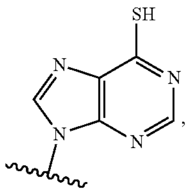
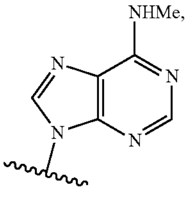
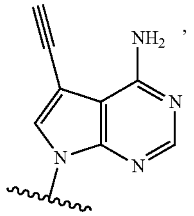
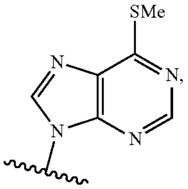
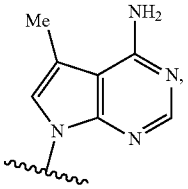
or
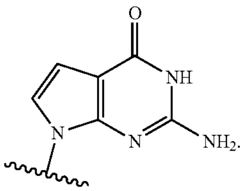
In some embodiments of the compound of formula (J), (Ja), (I), (II) and/or (III), Base' and Base are each independently:
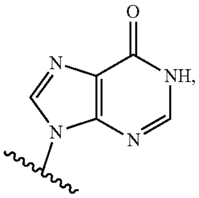
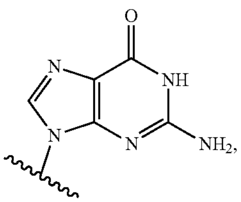
or
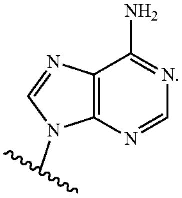
In some embodiments of the compound of formula (J), (Ja), (I), (II) and/or (III), Base' is Base is
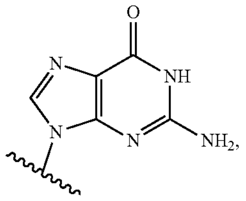
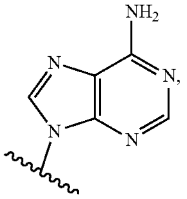
or
Base' is Base is
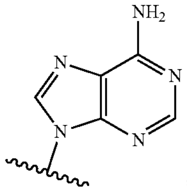
,
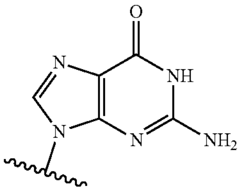
,
or
Base' is Base is
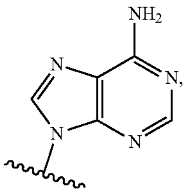
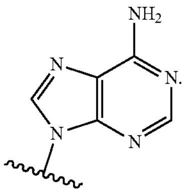
In some embodiments of the compound of formula (J), the compound has the structure selected from:
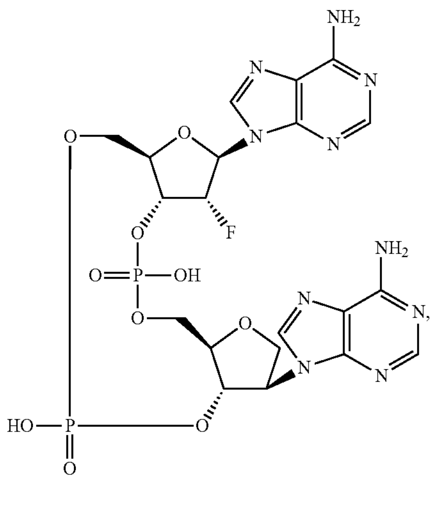

-continued

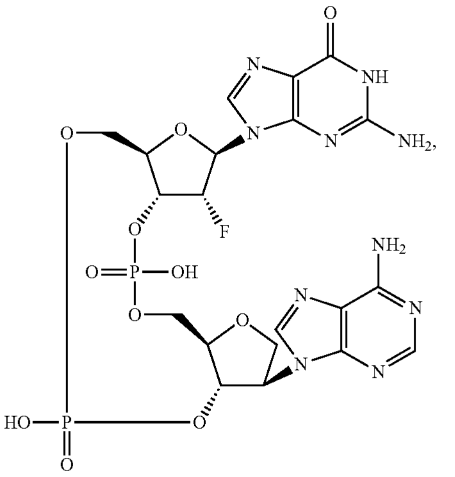

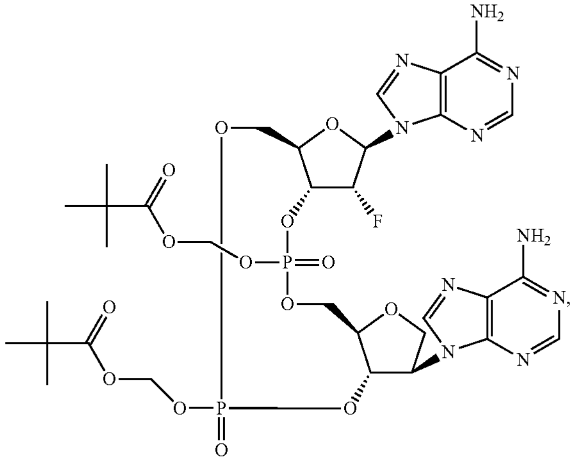

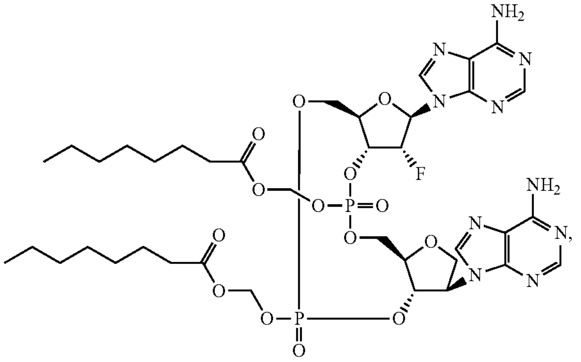

-continued

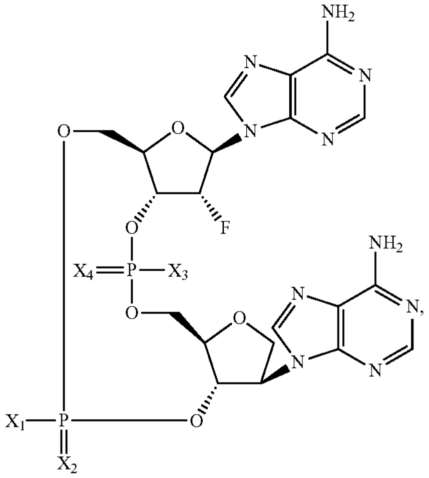

wherein $X^1$, $X^2$, $X^3$, $X^4$ are as defined for structure (J);

or an enantiomer, hydrate, solvate, or pharmaceutically acceptable salt thereof.

A compound of the disclosure, e.g, a compound of formula (J), (Ja), (I), (II) and/or (III), can be shown in a number of equivalent depictions. For example, a compound of Formula (III) is typically depicted herein as shown above wherein each nucleoside is shown in the 5' to 3'-direction from upper left to lower right:

(III)

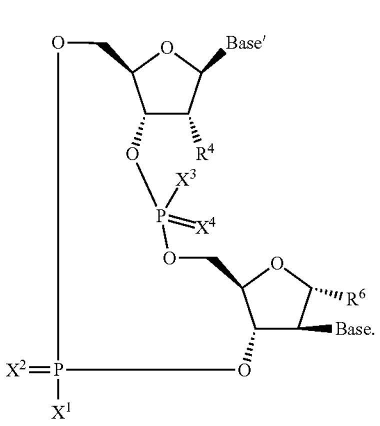

The above compound of Formula (III) is equivalent to a compound of Formula (III) as shown below:

(III)

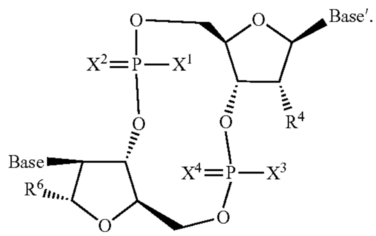

Further, each of the previous depictions are equivalent to the below depiction of a compound of Formula (III):

(III)

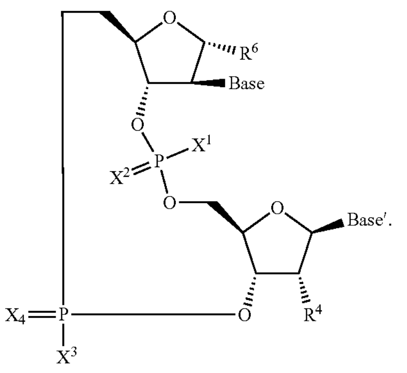

I. Compositions

In certain embodiments, the present disclosure provides a pharmaceutical composition comprising a compound of the present disclosure (e.g. a compound of Formula (J), (Ja), (I), (II) and/or (III)), or a pharmaceutically acceptable salt or solvate thereof, and a pharmaceutically acceptable excipient.

In certain embodiments, the pharmaceutical composition comprises one or more additional therapeutic agent, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is provided as a solid dosage form, including a solid oral dosage form, including capsules, sachets or tablets each containing a predetermined amount of the active ingredient. In one embodiment, the pharmaceutical composition is a tablet.

The compositions include those suitable for various administration routes, including oral administration. The compositions may be presented in unit dosage form and may be prepared by any of the methods well known in the art of pharmacy.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

The compounds of the present disclosure (also referred to herein as the active ingredients) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer A compound of the present disclosure may be combined with one or more additional therapeutic agents in any dosage amount of the compound of the present disclosure (e.g., from 1 mg to 1000 mg of compound).

Kits that comprise a compound of the present disclosure, or an enantiomer, or pharmaceutically acceptable salt thereof, or a pharmaceutical composition containing any of the above, are also included in the present disclosure.

In one embodiment, kits comprising a compound of the present disclosure, or an enantiomer, hydrate, solvate, or a pharmaceutically acceptable salt thereof, in combination with one or more (e.g., one, two, three, four, one or two, or one to three, or one to four) additional therapeutic agents are provided.

The disclosure further includes a compound of the invention or a pharmaceutical composition as described above for use in modulating STING protein activity, to induce STING-dependent production of type I interferons, cytokines or chemokines.

The disclosure further includes a compound of the invention or a pharmaceutical composition as described above for use in treating or preventing viral infection, infection caused by hepatitis B virus, by human immunodeficiency virus, coronaviruses (e.g. SARS-CoV-2) and flaviviruses, allergic diseases, inflammatory diseases, hyperproliferative disease or cancer.

In some embodiments, the compound of the invention or the pharmaceutical compositions described above are for use in a human or an animal.

The Stimulator of interferon genes (STING) adaptor protein, also known as STING, STING protein, transmembrane protein 173 (TMEM173), MPYS, mediator of IRF3 activation (MITA), or endoplasmic reticulum interferon stimulator (ERIS), is a protein that in humans is encoded by the TMEM173 gene (UniProt code Q86WV6; NCBI Reference Sequences: NP_938023.1 (isoform 1) and NP_001288667 (isoform 2)). STING adaptor protein is believed to function as both a direct cytosolic DNA sensor (CDS) and an adaptor protein in Type I interferon signaling through different molecular mechanisms. STING adaptor protein has been shown to activate downstream transcription factors STAT6 and IRF3 through TBK1, and NF-κB through IKKβ, which can effect an antiviral response or innate immune response against an intracellular pathogen. STING adaptor protein plays a role in innate immunity by inducing type I interferon production when cells are infected with intracellular pathogens, such as viruses, mycobacteria and intracellular parasites. Type I interferon, mediated by STING adaptor protein, protects infected cells and nearby cells from local infection by autocrine and paracrine signaling.

Activation of STING adaptor protein in turn activates protein kinase TBK1, which subsequently activates downstream transcription factors NF-κB and IRF-3. Activation of STING adaptor protein ultimately is believed to result in the release of type I and III interferons as well as a variety of cytokines and chemokines such as IL-6, TNF-α and INF-γ. Accordingly, induction of a STING adaptor protein-dependent type I interferon, cytokine or chemokine in a human or animal results in the activation of one or more of NF-κB, IRF-3, a type I interferon, a type III interferon, IL-6, TNF-α, and INF-γ in said human or animal.

Viral infections that can be treated or prevented by the compounds of the present disclosure can be any infection caused by a virus, e.g., a virus from the Hepadnaviridae family of viruses, e.g., hepatitis B; or any retrovirus, e.g., an alpharetrovirus, such as Rous sarcoma virus; a coronavirus, such as SARS-CoV-2; a flavivirus, such as Tick-borne encephalitis virus, Dengue virus or Zika virus; a betaretrovirus, such as simian retrovirus; a deltaretrovirus, such as bovine leukemia virus or human T-lymphotrophic virus (HTLV) including HTLV-1, HTLV-2, and HTLV-3; a gammaretrovirus, such as murine leukemia virus or feline leukemia virus; or a lentivirus, such as human immunodeficiency virus (HIV) including HIV-1 and HIV-2, simian immunodeficiency virus, equine infectious anemia virus, bovine immunodeficiency virus, rabbit endogenous lentivirus type K (RELIK), or feline immunodeficiency virus.

Hyperproliferative diseases that can be treated or prevented by the compounds of the present disclosure include diseases caused by excessive growth of non-cancer cells. Such conditions include but are not limited to psoriasis, actinic keratoses, and seborrheic keratoses, warts, keloids, and eczema.

Cancers that can be treated or prevented by the compounds of the disclosure include solid tumors and lymphomas, including but not limited to adrenal cancer, bladder cancer, bone cancer, brain cancer, breast cancer, colon cancer, colorectal cancer, eye cancer, head-and-neck cancer, kidney cancer such as renal cell carcinoma, liver cancer, lung cancer such as non-small cell lung cancer, ovarian cancer, pancreatic cancer, prostate cancer, skin cancer such as squamous cell carcinoma and melanoma, thyroid cancer, uterine cancer, vaginal cancer, and myeloma such as multiple myeloma. The cancer can be naïve, or relapsed and/or refractory.

In some embodiments, the cancer is Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In some embodiments, the cancer is selected from Hodgkin's lymphoma, non-Hodgkin's lymphoma (NHL), indolent non-Hodgkin's lymphoma (iNHL), and refractory iNHL. In some embodiments, the cancer is indolent non-Hodgkin's lymphoma (iNHL). In some embodiments, the cancer is refractory iNHL. In some embodiments, the cancer is chronic lymphocytic leukemia (CLL). In some embodiments, the cancer is diffuse large B-cell lymphoma (DLBCL).

In some embodiments, the cancer is a solid tumor selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the compounds provided herein may be used to treat cancer at various stages. By way of example, the cancer stage includes but is not limited to early, advanced, locally advanced, remission, refractory, reoccurred after remission and progressive.

Subjects

The compounds of the invention provided herein may be used to treat a subject (e.g., human) who has been diagnosed with or is suspected of having cancer. As used herein, a subject refers to a mammal, including, for example, a human.

The disclosure includes a cyclic dinucleotide provided herein, including compounds of the disclosure, or an enantiomer, hydrate, solvate, or pharmaceutically acceptable salt thereof for use as a medicament in a human or animal.

In certain embodiments, a method for treating or preventing an infectious disease, a viral infection, hepatitis B infection, HIV infection, cancer, or a hyperproliferative disease in a human having or at risk of having the disease is provided, comprising administering to the human a therapeutically effective amount of a compound disclosed herein, e.g., a compound of Formula (J), (Ja), (I), (II) and/or (III), or a pharmaceutically acceptable salt thereof, in combination with a therapeutically effective amount of one or more (e.g., one, two, three, four, one or two, one to three, or one to four) additional therapeutic agents. In one embodiment, a method for treating an infectious disease, a viral infection, hepatitis B infection, HIV infection, coronavirus infection (e.g. SARS-CoV-2), flavivirus infection, cancer, or a hyperproliferative disease in a human having or at risk of having the disease is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

EXAMPLES

The embodiments are also directed to processes and intermediates useful for preparing the subject compounds or pharmaceutically acceptable salts thereof.

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in schemes below, and the particular examples that follow.

The specific 3'3'-cyclic dinucleotides detailed in the Examples were synthesized according to the general synthetic method described below. Compounds were named using ChemAxon (Budapest, HU) unless otherwise indicated.

Analytical HPLC, mass spectra, UV absorbancy and purity of compounds were measured on Waters UPLC-MS system consisted of Waters UPLC H-Class Core System, UPLC PDA detector and Mass spectrometer Waters SQD2. MS method used was ESI+ and/or ESI-, cone voltage=30 V, mass detector range 100-1000 Da or 500-1600 Da. Two sets of HPLC conditions were used as indicated: (a) C18 (column: ProntoSIL, Prontopearl C18 SH 2.2 μm, 100×2.0 mm; LC method: $H_2O/CH_3CN$, 0.1% formic acid as modifier, gradient 0-100%, run length 7 min, flow 0.5 ml/min) and (b) HILIC (column: SeQuant ZIC-pHILIC, 5 μm, polymeric, 50×2.1 mm; LC method: $CH_3CN$/0.01M aqueous ammonium acetate gradient 10-60%, run length 7 min, flow 0.3 ml/min).

The abbreviations used in the Examples shown below include the following:

| Abbreviations | |
|---|---|
| Ac | Acetyl |
| ACN | Acetonitrile |
| AcOH | Acetic acid |
| Boc | tert-Butylcarbonyl |
| Bz | Benzoyl |
| CE | 2-cyanoethyl |
| DCA | Dichloroacetic acid |
| DCE | 1,2-dichloroethane |
| DCM | Dichloromethane |
| DIAD | Diisopropyl azodicarboxylate |
| DMF | Dimethylformamide |
| DMTr | 4,4-dimethoxytrityl |
| DMOCP | 2-Chloro-5,5-dimethyl-1,3,2-dioxaphosphorinane 2-oxide |
| DMSO | Dimethylsulfoxide |
| EtOH | Ethanol |
| HILIC | Hydrophilic interaction chromatography |
| iPr | Isopropyl |
| MeOH | Methanol |

-continued

| Abbreviations | |
|---|---|
| NIS | N-Iodosuccinimide |
| Ph | Phenyl |
| PNT | 4-pentenoyl |
| $PNT_2O$ | 4-Pentenoic anhydride |
| POM | Pivaloyloxymethyl |
| py | Pytidine |
| THF | tetrahydrofuran |
| TBHP | tert-Butyl hydroperoxide solution |
| TEA | Triethylamine |
| TEAB | triethylammonium bicarbonate |
| TES | Triethylsilane |
| TMS | Trimethylsilyl |
| TFA | Trifluoroacetic acid |
| FBS | Fetal bovine serum |
| HEPES | 4-(2-hydroxyethyl)-1-piperazineethanesulfonic acid |
| BSA | Bovine serum albumin |

Synthesis of (2R,3S,4R)-4-(6-benzamido-9H-purin-9-0-2-(hydroxymethyl)tetrahydrofuran-3-yl hydrogen phosphonate (6)

The synthesis of compound 6 from compound 1 was accomplished according to the synthetic scheme depicted in Scheme 3 below, and detailed in the following description.

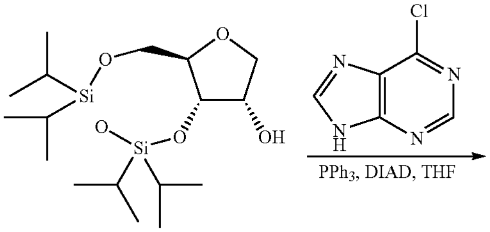

1

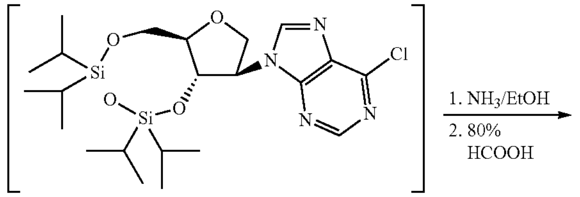

2

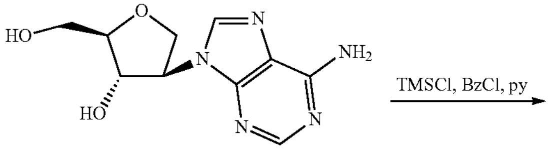

3

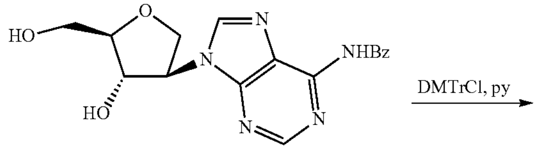

4

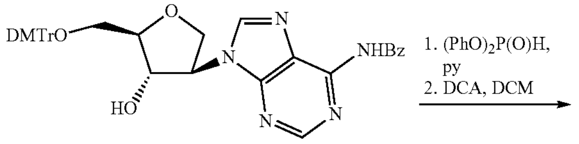

5

-continued

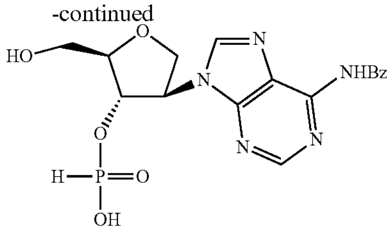

6

6-Chloro-9-46aR,9R,9aS)-2,2,4,4-tetraisopropyltetrahydro-6H-furo[3,2-f][1,3,5,2,4]trioxadisilocin-9-yl)-9H-purine (2)

A mixture of 1 (1.9 g, 5.05 mmol, *Nucleosides Nucleotides & Nucleic Acids,* 1997, 16, 67), 6-chlorpurine (1.169 g, 7.58 mmol) and triphenylphospine (2.66 g, 10.1 mmol) in THF (66 mL) was cooled to 0° C. and DIAD (2.02 ml, 10.1 mmol) was added dropwise in 10 minutes. After 30 minutes at ambient temperature was the reaction mixture heated to 65° C. (bath) for 20 h. Volatiles were evaporated and the residue was purified by flash chromatography on silica gel (cyclohexane: ethyl acetate 0→35%). Product was contaminated by triphenylphosphine oxide and was used without further purification in the next step. ESI MS m/z (%): 513.2 (100) [M+H].

(2R,3S,4R)-4-(6-amino-9H-purin-9-yl)-2-(hydroxymethyl)tetrahydrofuran-3-ol (3)

Intermediate 2 was suspended in a mixture of ethanolic ammonia (60 mL, 4 M) and dioxane (30 mL) and this mixture was heated in a sealed tube at 90° C. for 24 hours. Volatiles were evaporated and the residue was azeotroped with dioxane (2x75 mL). The oily intermediate was dissolved in aq. HCOOH (110 mL. 80%) and the reaction mixture was heated to 65° C. for 18 h. Volatiles were evaporated, residue was azeotroped with ethanol (3x150 mL) and then dissolved in a mixture of ethanol (70 mL) and aq. ammonia (35 mL, 25%). Resulting solution was stirred for 3 h, volatiles were evaporated and the residue was azeotroped with ethanol (3x150 mL). Nucleoside 3 was purified by chromatography on silica gel (ethyl acetate→ethyl acetate:acetone:ethanol:water 36:6:5:3, 0-100%) to afford 3 (981 mg over two steps). $^1H$ NMR (400 MHz, DMSO-$d_6$) δ 8.19 (s, 1H), 8.15 (s, 1H), 7.23 (s, 2H), 5.76 (s, 1H), 4.96-4.83 (br s and m, 2H), 4.42-4.36 (m, 1H), 4.17 (dd, J=9.6, 6.6 Hz, 1H), 4.09 (dd, J=9.6, 5.0 Hz, 1H), 3.69 (ddd, J=6.1, 5.0, 3.2 Hz, 1H), 3.65-3.51 (m, 2H). $^{13}C$ NMR (101 MHz, DMSO-$d_6$) δ 156.21, 152.99, 149.61, 139.37, 118.91, 86.07, 75.86, 69.72, 62.12, 61.05. HRMS ESI ($C_{10}H_{13}N_5O_3$) calculated 252.1097, found: 252.1091.

N-(9-((3R,4S,5R)-4-hydroxy-5-(hydroxymethyl) tetrahydrofuran-3-yl)-9H-purin-6-yl)benzamide (4)

3 (498 mg, 1.98 mmol) was azeotroped with pyridine (3x20 mL), dissolved in pyridine (15 mL), cooled to 0° C. and TMSCl (1.89 mL, 14.7 mmol) was added dropwise during 3 minutes. Reaction mixture was stirred at 0° C. for 20 minutes and then at ambient temperature for 1.5 hours. Benzoyl chloride (0.45 mL, 3.9 mmol) was slowly added at 0° C. and the resulting solution was stirred overnight at ambient temperature. The reaction mixture was cooled to 0°

C., quenched with water (1.6 mL), and, after 15 minutes, aq. ammonia (4 mL, 25%). After further 15 minutes at 0° C. and 20 minutes at ambient temperature were all volatiles evaporated and the residue was extracted with ethyl acetate-ethanol mixture (50 ml, 2:1) and solids were filtered-off on a celite pad. Product was purified on silica gel (ethyl acetate→ethyl acetate:acetone:ethanol:water 36:6:5:3, 0-100%) to afford 580 mg of 4. $^1$H NMR (400 MHz, DMSO-$d_6$) δ 11.17 (s, 1H), 8.75 (s, 1H), 8.54 (s, 1H), 8.09-8.01 (m, 2H), 7.69-7.60 (m, 1H), 7.60-7.51 (m, 2H), 5.82 (d, J=5.4 Hz, 1H), 5.03 (dt, J=6.2, 4.8 Hz, 1H), 4.93 (t, J=5.6 Hz, 1H), 4.44 (td, J=5.6, 4.3 Hz, 1H), 4.28-4.16 (m, 2H), 3.73 (ddd, J=6.1, 4.8, 3.1 Hz, 1H), 3.65 (ddd, J=12.0, 5.3, 3.1 Hz, 1H), 3.58 (ddd, J=12.0, 5.9, 4.8 Hz, 1H). $^{13}$C NMR (101 MHz, DMSO-$d_6$) δ 166.2, 153.20, 152.47, 151.50, 150.38, 143.16, 133.63, 132.58, 128.63, 125.57, 86.16, 75.90, 69.59, 62.44, 60.92. HRMS ESI ($C_{17}H_{17}N_5O_4$) calculated 356.1359, found: 356.1360.

N-(9-((3R,4S,5R)-5-((bis(4-methoxyphenyl)(phenyl) methoxy)methyl)-4-hy droxytetrahydrofuran-3-yl)-9H-purin-6-yl)benzamide (5)

Compound 4 (559 mg, 1.57 mmol) was azeotroped with pyridine (2×20 mL), dissolved in pyridine (15 mL) and DMTrCl (556 mg, 1.73 mmol) was added in one portion at 0° C. Reaction mixture was stirred at ambient temperature for 15 h, quenched with satd. aq. NaHCO 3 (8 mL) and evaporated. Residue was dissolved in ethyl acetate (400 mL) and washed with saturated aqueous solution of $NaHCO_3$ (2×150 mL) and brine (150 mL). Organic phase was dried over sodium sulfate and evaporated. Product was purified by chromatography (toluene:acetone 1:1→1:2) on a TEA-deactivated silica to afford 5 (882 mg). $^1$H NMR (400 MHz, DMSO-$d_6$) δ 11.19 (bs, 1H), 8.75 (s, 1H), 8.50 (s, 1H), 8.07-8.03 (m, 2H), 7.67-7.62 (m, 1H), 7.58-7.52 (m, 2H), 7.437.38 (m, 2H), 7.33-7.19 (m, 7H), 6.91-6.86 (m, 4H), 5.82 (d, 1H, J=5.7 Hz), 5.05 (dt, 1H, J=7.2, 6.0 Hz), 4.56 (dt, 1H, J=6.8, 5.6 Hz), 4.37 (dd, 1H, J=9.6, 6.1 Hz), 4.30 (dd, 1H, J=9.6, 7.2 Hz), 3.94 (dt, 1H, J=6.9, 4.5 Hz), 3.73 (s, 6H), 3.19 (d, 2H, J=4.4 Hz). $^{13}$C NMR (101 MHz, DMSO-$d_6$) δ 165.62, 158.23, 152.55, 151.51, 150.49, 145.06, 143.37, 135.82, 135.79, 133.63, 132.61, 129.90, 128.66, 128.65, 128.00, 127.92, 126.83, 125.88, 113.36, 85.51, 83.49, 75.20, 68.74, 63.71, 62.32, 55.21. HRMS ESI ($C_{38}H_{35}N_5O_6$) calculated 658.2666, found: 658.2663.

(2R,3S,4R)-4-(6-benzamido-9H-purin-9-yl)-2-(hydroxymethyl)tetrahydrofuran-3-yl hydrogen phosphonate (6)

Compound 5 (403 mg, 0.61 mmol) was azeotroped with pyridine (2×10 mL), dissolved in pyridine (10 mL), and diphenyl phosphite (85%, 417 μL, 1.9 mmol) was added in one portion. After stirring at ambient temperature for 20 minutes, TEA (0.92 mL) was added followed by water (0.92 mL) and the reaction was stirred for further 20 minutes. Resulting solution was diluted with DCM (200 mL) and washed with saturated aqueous solution of $NaHCO_3$ (2×75 mL). Organic layer was dried over sodium sulfate and evaporated. Resulting intermediate was purified on FCC (DCM/1% $Et_3N$-MeOH 0-30%). To a solution of obtained intermediate in DCM (10 mL) was added water (200 μL, 11.1 mmol) followed by a solution of DCA (457 μL, 5.6 mmol) in DCM (5.1 mL). Reaction mixture was stirred at ambient temperature for 30 minutes and volatiles were evaporated. Purification on reverse phase FCC (ACN in 50 mM aqueous $NH_4HCO_3$, 0-30%) afforded 6 (192 mg, ammonium salt). $^1$H NMR (400 MHz, DMSO-$d_6$) δ 11.17 (s, 1H), 8.74 (s, 1H), 8.63 (s, 1H), 8.07-8.02 (m, 2H), 7.67-7.61 (m, 1H), 7.58-7.52 (m, 2H), 6.48 (d, 1H, J=588.2 Hz), 5.20 (dt, 1H, J=6.8, 5.2 Hz), 4.90 (ddd, 1H, J=10.8, 6.1, 4.9 Hz), 4.23 (dd, 1H, J=9.7, 6.8 Hz), 4.18 (dd, 1H, J=9.6, 5.4 Hz), 3.86 (dt, 1H, J=6.2, 4.4 Hz), 3.71 (dd, 1H, J=11.9, 4.5 Hz), 3.65 (dd, 1H, J=11.9, 4.3 Hz). $^{13}$C NMR (101 MHz, DMSO-$d_6$) δ 165.81, 152.46, 151.63, 150.37, 143.51, 133.63, 132.63, 128.68, 125.61, 84.81 (d,J= 3.0 Hz), 77.35 (d, J=4.4 Hz), 69.31, 61.36 (d, J=5.5 Hz), 61.30. $^{31}$P NMR (162 MHz, DMSO-$d_6$) δ 3.56. HRMS ESI ($C_{17}H_{18}N_5O_6P$) calculated 420.1073, found: 420.1073.

Synthesis of (2R,3S,4R)-2-(hydroxymethyl)-4-(6-(pent-4-enamido)-9H-purin-9-yl)tetrahydrofuran-3-yl hydrogen phosphonate (9)

The synthesis of compound 9 from compound 3 was accomplished according to the synthetic scheme depicted below, and detailed in the following description.

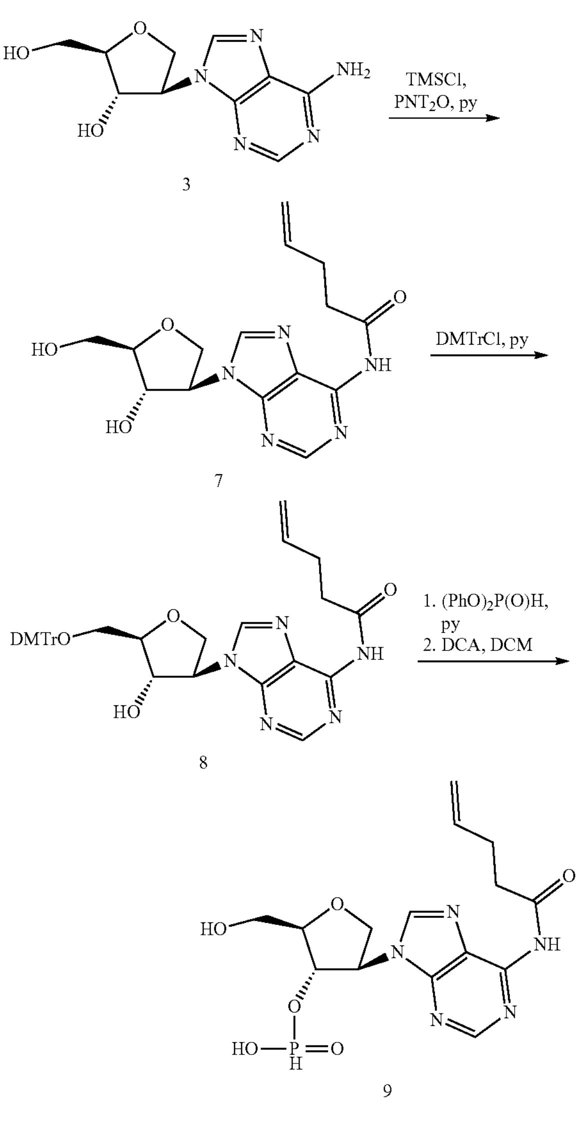

N-(9-((3R,4S,5R)-4-hydroxy-5-(hydroxymethyl) tetrahydrofuran-3-yl)-9H-purin-6-yl)pent-4-enamide (7)

Intermediate 3 (1 g, 4 mmol) was azeotroped with pyridine (2×10 mL), dissolved in pyridine (15 mL), and TMSCl (2.5 mL, 20 mmol) was added dropwise. After stirring the reaction mixture at ambient temperature for 1 hour, pentenoic anhydride (2.9 mL, 16 mmol) was added dropwise and stirring was continued for further 12 hours. TEA (1 mL) was added, and, after cooling to 0° C., water (4 mL) was added and stirring was continued for 5 minutes. Then aqueous ammonia was added (32%, 4 mL), while still at 0° C. and stirring was continued for another 30 minutes. Volatiles were quickly evaporated at 30° C. and the residue was passed through a plug of silica in DCM-MeOH 19:1 affording product (1.2 g) of ca 80% purity, suitable for next reaction. ESI MS m/z (%): 334.2 (100) [M+H].

N-(9-43R,4S,5R)-5-((bis(4-methoxyphenyl)(phenyl) methoxy)methyl)-4-hydroxytetrahydrofuran-3-yl)-9H-purin-6-yl)pent-4-enamide (8)

Partially protected nucleoside 7 (1.2 g, 80% purity, 3.0 mmol of pure) was azeotroped with pyridine (2×10 mL), dissolved in pyridine (15 mL) and DMTrCl (1.12 g, 3.2 mmol) was added at 0° C. in five portions. Reaction mixture was stirred at ambient temperature for 12 hours, after which all volatiles were evaporated. Residue was dissolved in small volume of DCM and applied to a preconditioned silicagel column (10% acetone in cyclohexane, 1% TEA), and flash chromatography (10-60% acetone in cyclohexane) afforded 8 (1.6 g). $^{1}$H NMR (400 MHz, DMSO-$d_6$) δ 10.69 (s, 1H), 8.64 (s, 1H), 8.47 (s, 1H), 7.42-7.36 (m, 2H), 7.32-7.18 (m, 7H), 6.90-6.84 (m, 4H), 5.88 (ddt, 1H, J=17.3, 10.3, 6.4 Hz), 5.79 (d, 1H, J=5.7 Hz), 5.08 (dq, 1H, J=17.3, 1.7 Hz), 5.05-4.91 (m, 2H), 4.53 (dt, 1H, J=6.8, 5.6 Hz), 4.36 (dd, 1H, J=9.6, 5.9 Hz), 4.27 (dd, 1H, J=9.6, 7.1 Hz), 3.92 (dt, 1H, J=6.7, 4.5 Hz), 3.73 (s, 6H), 3.16 (d, 2H, J=4.5 Hz), 2.68 (t, 2H, J=7.4 Hz), 2.36 (dtt, 2H, J=8.7, 7.3, 1.6 Hz). $^{13}$C NMR (101 MHz, DMSO-$d_6$) δ 171.07, 158.23, 152.13, 151.59, 149.66, 145.05, 142.94, 137.68, 135.80, 135.77, 129.89, 127.99, 127.91, 126.83, 123.77, 115.48, 113.35, 85.50, 83.59, 75.20, 68.70, 63.68, 62.34, 55.21, 35.56, 28.83. HRMS ESI ($C_{36}H_{37}N_5O_6$) calculated 636.2822, found: 636.2819.

(2R,3S,4R)-2-(hydroxymethyl)-4-(6-(pent-4-enamido)-9H-purin-9-yl)tetrahydrofuran-3-yl hydrogen phosphonate (9)

Partially protected nucleoside 8 (200 mg, 0.31 mmol) was azeotroped with pyridine (2×10 mL), dissolved in pyridine (10 mL) and diphenyl phosphite (85%, 860 μL, 3.82 mmol) was added in one portion. After stirring at ambient temperature for 20 minutes TEA (1.5 mL) was added followed by water (1.5 mL) and the reaction was stirred for further 20 minutes. Resulting solution was diluted with DCM and washed with saturated aqueous solution of $NaHCO_3$ and with water. Organic layer was dried over sodium sulfate and evaporated. To a solution of obtained intermediate in DCM (15 mL) was added water (229 μL, 12.7 mmol) and a solution of DCA (0.94 mL, 11.4 mmol) in DCM (10 mL) and the reactioin mixture was stirred at ambient temperature for 30 minutes, after which it was quenched with pyridine (2 ml). Purification and separation of isomers on reverse phase FCC (ACN in water, 0-50%) afforded 24 (119 mg) as triethylammonium salt. $^{1}$H NMR (400 MHz, DMSO-$d_6$) δ 10.68 (s, 1H), 8.64 (s, 1H), 8.61 (s, 1H), 6.45 (d, 1H, J=587.4 Hz), 5.87 (ddt, 1H, J=16.8, 10.2, 6.4 Hz), 5.19-5.13 (m, 1H), 5.08 (dq, 1H, J=17.2, 1.7 Hz), 4.98 (ddt, 1.3 Hz, 1H, J=10.2, 2.3), 4.88 (ddd, 1H, J=11.1, 6.2, 5.1 Hz), 4.23-4.12 (m, 2H), 3.84 (dt, 1H, J=6.3, 4.4 Hz), 3.69 (dd, 1H, J=11.8, 4.7 Hz), 3.63 (dd, 1H, J=11.8, 4.3 Hz), 2.99 (q, 1.5H, J=7.3 Hz), 2.71-2.65 (m, 2H), 2.35 (dtd, 2H, J=7.3, 6.4, 1.6 Hz), 1.12 (t, 2.1H, J=7.3 Hz). $^{13}$C NMR (101 MHz, DMSO-$d_6$) δ 171.09, 152.01, 151.02, 149.57, 143.08, 137.09, 123.50, 115.48, 84.60 (d, J=2.9 Hz), 77.31 (d, J=4.5 Hz), 69.15, 61.38, 61.27 (d, J=5.3 Hz), 45.55, 35.54, 28.82, 8.62. $^{31}$P NMR (162 MHz, DMSO-$d_6$) δ 3.74. HRMS ESI ($C_{15}H_{20}N_5O_6P$) calculated 398.1229, found: 398.1230.

Synthesis of (2R,3R,4R,5R)-2-((bis(4-methoxyphenyl)(phenyl)methoxy)methyl)-4-fluoro-5-(6-(pent-4-enamido)-9H-purin-9-yl)tetrahydrofuran-3-yl(2-cyanoethyl) diisourouvluhosuhoramidite (13)

The synthesis of compound 13 from compound 10 was accomplished according to the synthetic scheme depicted below, and detailed in the following description.

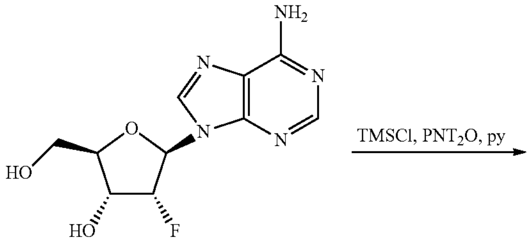

10

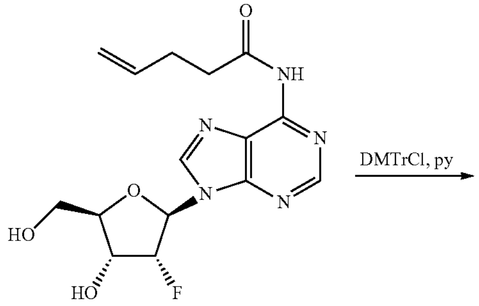

11

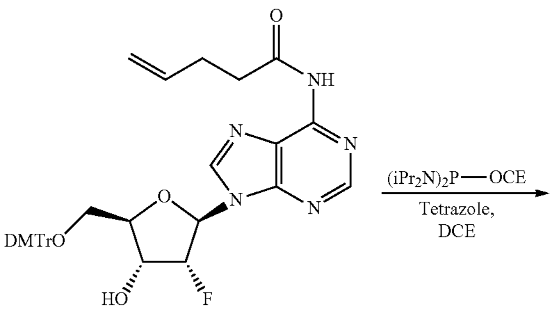

12

-continued

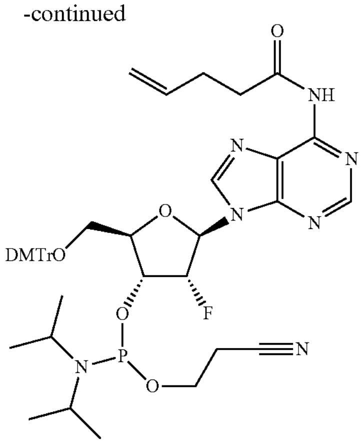

13

N-(9-42R,3R,4R,5R)-3-fluoro-4-hydroxy-5-(hydroxymethyptetrahydrofuran-2-yl)-9H-purin-6-yl) pent-4-enamide (11)

10 (1 g, 3.7 mmol, CAS: 64183-27-3, Chemgenes corp.) was azeotroped with pyridine (2×10 mL), dissolved in pyridine (15 mL), and TMSCl (2.36 mL, 18.6 mmol) was added dropwise. After stirring the reaction mixture at ambient temperature for 1 hour, pentenoic anhydride (1.7 mL, 9.3 mmol) was added dropwise and stirring was continued for further 12 hours. TEA (1 mL) was added, and, after cooling to 0° C., water (4 mL) was added and stirring was continued for 5 minutes. Then aqueous ammonia was added (32%, 4 mL), while still at 0° C. and stirring was continued for another 30 minutes. Volatiles were quickly evaporated at 30° C. and the residue was passed through a plug of silica in DCM-MeOH 19:1 affording product (1.1 g) of ca 90% purity, suitable for next reaction. ESI MS m/z (%): 352.1 (100) [M+H].

N-(9-((2R,3R,4R,5R)-5-((bis(4-methoxyphenyl) (phenyOmethoxy)methyl)-3-fluoro-4-hydroxytetrahydrofuran-2-yl)-9H-purin-6-yl)pent-4-enamide (12)

Partially protected nucleoside 11 (1.09 g, 3.1 mmol) was azeotroped with pyridine (2×10 mL), dissolved in pyridine (15 mL) and DMTrCl (1.15 g, 3.4 mmol) was added at 0° C. in five portions. Reaction mixture was stirred at ambient temperature for 12 hours, after which all volatiles were evaporated. Residue was dissolved in small volume of DCM and applied to a preconditioned silicagel column (10% acetone in cyclohexane, 1% TEA), and flash chromatography (10-80% acetone in cyclohexane) afforded 12 (1.7 g). $^{1}$H NMR (400 MHz, DMSO-$d_6$) δ 10.76 (s, 1H), 8.64 (s, 1H), 8.60 (s, 1H), 7.32-7.28 (m, 2H), 7.24-7.14 (m, 7H), 6.82-6.75 (m, 4H), 6.40 (dd, 1H, J=20.0, 1.5 Hz), 5.87 (ddt, 1H, J=16.8, 10.2, 6.4 Hz), 5.75 (d, 1H, J=6.9 Hz), 5.65 (ddd, 1H, J=52.7, 4.5, 1.4 Hz), 5.08 (dq, 1H, J=17.2, 1.7 Hz), 4.98 (ddt, 1H, J=10.2, 2.2, 1.4 Hz), 4.84 (dddd, 1H, J=23.2, 8.3, 6.9, 4.5 Hz), 4.12 (ddd, 1H, J=8.0, 5.1, 2.4 Hz), 3.71 (s, 6H), 3.28 (dd, 1H, J=10.7, 2.5 Hz), 3.22 (dd, 1H, J=10.8, 5.3 Hz), 2.68 (t, 2H, J=7.4 Hz), 2.35 (dtt, 2H, J=8.7, 7.4, 1.5 Hz). $^{13}$C NMR (101 MHz, DMSO-$d_6$) δ 171.05, 158.20, 151.99, 151.29, 149.90, 144.91, 143.24, 137.65, 135.63, 135.60, 129.82, 127.90, 127.81, 126.79, 123.83, 115.47, 113.27, 93.48 (d, J=184.6 Hz), 86.83 (d, J=34.7 Hz), 85.55, 81.59, 68.85 (d, J=16.5 Hz) 62.77, 55.17, 35.56, 28.78. $^{19}$F NMR (377 MHz, DMSO-$d_6$) δ-201.20 (ddd, J=52.9, 23.2, 20.1 Hz). HRMS ESI ($C_{36}H_{36}FN_5O_6$) calculated 654.2728, found: 654.2726.

(2R,3R,4R,5R)-2-((bis(4-methoxyphenyl)(phenyl) methoxy)methyl)-4-fluoro-5-(6-(pent-4-enamido)-9H-purin-9-yl)tetrahydrofuran-3-yl (2-cyanoethyl) diisopropylphosphoramidite (13)

To a solution of 12 (688 mg, 1.05 mmol) in DCE (11 mL) under argon atmosphere was via syringe added 2-cyanoethyl N,N,N',N'-tetraisopropylphosphorodiamidite (0.67 mL, 2.1 mmol) followed by tetrazole (0.45M in ACN, 5.85 mL, 2.63 mmol). Reactio mixture was stirred at ambient temperature for 30 minutes, diluted with DCM (150 mL), washed with sat. aq. $NaHCO_3$ (50 mL), dried over sodium sulfate and evaporated. Crude product was dissolved in DCM (2 mL) and applied to a preconditioned (10% acetone in cyclohexane, 1% TEA) silicagel column and eluted with a gradient of acetone in cyclohexane 10-60%. Product was freeze-dried from benzene to afford 13 (700 mg) as a 3:2 mixture of diastereomers. $^{31}$P NMR (162 MHz, Benzene-$d_6$) δ 151.69, 151.66. $^{19}$F NMR (377 MHz, Benzene-$d_6$) δ-198.55 (dt, J=51.2, 17.7 Hz), −198.96 (ddd, J=51.1, 21.6, 15.6 Hz).

Synthesis of (1R,2R,5R)-2-(6-benzamido-9H-purin-9-0-5-((bis(4-methoxyphenyl)(phenyl)methoxy) methyl)cyclopent-3-en-1-yl(2-cyanoethyl) diisopropylphosphoramidite (19)

The synthesis of compound 19 from compound 14 was accomplished according to the synthetic scheme depicted below, and detailed in the following description.

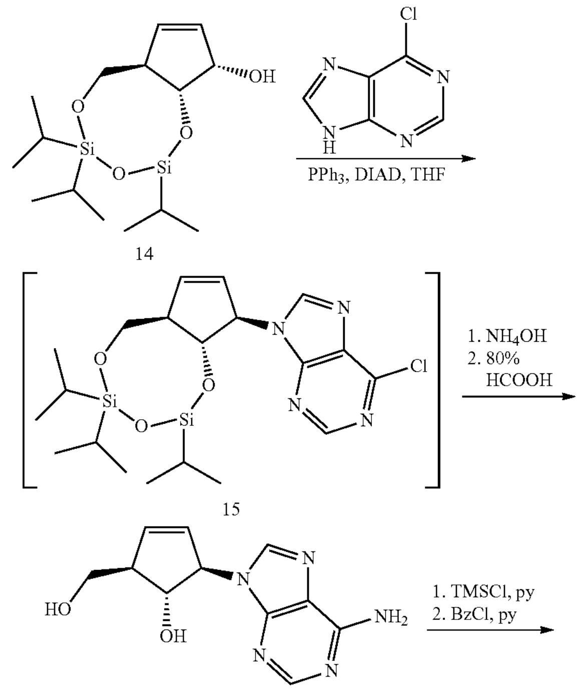

14

15

16

-continued

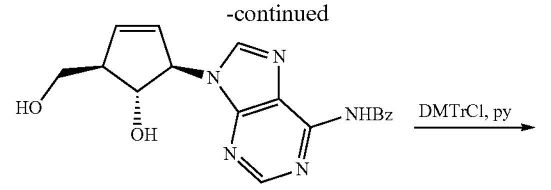

17

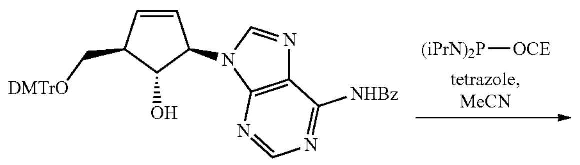

18

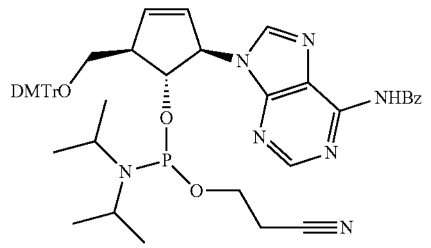

19

6-chloro-9-((6aR,9R,9aR)-2,2,4,4-tetraisopropyl-6,6a,9,9a-tetrahydrocyclopenta[f][13,5,2,4]trioxadisilocin-9-yl)-9H-purine (15)

Mixture of starting material 14 (2.43 g, 6.52 mmol, *J. Org. Chem*, 2014, 79, 3917), 6-chlorpurine (1.51 g, 9.78 mmol), triphenylphospine (3.42 g, 13.0 mmol) in THF (85 mL) was cooled to −10° C. and DIAD (2.61 ml, 13.0 mmol) was added dropwise during 5 minutes. Reaction mixture was allowed to reach 0° C. during 15 minutes and then kept at this temperature for another 2 hours. Volatiles were evaporated and the the product was purified by flash chromatography on silica (cyclohexane: ethyl acetate 5→40%). Product of the reaction (1.85 g) was a mixture of two inseparable isomers and was used in the next reaction without further purification. ESI MS m/z (%): 509.2 (100) [M+H].

(1R,2R,5R)-2-(6-amino-9H-purin-9-yl)-5-(hydroxymethyl)cyclopent-3-en-1-ol (16)

Protected nucleoside 15 (1.85 g, 3.64 mmol) was dissolved in mixture of ethanolic ammonia (44 mL, 4 M) and dioxane (28 mL). Reaction mixture was heated to 90° C. for 48 hours, evaporated and co-evaporated with ethanol (2×150 mL). To the residue was added aq. HCOOH (75 ml, 80%) and reaction mixture was heated to 65° C. for 21 hours. Volatiles were evaporated and the residue was azeotroped with ethanol (3×100 mL). Then a mixture of ethanol (50 mL) and aq. $NH_3$ (25 mL, 25%) was added and the solution was stirred for 90 minutes, evaporated and azeotroped with ethanol (3×100 mL). 16 (578 mg) was isolated by column chromatography on silica (ethyl acetate→ethyl acetate:acetone:ethanol:water 36:6:5:3). $^1$H NMR (400 MHz, DMSO-$d_6$) δ 8.14 (s, 1H), 8.07 (s, 1H), 7.25 (s, 2H), 6.04 (dt, J=6.1, 2.1 Hz, 1H), 5.80 (dt, J=6.1, 2.1 Hz, 1H), 5.49 (br s, 1H), 5.34 (dq, J=6.0, 2.1 Hz, 1H), 4.74 (br s, 1H), 4.22 (t, J=5.7 Hz, 1H), 3.63 (dd, J=10.6, 4.6 Hz, 1H), 3.49 (dd, J=10.6, 6.3 Hz, 1H), 2.67 (ddm, J=6.5, 4.5 Hz, 1H). $^{13}$C NMR (101 MHz, DMSO-$d_6$) δ 156.05, 152.84, 149.75, 139.42, 135.92, 128.47, 119.16, 80.06, 67.54, 61.91, 57.13. HRMS ESI ($C_{11}H_{13}N_5O_2$) calculated 248.1148, found: 248.1144.

N-(94(1R,4R,5R)-5-hydroxy-4-(hydroxymethyl)cyclopent-2-en-1-yl)-9H-purin-6-yl)benzamide (17)

16 (196 mg, 0.79 mmol) was azeotroped with pyridine (2×15 mL), then dissolved in pyridine (10 mL), cooled to 0° C. and then TMSCl (0.76 mL, 5.9 mmol) was added dropwise during 2 minutes. Reaction mixture was stirred at 0° C. for 30 minutes and then at r.t. for 1 hour. After cooling it down to 0° C., benzoyl chloride (0.2 mL, 1.7 mmol) was slowly added and the resulting solution was left at 0° C. for 1 h and then overnight at ambient temperature. The reaction mixture was then cooled to 0° C. again, quenched with water (0.6 mL), and, after 15 minutes, aq. ammonia (1.6 mL, 25%) was added. After further 15 minutes at 0° C. the reaction mixture was evaporated to dryness. Residue was extracted with ethyl acetate-ethanol mixture (50 ml, 2:1) and solids were filtered-off on a celite pad. Product was purified on silica (ethyl acetate→ethyl acetate:acetone:ethanol:water 100:15:6:4) to afford 218 mg of compound 17. $^1$H NMR (400 MHz, DMSO-$d_6$) δ 11.16 (s, 1H), 8.71 (s, 1H), 8.39 (s, 1H), 8.19-7.86 (m, 2H), 7.68-7.59 (m, 1H), 7.59-7.50 (m, 2H), 6.09 (dt, J=6.1, 2.1 Hz, 1H), 5.84 (dt, J=6.1, 2.1 Hz, 1H), 5.54 (br s, 1H), 5.49 (dq, J=6.0, 2.1 Hz, 1H), 4.76 (br s, 1H), 4.30-4.25 (m, 1H), 3.70-3.62 (m, 1H), 3.55-3.48 (m, 1H), 2.74-2.65 (m, 1H). $^{13}$C NMR (101 MHz, DMSO-$d_6$) δ 165.98, 152.57, 151.45, 150.83, 143.08, 136.33, 134.52, 132.41, 128.63, 128.58, 128.18, 125.34, 80.04, 67.84, 61.85, 55.21. HRMS ESI ($C_{18}H_{17}N_5O_3$) calculated 352.1410, found: 352.1411.

N-(9-41R,4R,5R)-4-((bis(4-methoxyphenyl)(phenyl)methoxy)methyl)-5-hydroxycyclopent-2-en-1-yl)-9H-purin-6-yl)benzamide (18)

17 (360 mg, 1.03 mmol) was azeotroped with pyridine (3×15 mL), dissolved in pyridine (15 mL), cooled to 0° C. and DMTrCl (382 mg, 1.13 mmol) was added in one portion at 0° C. Reaction mixture was allowed to warm to ambient temperature and stirred for 20 h, after which it was cooled to 0° C. again and a second portion of DMTrCl (115 mg, 0.34 mmol). The reaction mixture was stirred at ambient temperature for another 16 h, then quenched with satd. aq. $NaHCO_3$ (4 mL) and evaporated. Residue was dissolved in ethyl acetate (200 mL) and washed with saturated aqueous solution of $NaHCO_3$ (2×100 mL) and brine (100 mL). Organic phase was dried over sodium sulfate and evaporated. Product was purified by chromatography (toluene: ethyl acetate 1:1 and then toluene:acetone 1:1) on a TEA-deactivated silica to afford 485 mg of 18. $^1$H NMR (400 MHz, DMSO-$d_6$) δ 11.14 (s, 1H), 8.68 (s, 1H), 8.37 (s, 1H), 8.09-8.02 (m, 2H), 7.69-7.60 (m, 1H), 7.59-7.51 (m, 2H), 7.45-7.38 (m, 2H), 7.36-7.14 (m, 7H), 6.94-6.85 (m, 4H), 6.15 (dt, J=6.1, 2.1 Hz, 1H), 5.92 (dt, J=6.1, 2.1 Hz, 1H), 5.57 (d, J=6.2 Hz, 1H), 5.49 (dq, J=6.4, 2.2 Hz, 1H), 4.40 (q, J=6.3 Hz, 1H), 3.74 (s, 6H), 3.26 (dd, J=8.9, 4.9 Hz, 1H), 3.11 (dd, J=8.9, 6.7 Hz, 1H), 2.94-2.86 (m, 1H). $^{13}$C NMR (101 MHz, DMSO) δ 165.72, 158.21, 152.72, 151.41, 150.34, 144.87, 143.45, 135.98, 135.91, 135.26, 132.55, 129.90, 128.62, 128.00, 127.89, 126.80, 126.10, 113.36, 84.80, 80.17, 67.87, 63.51, 55.19, 52.23, 46.75. HRMS ESI ($C_{39}H_{35}N_5O_5$) calculated 654.2716, found: 654.2712.

(1R,2R,5R)-2-(6-benzamido-9H-purin-9-yl)-5-((bis(4-methoxyphenyl)(phenyl)methoxy)methyl)cyclopent-3-en-1-yl (2-cyanoethyl) diisopropylphosphoramidite (19)

Compound 18 (465 mg, 0.71 mmol) was azeotroped with acetonitrile (3×15 mL), dissolved in DCE (10 mL) and the flask was backfilled with argon. 2-cyanoethyl N,N,N',N'-tetraisopropylphosphorodiamidite (0.45 mL, 1.42 mmol) followed by tetrazole (0.45M in acetonitrile, 3.95 mL, 1.78 mmol) were sequentially added to the solution was via syringe. Reaction mixture was stirred at r.t. for 1.5 hours, diluted with DCM (200 mL), washed with sat. aq. $NaHCO_3$ (100 mL), dried over sodium sulfate and evaporated. Product was isolated on a TEA-deactivated silica gel column (toluene:acetone 4:1). 19 (450 mg) was isolated as a mixture of diastereomers. $^{31}P$ NMR (162 MHz, d6-benzene) δ 152.24, 152.22.

Synthesis of (1R,6R,8R,9RJOR,13Z,15R,17R,18R)-8,17-bis(6-amino-9H-purin-9-yl)-9,18-difluoro-3,12-dihydroxy-2,4,7,11,16-pentaoxa-$3\lambda^5$,$12\lambda^5$-diphosphatricyclo[13.3.0.0$^{6,10}$]octadec-13-ene-3,12-dione (24)

The synthesis of compound 24 from compounds 6 and 20 was accomplished according to the synthetic scheme depicted below, and detailed in the following description.

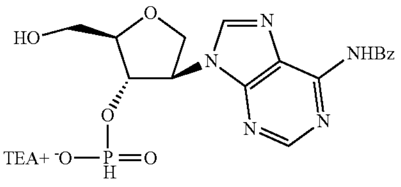

6

+

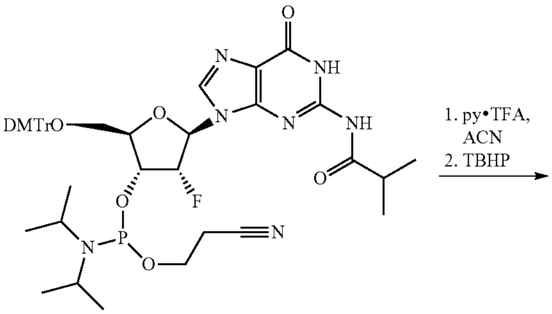

20

-continued

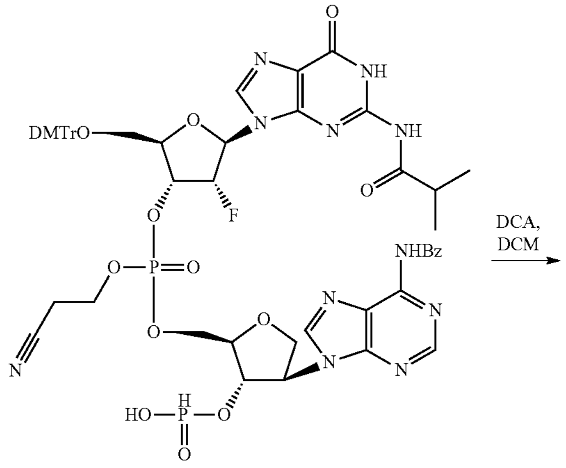

21

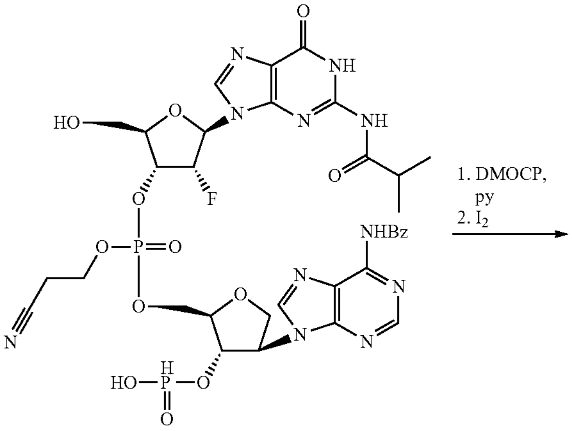

22

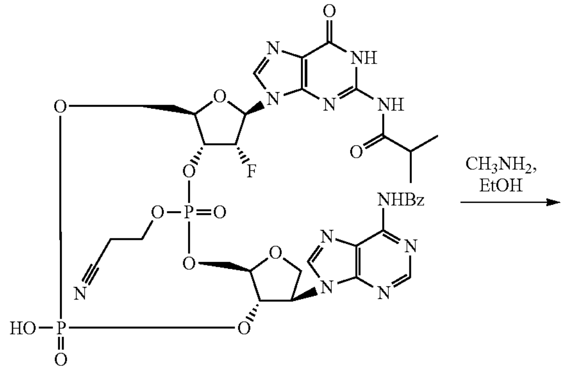

23

-continued

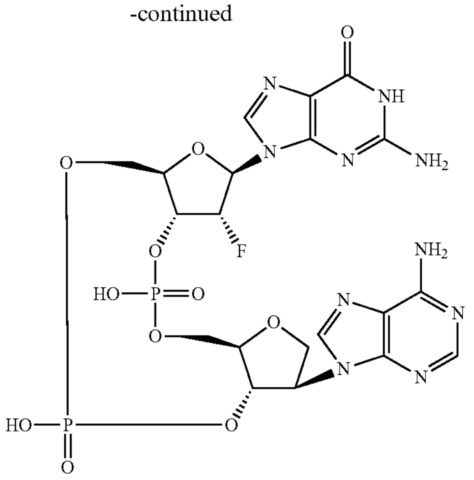

24

A mixture of 6 (41 mg, 0.077 mmol) and pyridinium trifluoroacetate (22 mg, 0.12 mmol) was codistilled with dry ACN (3x3 mL), suspended in dry ACN (1 mL) and stirred overnight in a sealed vessel over activated molecular sieves. In a separate flask, 20 (95 mg, 0.10 mmol, CAS: 144089-97-4, Sigma-Aldrich) was codistilled with dry ACN (3x3 mL), dissolved in dry ACN (1 mL) and stirred overnight in a sealed vessel over activated molecular sieves. A solution of phosphoramidite was transferred via syringe to the flask with the suspension of 6 with py-TFA and the resulting solution was stirred for 1 hour at ambient temperature. TBHP (5.5M solution in decane, 42 μL, 0.23 mmol) was added and the reaction mixture was stirred for further 30 minutes. Reaction mixture was quenched with NaHSO 3 (39% in water, 31 μL, 0.27 mmol), and evaporated to afford crude linear dimer 21, which was used in the next reaction without further purification. To a solution of crude 21 in DCM (3 mL) was added water (14 μL, 0.77 mmol) and a solution of DCA (57 μL, 0.7 mmol) in DCM (3 mL) dropwise. After stirring the reaction mixture for 30 minutes, TES (1.2 mL) was added and the reaction mixture was stirred for further 90 minutes, after which it was quenched by the addition of pyridine (1.2 mL). All solids were removed by filtration and thoroughly washed with pyridine. Volatiles were evaporated and 22 (29 mg) was isolated on RP FCC (ACN in 0.05M $NH_4COOH$, 0-50%) as a mixture of diastereomers.

22 was azeotroped with pyridine (2x2 mL), dissolved in pyridine (2 mL), DMOCP (50 mg, 0.27 mmol) was added and the reaction mixture was stirred at ambient temperature for 1 hour. Water (46 μL, 2.54 mmol) followed by iodine (26 mg, 0.1 mmol) were added and the reaction mixture was stirred at ambient temperature for 10 minutes, after which it was quenched with $NaHSO_3$ (39% in water, 31 μL, 0.27 mmol) and evaporated to afford crude cyclic dimer 23, which was used in the next reaction without further purification.

$CH_3NH_2$ (33% in ethanol, 1 mL) was added to the crude 23 and the reaction mixture was stirred at ambient temperature for 3 hours. Volatiles were evaporated and the product was purified on a preparative HPLC (ACN in 0.1M TEAB, 0-30%). Appropriate fractions were pooled, evaporated, codistilled with water (3x5 mL) and methanol (3x5 mL), dissolved in water (1 mL) and slowly passed through a 1 mL column of Dowex 50 ($Na^+$ cycle). Freeze-drying the eluent afforded the sodium salt of 24 (9 mg).

Synthesis of (1S,6R,8R,9R10R,15R,18R)-8,18-bis (6-amino-9H-purin-9-yl)-9-fluoro-3,12-dihydroxy-2, 4,7,11,13,16-hexaoxa-3$\lambda^5$,12$\lambda^5$-diphosphatricyclo [13.3.0.0$^{6,10}$]octadecane-3,12-dione (28)

The synthesis of compound 28 from compounds 9 and 13 was accomplished according to the synthetic scheme depicted below, and detailed in the following description.

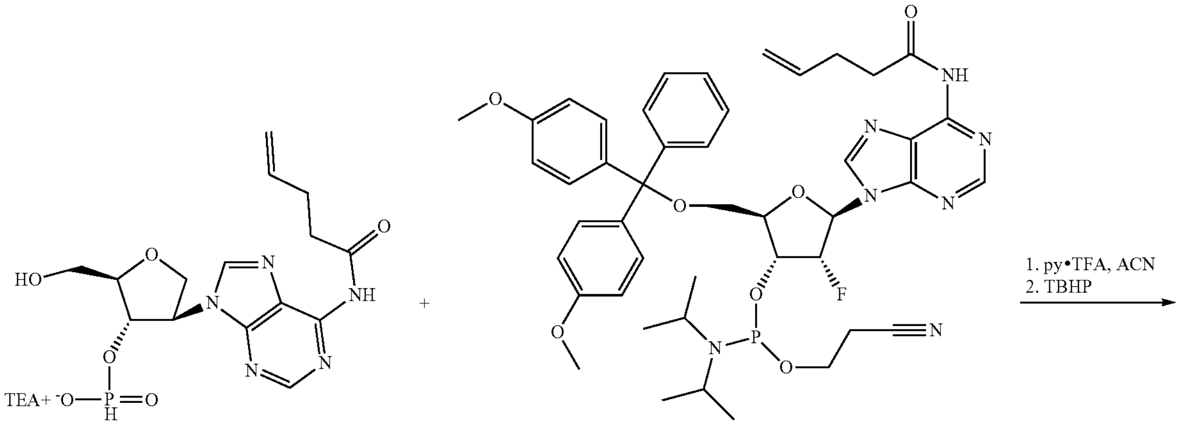

9

13

-continued
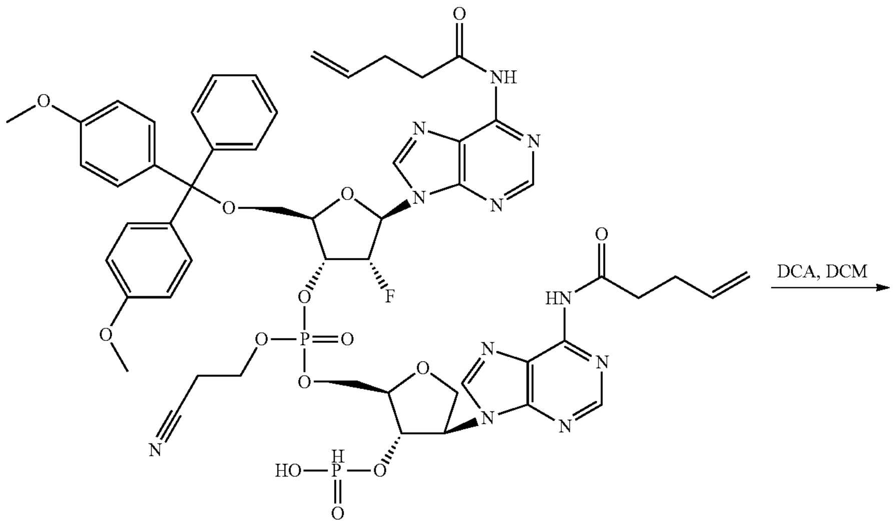
25
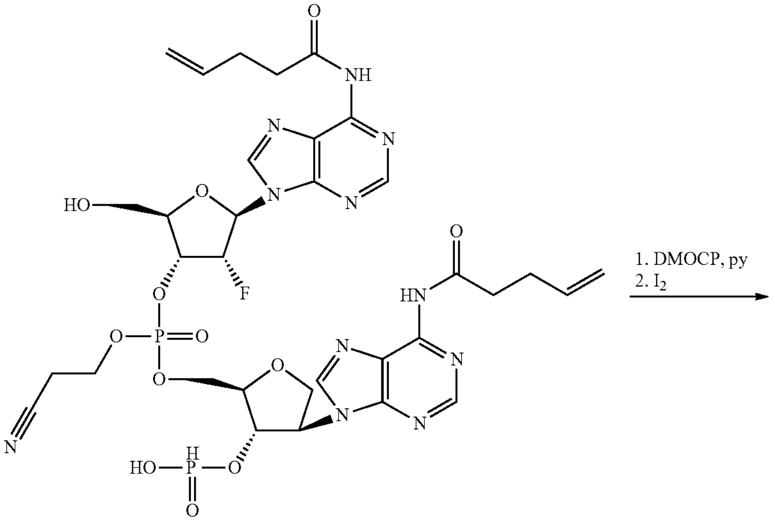
26
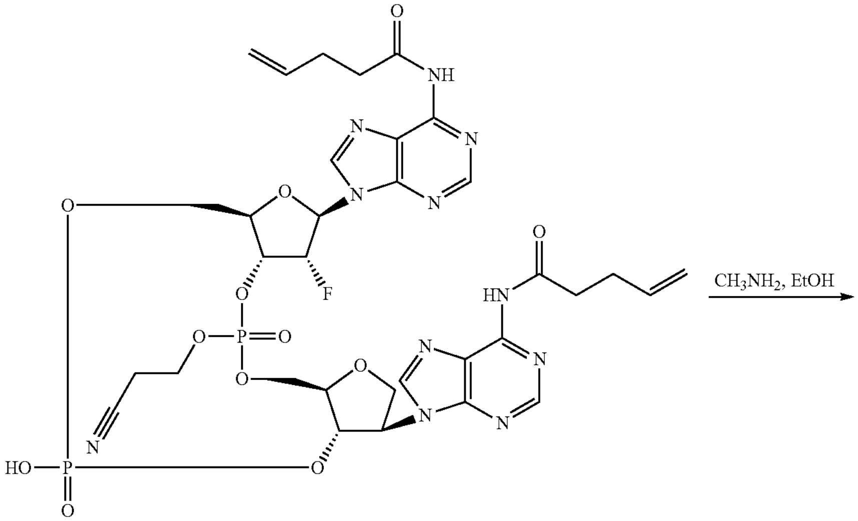
27

-continued

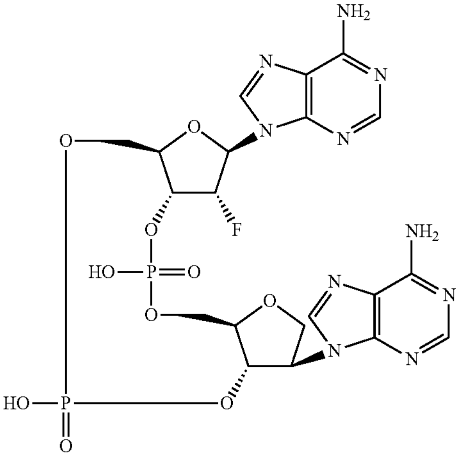

28

A mixture of 9 (105 mg, 0.21 mmol) and pyridinium trifluoroacetate (61 mg, 0.32 mmol) was codistilled with dry ACN (3x5 mL), suspended in dry ACN (5 mL) and stirred overnight in a sealed vessel over activated molecular sieves. In a separate flask, 13 (225 mg, 0.26 mmol) was codistilled with dry ACN (3x5 mL), dissolved in dry ACN (5 mL) and stirred overnight in a sealed vessel over activated molecular sieves. A solution of phosphoramidite was transferred via syringe to the flask with the suspension of 9 with py-TFA and the resulting solution was stirred for 1 hour at ambient temperature. TBHP (5.5M solution in decane, 115 μL, 0.63 mmol) was added and the reaction mixture was stirred for further 30 minutes. Reaction mixture was quenched with $NaHSO_3$ (39% in water, 152 μL, 0.57 mmol), and evaporated to afford crude linear dimer 25, which was used in the next reaction without further purification. To a solution of crude 25 in DCM (10 mL) was added water (28 μL, 2.1 mmol) and a solution of DCA (156 μL, 1.9 mmol) in DCM (10 mL) dropwise. After stirring the reaction mixture for 30 minutes, TES (1.2 mL) was added and the reaction mixture was stirred for further 90 minutes, after which it was quenched by the addition of pyridine (1.2 mL). All solids were removed by filtration and thoroughly washed with pyridine. Volatiles were evaporated and 26 (92 mg) was isolated on RP FCC (ACN in 0.05M $NH_4COOH$, 0-50%) as a mixture of diastereomers.

26 was azeotroped with pyridine (2x5 mL), dissolved in pyridine (5 mL), DMOCP (136 mg, 0.74 mmol) was added and the reaction mixture was stirred at ambient temperature for 1 hour. Water (125 μL, 7 mmol) followed by iodine (71 mg, 0.28 mmol) were added and the reaction mixture was stirred at ambient temperature for 10 minutes, after which it was quenched with $NaHSO_3$ (39% in water, 112 μL, 0.42 mmol) and evaporated to afford crude cyclic dimer 27, which was used in the next reaction without further purification.

$CH_3NH_2$ (33% in ethanol, 1 mL) was added to the crude 27 and the reaction mixture was stirred at ambient temperature for 3 hours. Volatiles were evaporated and the product was purified on a preparative HPLC (ACN in 0.1M TEAB, 0-30%). Appropriate fractions were pooled, evaporated, codistilled with water (3x5 mL) and methanol (3x5 mL), dissolved in water (1 mL) and slowly passed through a 1 mL column of Dowex 50 (Na t cycle). Freeze-drying the eluent afforded the sodium salt of 28 (36 mg).

Synthesis of (1R,6R,8R,9R10R,15R,18R)-8,18-bis (6-amino-9H-purin-9-yl)-9-fluoro-3,12-dihydroxy-2,4,7,11,13-pentaoxa-3$\lambda^5$,12$\lambda^5$-diphosphatricyclo [13.3.0.0$^{6,10}$]octadecane-3,12-dione (34)

The synthesis of compound 34 from compounds 29 and 19 was accomplished according to the synthetic scheme depicted below, and detailed in the following description.

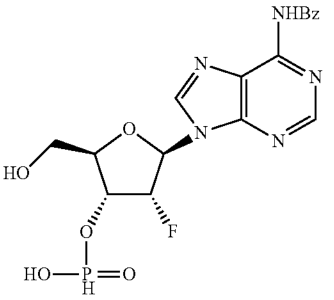

29

+

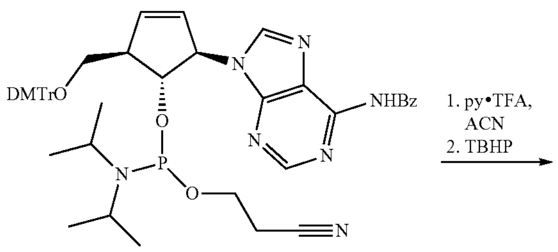

19

-continued

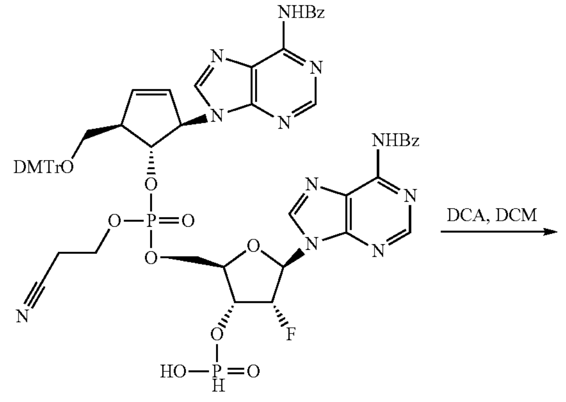

30

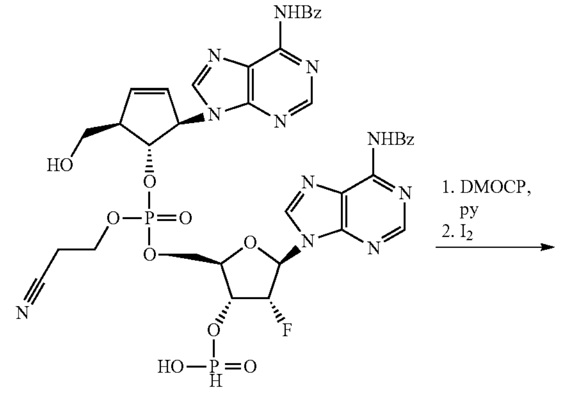

31

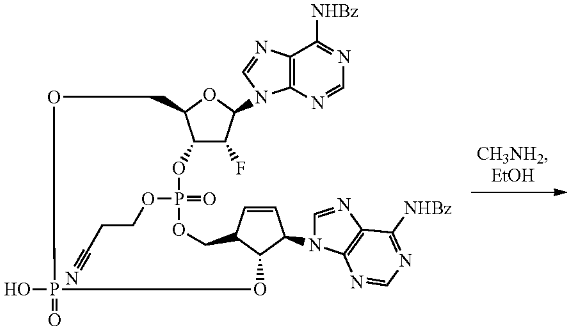

32

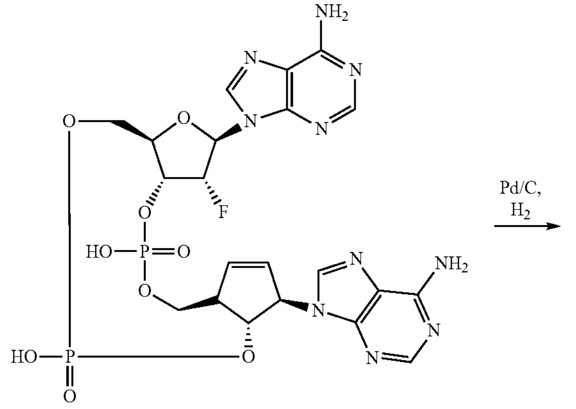

33

-continued

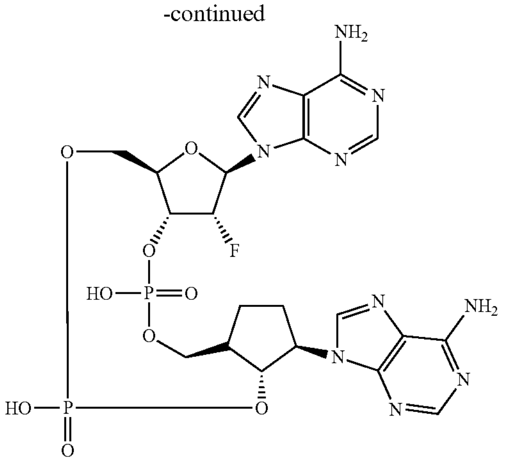

34

The following compounds were synthesized according to the protocols described above.

(1R,6R,8R,9R,10R,15R,18R)-8,18-bis(6-amino-9H-purin-9-yl)-9-fluoro-3,12-dihydroxy-2,4,7,11,13-pentaoxa-3$\lambda^5$,12$\lambda^5$-diphosphatricyclo[13.3.0.0$^{6,10}$]octadec-16-ene-3,12-dione (33)

A mixture of 29 (45 mg, 0.08 mmol, CAS: 1834500-64-9, Carbosynth Ltd.) and pyridinium trifluoroacetate (24 mg, 0.13 mmol) was codistilled with dry ACN (3×5 mL), suspended in dry ACN (5 mL) and stirred overnight in a sealed vessel over activated molecular sieves. In a separate flask, 19 (89 mg, 0.10 mmol) was codistilled with dry ACN (3×5 mL), dissolved in dry ACN (5 mL) and stirred overnight in a sealed vessel over activated molecular sieves. A solution of phosphoramidite was transferred via syringe to the flask with the suspension of 29 with py-TFA and the resulting solution was stirred for 1 hour at ambient temperature. TBHP (5.5M solution in decane, 46 μL, 0.25 mmol) was added and the reaction mixture was stirred for further 30 minutes. Reaction mixture was quenched with $NaHSO_3$ (39% in water, 33 μL, 0.17 mmol), and evaporated to afford crude linear dimer 30, which was used in the next reaction without further purification. To a solution of crude 30 in DCM (10 mL) was added water (15 μL, 0.84 mmol) and a solution of DCA (62 μL, 0.75 mmol) in DCM (5 mL) dropwise. After stirring the reaction mixture for 30 minutes, TES (1.3 mL) was added and the reaction mixture was stirred for further 90 minutes, after which it was quenched by the addition of pyridine (1.3 mL). All solids were removed by filtration and thoroughly washed with pyridine. Volatiles were evaporated and 31 was isolated on RP FCC (ACN in 0.05M $NH_4$ COOH, 0-50%) as a mixture of diastereomers.

31 was azeotroped with pyridine (2×5 mL), dissolved in pyridine (5 mL), DMOCP (54 mg, 0.29 mmol) was added and the reaction mixture was stirred at ambient temperature for 1 hour. Water (50 μL, 2.76 mmol) followed by iodine (28 mg, 0.11 mmol) were added and the reaction mixture was stirred at ambient temperature for 10 minutes, after which it was quenched with $NaHSO_3$ (39% in water, 33 μL, 0.17 mmol) and evaporated to afford crude cyclic dimer 32, which was used in the next reaction without further purification.

$CH_3NH_2$ (33% in ethanol, 1 mL) was added to the crude 32 and the reaction mixture was stirred at ambient temperature for 3 hours. Volatiles were evaporated and the product was purified on a preparative HPLC (ACN in 0.1M TEAB, 0-30%). Appropriate fractions were pooled, evaporated, codistilled with water (3×5 mL) and methanol (3×5 mL), dissolved in water (1 mL) and slowly passed through a 1 mL column of Dowex 50 ($Na^+$ cycle). Freeze-drying the eluent afforded the sodium salt of 33 (12 mg). HPLC retention time (HILIC, min): 4.10. $^1$H NMR (501 MHz, $D_2O$) δ 8.22 (s, 1H), 8.15 (s, 1H), 8.07 (s, 1H), 7.99 (s, 1H), 6.44 (dd, J=16.7 Hz, 1H), 6.03 (dtd, J=6.1, 2.2, 0.9 Hz, 1H), 5.75 (dt, J=6.1, 2.2 Hz, 1H), 5.71 (dq, J=5.8, 2.2, 1.8 Hz, 1H), 5.42 (dd, J=51.6, 4.1, 1H), 5.28 (dt, J=7.6, 6.1 Hz, 1H), 4.89 (dddd, J=23.5, 9.2, 8.2, 4.1 Hz, 1H), 4.47 (dm, J=9.2, 1H), 4.33 (ddd, J=12.2, 2.5, 1.2 Hz, 1H), 4.19 (ddd, J=10.4, 4.2, 1.8 1H), 4.14 (ddd, J=12.2, 3.7, 1.6 1H), 4.10 (dt, J=10.4, 3.4 Hz, 1H). $^{13}$C NMR (101 MHz, $D_2O$) δ 158.27, 158.00, 155.48, 154.52, 151.94, 150.56, 145.00, 141.51, 136.64, 131.69, 121.74, 121.54, 94.98 (d, J=189.6 Hz), 90.03 (d, J=34.2 Hz), 84.22 (d, J=6.1 Hz), 82.46 (t, J=5.3 Hz), 71.78 (dd, J=16.2, 5.3 Hz), 70.55 (d, J=2.4 Hz), 67.21 (d, J=4.5 Hz), 64.51 (d, J=4.8 Hz), 54.16 (t, J=6.5 Hz). $^{31}$H NMR (202.4 MHz, $H_2O$) δ −0.26, −0.98. $^{19}$F NMR (470.4 MHz, $H_2O$) δ-197.25. ESI MS m/z (%): 639.3 (100) [M−H].

(1R,6R,8R,9R,10R,15R,18R)-8,18-bis(6-amino-9H-purin-9-yl)-9-fluoro-3,12-dihydroxy-2,4,7,11,13-pentaoxa-3λ$^5$,12λ$^5$-diphosphatricyclo[13.3.0.0$^{6,10}$]octadecane-3,12-dione (34)

To a solution of 33 (5 mg) in methanol (1 mL) was added Pd/C (10%, 3 mg) and reaction mixture was treated with hydrogen (steel bomb, 15 bar) for 48 hours. Catalyst was filtered off on a syringe filter and product was purified on HPLC (0-25% of CAN in 0.1 M aq TEAB). Appropriate fractions were pooled, evaporated, codistilled with water (3×5 mL) and methanol (3×5 mL), dissolved in water (1 mL) and slowly passed through a 1 mL column of Dowex 50 ($Na^+$ cycle). Freeze-drying the eluent afforded the sodium salt of 34 (2 mg).

TABLE 1

Exemplary compounds and characterization data

| Compound | Structure / Name | Mass $[M - H]^-$ |
| --- | --- | --- |
| 28 | 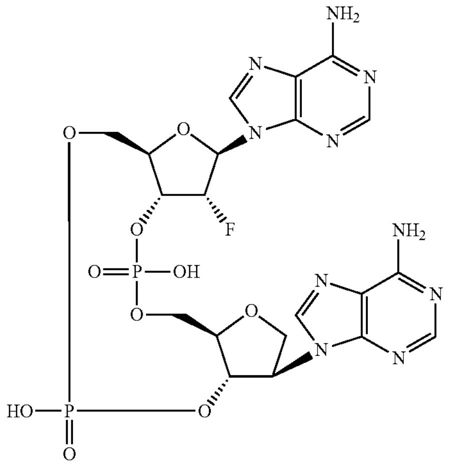 (1S,6R,8R,9R,10R,15R,18R)-8,18-bis(6-amino-9H-purin-9-yl)-9-fluoro-3,12-dihydroxy-2,4,7,11,13,16-hexaoxa-3λ$^5$,12λ$^5$-diphosphatricyclo[13.3.0.0$^{6,10}$]octadecane-3,12-dione | 643.4 |
| 28: HPLC retention time (HILIC, min): 3.78. $^1$H NMR (501 MHz, $D_2O$) δ 8.16 (s, 1H), 8.10 (s, 1H), 8.10 (s, 1H), 8.05 (s, 1H), 6.34 (d, 1H, J = 16.5 Hz), 5.53 (dd, 1H, J = 51.4, 4.0 Hz), 5.39 (dt, 1H, J = 6.9, 3.8 Hz), 5.29 (td, 1H, J = 7.1, 3.7 Hz), 4.92 (dtd, 1H, J = 21.1, 9.6, 4.0 Hz), 4.51 (ddd, 1H, J = 9.4, 2.0, 1.4 Hz), 4.40 (dd, 1H, J = 12.1, 2.0 Hz), 4.37 (dd, 1H, J = 10.5, 6.9 Hz), 4.35 (dd, 1H, J = 11.7, 2.3 Hz), 4.23 (dq, 1H, J = 7.1, 2.3 Hz), 4.20 (ddd, 1H, J = 11.7, 5.2, 2.0 Hz), 4.10 (ddd, 1H, J = 12.1, 4.2, 1.4 Hz), 4.10 (dd, 1H, J = 10.5, 3.9 Hz). $^{13}$C NMR (101 MHz, $D_2O$) δ 157.97, 157.97, 155.36, 154.96, 151.48, 150.21, 143.55, 141.55, 121.36, 121.01, 94.78 (d, J = 189.2 Hz), 90.27 (d, J = 34.0 Hz), 85.05 (t, J = 10.2 Hz), 82.44 (t, J = 11.3 Hz), 80.39 (d, J = 5.5 Hz), 74.44, 72.03 (dd, J = 16.4, 5.5 Hz), 65.67 (d, J = 4.4 Hz), 64.58 (d, J = 4.7 Hz), 64.31. $^{31}$P NMR (202.4 MHz, $D_2O$) δ −0.89, −0.69. $^{19}$F NMR (470.4 MHz, $D_2O$) δ −198.17. | | |

TABLE 1-continued

| Exemplary compounds and characterization data | | |
|---|---|---|
| Compound | Structure / Name | Mass [M − H]⁻ |
| 24 | 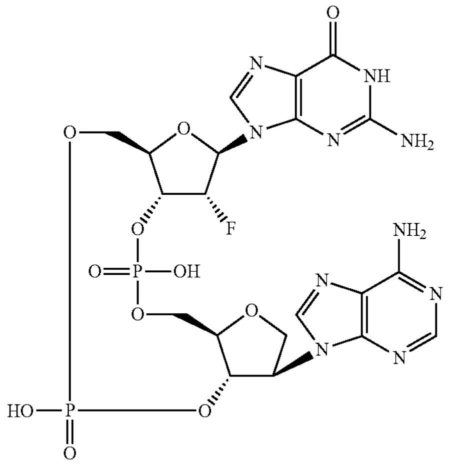 [SMILES: Nc1nc2c(ncn2[C@@H]2O[C@@H]3COP(=O)(O)O[C@H]4[C@H](n5cnc6c(N)ncnc65)CO[C@@H]4COP(=O)(O)O[C@H]3[C@H]2F)c(=O)[nH]1] (1S,6R,8R,9R,10R,15R,18R)-8-(2-amino-6-oxo-6,9-dihydro-1H-purin-9-yl)-18-(6-amino-9H-purin-9-yl)-9-fluoro-3,12-dihydroxy-2,4,7,11,13,16-hexaoxa-3$\lambda^5$,12$\lambda^5$-diphosphatricyclo[13.3.0.0$^{6,10}$]octadecane-3,12-dione<br>24: HPLC retention time (HILIC, min): 4.18. $^1$H NMR (400 MHz, $D_2O$) δ 8.19 (s, 1H), 8.10 (s, 1H), 7.71 (s, 1H), 6.12 (d, J = 18.1 Hz, 1H), 5.57 (dd, J = 51.6, 4.2 Hz, 1H), 5.39 (dt, J = 6.8, 3.4 Hz, 1H), 5.18 (td, J = 7.1, 3.5 Hz, 1H), 4.99 (m, 1H), 4.45 (dm, J = 9.0 Hz, 1H), 4.39 (dd, J = 10.5, 6.8 Hz, 1H), 4.36 (bdd, J = 12.0, 2.5 Hz, 1H), 4.35 (bdd, J = 12.0, 1.7 Hz, 1H), 4.22 (dq, J = 7.0, 2.3 Hz, 1H), 4.20 (ddd, J = 12.0, 5.1, 2.1 Hz, 1H), 4.17 (bdd, J = 10.5, 3.3 Hz, 1H), 4.07 (ddd, J = 12.0, 4.0, 1.5 Hz, 1H). $^{13}$C NMR (101 MHz, $D_2O$) δ 160.55, 157.81, 156.27, 154.61, 152.71, 151.37, 143.38, 139.09, 120.80, 119.04, 94.83 (d, J = 188.5 Hz), 90.60 (d, J = 34.7 Hz), 84.97 (t, J = 10.1 Hz), 82.57 (t, J = 10.8 Hz), 80.88, 74.56, 72.15 (dd, J = 16.1, 5.1 Hz), 65.57 (d, J = 4.8 Hz), 64.64 (d, J = 4.8 Hz), 64.08. $^{31}$P NMR (162 MHz, $D_2O$) δ −0.56, −0.65. $^{19}$F NMR (376 MHz, $D_2O$) δ −197.54. | 659.4 |
| 34 | 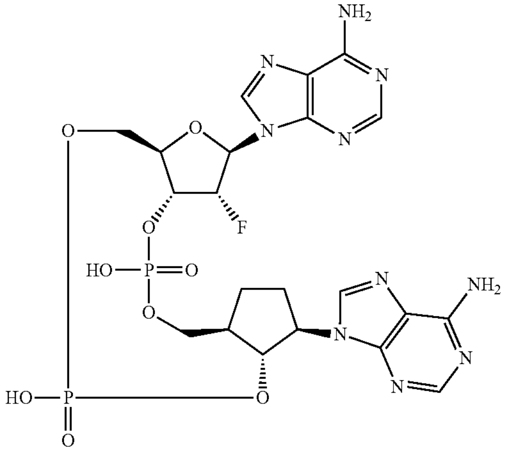 [SMILES: Nc1ncnc2c1ncn2[C@@H]1CC[C@@H]2COP(=O)(O)O[C@H]3[C@@H](F)[C@H](n4cnc5c(N)ncnc54)O[C@@H]3COP(=O)(O)O[C@H]21] (1R,6R,8R,9R,10R,15R,18R)-8,18-bis(6-amino-9H-purin-9-yl)-9-fluoro-3,12-dihydroxy-2,4,7,11,13-pentaoxa-3$\lambda^5$,12$\lambda^5$-diphosphatricyclo[13.3.0.0$^{6,10}$]octadecane-3,12-dione<br>34: HPLC retention time (C18, min): 2.23. $^1$H NMR (501 MHz, $D_2O$) δ 8.22 (s, 1H), 8.22 (s, 1H), 8.22 (s, 1H), 8.09 (s, 1H), 6.40 (d, 1H, J = 17.0 Hz), 5.45 (dd, 1H, J = 51.9, 4.2 Hz), 5.02 - 4.91 (m, 3H), 4.48 (dq, 1H, J = 9.2, 2.2 Hz), 4.31 (dt, 1H, J = 12.0, 2.2 Hz), 4.14 (ddd, 1H, J = 12.1, 3.4, 1.7 Hz), 4.06 (dt, 1H, J = 10.2, 2.7 Hz), 4.02 (ddd, 1H, J = 10.2, 3.5, 2.0 Hz), 2.48 (m, 1H), 2.33 (ddt, 1H, J = 13.3, 8.8, 7.4 Hz), 2.17 (dtd, 1H, J = 13.4, 8.8, 7.1 Hz), 2.04 - 1.98 (m, 2H). $^{13}$C NMR (101 MHz, $D_2O$) δ 156.27, 156.11, 153.45, 152.66, 150.10, 148.66, 142.41, 139.92, 119.63, 119.51, 93.06 (d, J = 189.0 Hz), 87.68 (d, J = 34.1 Hz), 80.15 (t, J = 10.1 Hz), 79.85 (d, J = 6.6 Hz), 69.88 (dd, J = 16.0, 5.0 Hz), 64.90 (d, J = 5.4 Hz), 62.52, 62.42 (d, J = 4.8 Hz), 44.53 (dd, J = 11.0, 6.1 Hz), 27.87, 22.27. $^{31}$P NMR (202.4 MHz, $D_2O$) δ 2.05, 0.66. $^{19}$F NMR (470.4 MHz, $D_2O$) δ −201.22 (ddd, J = 52.0, 23.6, 17.0 Hz). | 641.4 |

TABLE 1-continued

| Compound | Structure / Name | Mass [M − H]⁻ |
|---|---|---|
| 50 | 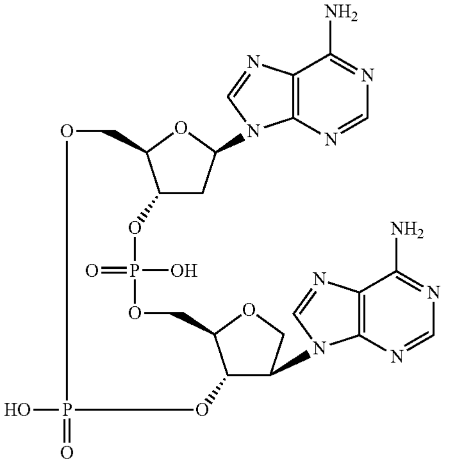 (1S,6R,8R,10S,15R,18R)-8,18-bis(6-amino-9H-purin-9-yl)-3,12-dihydroxy-2,4,7,11,13,16-hexaoxa-3λ$^5$,12λ$^5$-diphosphatricyclo[13.3.0.0$^{6,10}$]octadecane-3,12-dione | 625.4 |
| 51 | 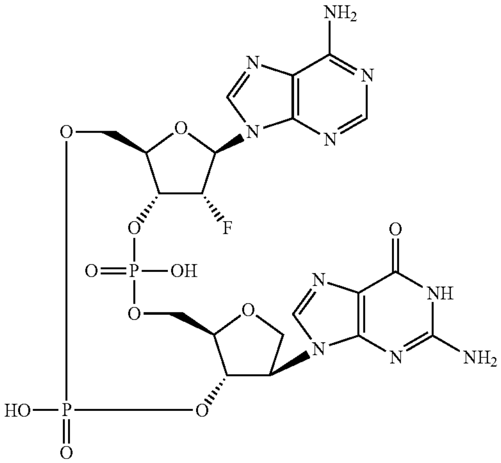 [SMILES: Nc1nc2c(ncn2[C@@H]2CO[C@@H]3COP(=O)(O)O[C@H]4[C@@H](F)[C@H](n5cnc6c(N)ncnc65)O[C@@H]4COP(=O)(O)O[C@@H]23)c(=O)[nH]1] (1S,6R,8R,9R,10R,15R,18R)-18-(2-amino-6-oxo-6,9-dihydro-1H-purin-9-yl)-8-(6-amino-9H-purin-9-yl)-9-fluoro-3,12-dihydroxy-2,4,7,11,13,16-hexaoxa-3λ$^5$,12λ$^5$-diphosphatricyclo[13.3.0.0$^{6,10}$]octadecane-3,12-dione | 659.4 |

50: HPLC retention time (HILIC, min): 4.20. $^1$H NMR (400 MHz, $D_2O$) δ 8.25 (s, 1H), 8.19 (s, 1H), 8.15 (s, 1H), 8.10 (s, 1H), 6.48 (dd, J = 7.1, 3.8 Hz, 1H), 5.37 (dt, J = 7.1, 4.1 Hz, 1H), 5.25 (td, J = 7.2, 4.1 Hz, 1H), 4.95 (p, J = 7.0 Hz, 1H), 4.40 (dd, J = 10.3, 7.1 Hz, 1H), 4.30 (ddd, J = 11.8, 2.6, 1.3 Hz, 1H), 4.27 (ddt, J = 6.6, 4.3, 2.2 Hz, 1H), 4.22 (dq, J = 7.0, 2.4 Hz, 1H), 4.39 (ddd, J = 11.7, 2.7, 2.0 Hz, 1H), 4.35 (dd, J = 10.4, 6.4 Hz, 1H), 4.25 (dq, J = 6.6, 2.3 Hz, 1H), 4.17 (dd, J = 10.3, 4.1 Hz, 1H), 4.15 (ddd, J = 11.8, 2.2, 1.7 Hz, 1H), 4.11 (ddd, J = 11.6, 4.3, 2.5 Hz, 1H), 4.04 (ddd, J = 11.6, 4.2, 2.4 Hz, 1H), 2.95 (ddd, J = 14.1, 7.3, 3.8 Hz, 1H), 2.78 (dt, J = 14.1, 7.2 Hz, 1H). $^{13}$C NMR (101 MHz, $D_2O$) δ 158.16, 158.11, 155.30, 155.11, 151.67, 150.80, 143.44, 142.18, 121.38, 121.15, 86.18, 85.34 (t, J = 10.3 Hz), 84.90 (t, J = 10.2, 8.6 Hz), 80.44 (d, J = 5.6 Hz), 74.16 (d, J = 5.1 Hz), 73.94, 65.37 (d, J = 4.9 Hz), 64.03 (d, J = 1.9 Hz), 64.01 (d, J = 5.0 Hz), 41.18. $^{31}$P NMR (162 MHz, $D_2O$) δ 0.08, −0.51.

51: HPLC retention time (HILIC, min): 4.24. $^1$H NMR (400 MHz, $D_2O$) δ 8.25 (s, 1H), 8.16 (s, 1H), 7.72 (s, 1H), 6.42 (d, J = 14.3 Hz, 1H), 6.12 (dt, J = 7.2, 5.8 Hz, 1H), 5.46 (dd, J = 51.5, 3.5 Hz, 1H), 5.20 (dt, J = 8.5, 5.8 Hz, 1H), 4.94 - 4.83 (m, 1H), 4.54 (dm, J = 9.8 Hz, 1H), 4.46 (dd, J = 12.3, 2.3 Hz, 1H), 4.35 (dd, J = 9.9, 8.5 Hz, 1H), 4.29 (dd, J = 11.5, 2.6 Hz, 1H), 4.25 - 4.20 (m, 1H), 4.16 - 4.06 (m, 2H), 3.98 (dd, J = 9.8, 6.0 Hz, 1H). $^{13}$C NMR (101 MHz, $D_2O$) δ 159.65, 156.24, 153.49, 152.93, 151.87, 148.25, 141.69, 139.02, 119.28, 117.57, 92.91 (d, J = 190.1 Hz), 88.05 (d, J = 32.8 Hz), 82.76 (t, J = 10.8 Hz), 80.32 (t, J = 11.1 Hz), 74.62 (d, J = 5.8 Hz), 72.15, 69.71 (dd, J = 16.2, 5.1 Hz), 64.14, 63.93 (d, J = 5.6 Hz), 62.43 (d, J = 4.8 Hz). $^{31}$P NMR (162 MHz, $D_2O$) δ 1.04, 0.81. $^{19}$F NMR (376 MHz, $D_2O$) δ −202.50 (ddd, J = 51.5, 23.9, 14.4 Hz).

TABLE 1-continued

Exemplary compounds and characterization data

| Compound | Structure / Name | Mass [M − H]⁻ |
| --- | --- | --- |
| 52 | 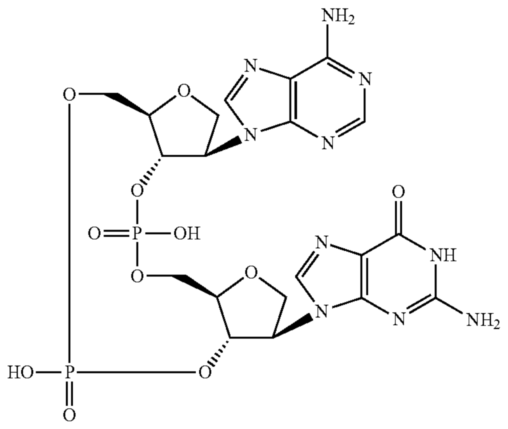 [SMILES: Nc1nc2c(ncn2[C@@H]2CO[C@@H]3COP(=O)(O)O[C@H]4[C@H](n5cnc6c(N)ncnc65)CO[C@@H]4COP(=O)(O)O[C@@H]23)c(=O)[nH]1] (1S,6R,9R,10S,15R,18R)-9-(2-amino-6-oxo-6,9-dihydro-1H-purin-9-yl)-18-(6-amino-9H-purin-9-yl)-3,12-dihydroxy-2,4,7,11,13,16-hexaoxa-3$\lambda^5$,12$\lambda^5$-diphosphatricyclo[13.3.0.0$^{6,10}$]octadecane-3,12-dione | 641.4 |
| 52: HPLC retention time (HILIC, min): 4.15. $^1$H NMR (400 MHz, $D_2O$) δ 8.24 (s, 1H), 8.06 (s, 1H), 7.71 (s, 1H), 5.78 (m, 1H), 5.38 (bd, J = 5.2 Hz, 1H), 5.20 - 5.13 (m, 2H), 4.40 - 4.32 (m, 3H), 4.26 (dd, J = 10.6, 5.1 Hz, 1H), 4.23 - 4.13 (m, 3H), 4.06 (ddd, J = 11.1, 4.0, 2.3 Hz, 1H), 3.93 (bd, J = 10.4 Hz, 1H), 3.89 (dd, J = 10.3, 5.3 Hz, 1H). $^{13}$C NMR (101 MHz, $D_2O$) δ 159.61, 156.19, 153.30, 153.02, 152.03, 149.50, 141.43, 140.54, 118.56, 117.08, 84.54 (t, J = 9.9 Hz), 83.34 (t, J = 11.4 Hz), 79.56 (d, J = 5.6 Hz), 76.34 (d, J = 5.3 Hz), 73.53, 72.34, 64.70, 63.53 (d, J = 5.1 Hz), 63.13 (d, J = 5.1 Hz), 61.98. $^{31}$P NMR (162 MHz, $D_2O$) δ 1.39, 1.14. | | |
| 53 | 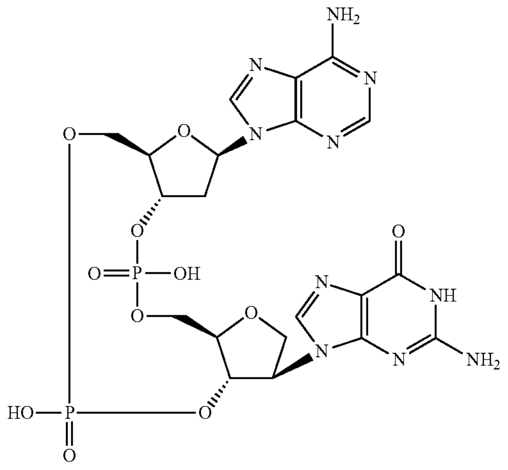 [SMILES: Nc1nc2c(ncn2[C@@H]2CO[C@@H]3COP(=O)(O)O[C@H]4C[C@H](n5cnc6c(N)ncnc65)O[C@@H]4COP(=O)(O)O[C@@H]23)c(=O)[nH]1] (1S,6R,8R,10S,15R,18R)-18-(2-amino-6-oxo-6,9-dihydro-1H-purin-9-yl)-8-(6-amino-9H-purin-9-yl)-3,12-dihydroxy-2,4,7,11,13,16-hexaoxa-3$\lambda^5$,12$\lambda^5$-diphosphatricyclo[13.3.0.0$^{6,10}$]octadecane-3,12-dione | 641.4 |
| 53: HPLC retention time (HILIC, min): 4.21. $^1$H NMR (400 MHz, $D_2O$) δ 8.21 (s, 1H), 8.19 (s, 1H), 7.74 (s, 1H), 6.41 (d, 1H, J = 6.7 Hz), 6.09 (q, 1H, J = 6.7 Hz), 5.20 (dt, J = 8.3, 5.8 Hz, 1H), 4.98 (m, 1H), 4.41 - 4.19 (m, 5H), 4.13 - 3.99 (m, 3H), 2.91 (dd, J = 13.4, 6.8 Hz, 1H), 2.78 (ddd, J = 13.3, 10.0, 6.9 Hz, 1H). $^{13}$C NMR (101 MHz, $D_2O$) δ 159.72, 156.17, 153.12, 153.07, 152.00, 148.12, 141.57, 139.45, 119.29, 117.40, 85.13, 83.14 (d, J = 10.9 Hz), 82.93 (d, J = 9.7 Hz), 75.00 (d, J = 5.7 Hz), 72.02, 69.88 (d, J = 5.2 Hz), 63.99, 63.74 (d, J = 5.3 Hz), 62.54 (d, J = 5.1 Hz), 40.35). $^{31}$P NMR (162 MHz, $D_2O$) δ 1.77, 1.02. | | |

TABLE 1-continued

| Compound | Structure / Name | Mass $[M-H]^-$ |
|---|---|---|
| | Exemplary compounds and characterization data | |
| 54 | 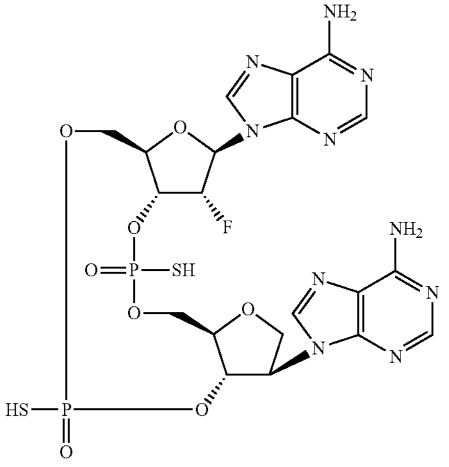 [SMILES: Nc1ncnc2c1ncn2[C@@H]1CO[C@@H]2COP(=O)(S)O[C@H]3[C@@H](F)[C@H](n4cnc5c(N)ncnc54)O[C@@H]3COP(=O)(S)O[C@@H]12] (1S,6R,8R,9R,10R,15R,18R)-8,18-bis(6-amino-9H-purin-9-yl)-9-fluoro-3,12-disulfanyl-2,4,7,11,13,16-hexaoxa-3$\lambda^5$,12$\lambda^5$-diphosphatricyclo[13.3.0.0$^{6,10}$]octadecane-3,12-dione | 675.5 |
| | 54: HPLC retention time (C18, min): 2.52. $^1$H NMR (400 MHz, $D_2O$) δ 8.21 (s, 1H), 8.20 (s, 1H), 8.11 (s, 1H), 8.07 (s, 1H), 6.42 (d, J = 15.8 Hz, 1H), 5.78 (dd, J = 51.0, 3.8 Hz, 1H), 5.34 (dt, J = 6.2, 3.0 Hz, 1H), 5.32 (m, 1H), 4.90 (m, 1H), 4.56 (m, 1H), 4.50 (bd, J = 11.8 Hz, 1H), 4.37 (dd, J = 10.5, 6.2 Hz, 1H), 4.29 (m, 1H), 4.28 (m, 1H), 4.17 (m, 1H), 4.13 (bdd, J = 10.5, 3.0 Hz, 1H), 4.03 (bdd, J = 11.8, 4.2 Hz, 1H). $^{13}$C NMR (101 MHz, $D_2O$) δ 157.74, 154.96, 154.81, 151.60, 150.21, 143.06, 141.42, 121.30, 121.12, 94.56 (d, J = 189.7 Hz), 89.74 (d, J = 33.7 Hz), 84.98 (t, J = 10.7 Hz), 81.85 (dd, J = 11.6, 8.7 Hz), 80.94 (d, J = 8.3 Hz), 73.18 (dd, J = 26.0, 4.7 Hz), 74.42, 65.66 (d, J = 4.7 Hz), 65.44 (d, J = 6.6 Hz), 64.47. $^{31}$P NMR (162 MHz, $D_2O$) δ 56.24, 53.77. $^{19}$F NMR (376 MHz, $D_2O$) δ −199.54. | |
| 55 | 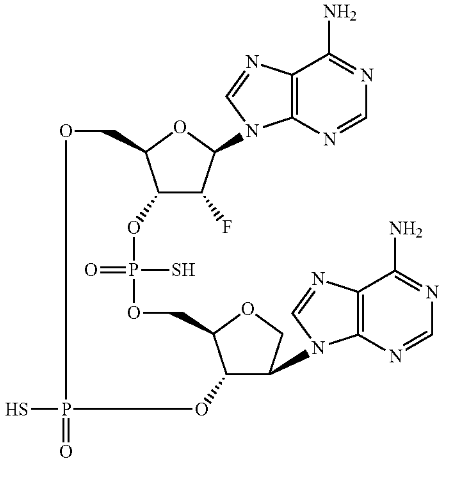 [SMILES: Nc1ncnc2c1ncn2[C@@H]1CO[C@@H]2COP(=O)(S)O[C@H]3[C@@H](F)[C@H](n4cnc5c(N)ncnc54)O[C@@H]3COP(=O)(S)O[C@@H]12] (1S,6R,8R,9R,10R,15R,18R)-8,18-bis(6-amino-9H-purin-9-yl)-9-fluoro-3,12-disulfanyl-2,4,7,11,13,16-hexaoxa-3$\lambda^5$,12$\lambda^5$-diphosphatricyclo[13.3.0.0$^{6,10}$]octadecane-3,12-dione | 675.5 |
| | 55: HPLC retention time (C18, min): 2.59. $^1$H NMR (400 MHz, $D_2O$) δ 8.18 (s, 2H), 8.08 (s, 2H), 6.40 (d, J = 16.0 Hz, 1H), 5.48 (dd, J = 51.5, 3.9 Hz, 1H), 5.37 (dt, J = 6.4, 3.5 Hz, 1H), 5.35 (m, 1H), 4.96 (m, 1H), 4.52 (dm, J = 9.0 Hz, 1H), 4.48 (dm, J = 12.2 Hz, 1H), 4.39 (ddd, J = 11.7, 2.7, 2.0 Hz, 1H), 4.35 (dd, J = 10.4, 6.4 Hz, 1H), 4.25 (dq, J = 6.6, 2.3 Hz 1H), 4.15 (ddd, J = 11.7, 6.2, 2.2 Hz, 1H), 4.09 (bdd, J = 10.4, 3.5 Hz, 1H), 4.03 (ddd, J = 12.2, 4.8, 1.3 Hz, 1H). $^{13}$C NMR (101 MHz, $D_2O$) δ 157.80, 155.02, 154.66, 151.53, 150.22, 143.24, 141.50, 121.26, 121.07, 95.11 (d, J = 190.0 Hz), 89.97 (d, J = 33.9 Hz), 84.66 (dd, J = 11.3, 8.4 Hz), 82.06 (dd, J = 11.4, 9.8 Hz), 80.71 (d, J = 8.5 Hz), 74.39, 72.02 (dd, J = 16.4, 8.5 Hz), 66.82 (d, J = 4.7 Hz), 65.11 (d, J = 4.4 Hz), 64.45. $^{31}$P NMR (162 MHz, $D_2O$) δ 55.76, 53.81. $^{19}$F NMR (376 MHz, $D_2O$) δ −197.80. | |

Example 1. Biological Evaluation

A cyclic dinucleotide was determined to be a STING agonist: (A) if it demonstrated binding to the AQ allelic form of human STING protein with thermal shift of >0.5° C. in the STING Differential Scanning Fluorimetry Assay (DSF), and (B) if it demonstrated STING activation through IRF-3 dependent expression of firefly luciferase reporter with $EC_{50}$<100 $\mu mol^{-1}$.

ISRE Reporter Plasmid (pGL64.27-4xISRE)

Two complementary oligonucleotides of the sequence AAAGATCTTGGAAAGTGAAACCTTG-GAAAACGAAACTGGACAAAGGGAAACTGCAGAA ACTGAAACAAAGCTTAA (SEQ ID NO:1) and TTAAGCTTTGTTTCAGTTTCTGCAGTTTCCCTTTGT CCAGTTTCGTTTTCCAAGGTTTCACT TTCCAA-GATCTTT (SEQ ID NO:2) containing four interferon-sensitive response elements (ISRE) were synthesized by Sigma Aldrich (Czech Republic, Prague). The oligonucleotides were mixed in equal molar amounts, hybridized, and cleaved by restriction endonucleases HindIII (cat. #.R0104S, NEB, Ipswich, USA) and BglII (cat. #R0144S, NEB, Ipswich, USA). Ultimately, they were ligated into plasmid pGL4.27 (cat. #E6651, Promega, Madison, USA) linearized with the same enzymes. As result the sequence with four ISRE sites was placed upstream of the minimum promoter of firefly luciferase reporter gene.

293T wtSTING-FL Reporter Cells 293T cells (cat. #CRL-3216, ATCC, Manassas, USA) were seeded a day before transfection at density 125,000 cells per $cm^2$ onto poly-D-lysine (cat. #P6407, Sigma Aldrich, Czech Republic) coated six well plates in antibiotic free DMEM with high glucose (cat. #D5796, Sigma Aldrich, Czech Republic) supplemented with 10% heat inactivated FBS (cat. #S1520, Biowest, Riverside, USA). On the day of transfection, 2.5 μg of the plasmid pUNO1-hSTING-WT (cat. #punol-hstingwt, InvivoGen, San Diego, USA) encoding human wild type STING (WT STING) was diluted in 125 μL OptiMEM medium (cat. #31985062, ThermoFisher, Waltham, USA) and mixed with 125 μL of the same medium containing 12.5 μL of Lipofectamine 2000 (cat. #11668019, ThermoFisher, Waltham, USA). After 5 minutes incubation at room temperature (RT), 250 μL of the mixture was added dropwise to the cells in one well. Cells were incubated 36 hours at 37° C. with 5% $CO_2$, and then detached with 0.05% Trypsin and 0.22 g/L EDTA (both cat. #L0941, Biowest, Riverside, USA).

Transfected cells were seeded onto poly-D-lysine coated six well plates at density 50,000 cells per 1 $cm^2$ in DMEM medium with high glucose containing 10% heat inactivated FBS, 30 μg/mL blasticidin (cat. #ant-b1-05, InvivoGen, San Diego, USA), 0.06 mg/ml Penicillin G and 0.1 mg/ml Streptomycin Sulfate (both cat. #. L0018, Biowest, Riverside, USA). The medium was replenished every 3-4 days until visible colonies of cells resistant to blasticidin were formed.

Blasticidin resistant cells stably expressing WT STING were further transfected with pGL64.27-4xISRE plasmid following the same procedure as described above. The transfected cells were selected for the resistance to 300 μg/mL hygromycin (cat. #. 10687010, ThermoFisher, Waltham, USA) in DMEM with high glucose containing 10% heat inactivated FBS, 30 μg/mL blasticidin, 0.06 mg/ml Penicillin G and 0.1 mg/ml Streptomycin Sulfate. Homogeneous culture of stably double transfected cells was prepared by limiting dilution of cells in 96 well plates and wells with cells were selected that originated from a single cell. These cells were expanded, and expression of WT STING was confirmed by western blot using monoclonal mouse anti STING antibodies (cat. #. MAB7169, 1:1000 dilution; 2° antibody cat. #. HAF007, 1:2000 dilution, both from R&D Systems, Minneapolis, USA), and by induction of firefly luciferase expression in the presence of 50 μM STING agonist 2'3' cGAMP (cat. #tlrl-nacga23, InvivoGen, San Diego, USA). Genomic DNA from the transfected cells was amplified with primers pUNO1_Seq_F (TGCTTGCT-CAACTCTACGTC) (SEQ ID NO:3) and pUNO1_Seq_R (GTGGTTTGTCCAAACTCATC) (SEQ ID NO:4) that were complementary to pUNO1 plasmid and the presence of WT STING gene in the transfected cells was confirmed by DNA sequencing.

Digitonin Assay Using 293T wtSTING-FL Reporter Cells 293T wtSTING-FL cells were seeded at density of 250,000 cells per $cm^2$ onto 96 well poly-D-lysine coated plates in 100 μl DMEM with high glucose supplemented with 10% heat inactivated FBS. The medium was removed next day and three fold serial dilutions of compounds in Digitonin buffer containing 50 $mmol \cdot l^{-1}$ HEPES (cat. #H3375, Sigma Aldrich, Czech Republic) pH 7.0, 100 $mmol \cdot l^{-1}$ KCl, 3 $mmol \cdot l^{-1}$ $MgCl_2$, 0.1 $mmol. \cdot l^{-1}$ DTT (cat. #D0632, Sigma Aldrich, Czech Republic), 85 $mmol \cdot l^{-1}$ Sucrose (cat. #S7903, Sigma Aldrich, Czech Republic), 0.2% BSA (cat. #A2153, Sigma Aldrich, Czech Republic), 1 $mmol \cdot l^{-1}$ ATP (cat. #A1852, Sigma Aldrich, Czech Republic), 0.1 $mmol \cdot l^{-1}$ GTP (cat. #G8877, Sigma Aldrich, Czech Republic), and 10 μg/mL Digitonin A (cat. #D141, Sigma Aldrich, Czech Republic) were added to the cells. The buffer was removed after 30 minutes incubation at 37° C. with 5% $CO_2$, the cells were washed once with 100 μl of cultivation medium, and 100 μl of medium was added to each well. The plates with cells were incubated for 5 hours at 37° C. with 5% $CO_2$, 50 μl of the medium was removed and 30 μl of ONE-Glo™ Luciferase Assay System reagent (cat. #E6120, Promega, Madison, USA) was added to each well. Luminescence was read on Synergy H1 (Biotek, Winooski, USA). GrafPad Prism (La Jolla, USA) was used to calculate the 50% effective concentration ($EC_{50}$) from an 8-point dose-response curve. Control compounds 3'3'-c-di-GMP (cat. #tlrl-nacdg), 3'3'-c-di-AMP (cat. #tlrl-nacda), 3'3'-cGAMP (cat. #tlrl-nacga), 2'3'-cGAMP (cat. #tlrl-nacga23), and 2'2'-cGAMP (cat. #tlrl-nacga22) were purchased from Invivogen (San Diego, USA).

WT STING and AQ STING Proteins

Both WT and AQ human STING (G230A-R293Q) cDNA were amplified by the use of PCR (Phusion® High-Fidelity DNA Polymerase, cat. #M0530S, NEB, Ipswich, USA) using oligonucleotides hSTING140-BamH-For (GTGG-GATCCGCCCCAGCTGAGATCTCTGCAG) (SEQ ID NO:5) and hSTING379-Not-Rev3 (TATGCGGCCGCCT-ATTACACAGTAACCTCTTCCTTTTC) (SEQ ID NO:6) from pUNO1-hSTING-WT (cat. #puno1-hstingwt, InvivoGen, San Diego, USA) and pUNO1-hSTING-HAQ plasmids (punol-hsting-haq, InvivoGen, San Diego, USA). Purified PCR products were cleaved with restriction enzymes BamHI (cat. #R0136S, NEB, Ipswich, USA) and Notl (cat. #R0189S, NEB, Ipswich, USA) and cloned into the pSUMO vector linearized with the identical enzymes. Plasmid pSUMO was created by introducing 8-His-SUMO sequence between Ndel and BamHI sites of pHis-parallel2 plasmid (Clontech, Moutain View, USA). pSUMO-STING WT or pSUMO-STING AQ plasmids thus encoded truncated human WT STING or AQ STING (amino acid residues 140-343) with N-terminal 8xHis and SUMO tag.

The recombinant WT STING and AQ STING proteins were overexpressed in Rosetta-gami B (DE3) competent cells (cat. #71136-3, Merck Millipore, Billerica, USA). Bacterial pellets were re-suspended in ice-cold lysis buffer containing 50 mmol·l$^{-1}$ TrisCl (cat. #T1503, Sigma Aldrich, Czech Republic) pH 8.0, 300 mmol·l$^{-1}$ NaCl, 3 mmol·l$^{-1}$ β-mercaptoethanol (cat. #M6250, Sigma Aldrich, Czech Republic), 10% glycerol (cat. #G5516, Sigma Aldrich, Czech Republic) and 20 mmol·l$^{-1}$ imidazole (cat. #15513, Sigma Aldrich, Czech Republic) using Dounce homogenizer. DNase I (cat. #D5025, Sigma Aldrich, Czech Republic) and RNase A (cat. #R6513, Sigma Aldrich, Czech Republic) were added (final concentration 50 μg/ml) together with $MgCl_2$ (final concentration 5 mmol·l$^{-1}$) to the homogenate and bacteria were lysed using French Press G-M™ High-Pressure Cell Press Homogenizer (1500 psi, 3 cycles). Lysate was spun 30,000 g for 20 minutes and supernatant was gently stirred with Ni-NTA resin (cat. #745400.25 Macherey-Nagel, Duren, Germany) for 30 minutes. The resin was poured into a chromatography column, washed with 50 ml buffer A (50 mmol·l$^{-1}$ TrisCl (pH 8.0), 800 mmol·l$^{-1}$ NaCl, 3 mmol·l$^{-1}$ (3-mercaptol; 10% glycerol; 20 mmol·l$^{-1}$ imidazole) and 8-His-SUMO tagged STING proteins were eluted with 15 ml buffer A containing 300 mmol·l$^{-1}$ imidazole. The eluted proteins were cleaved with recombinant SUMO protease (80 μg/ml of protein solution, cat. #12588018, ThermoFisher, Waltham, USA). The proteins were further purified by size exclusion chromatography using HiLoad 16/60 Superdex 75 (cat. #28989333, GE Healthcare Bio-Sciences, Pittsburgh, USA) in 50 mmol·l$^{-1}$ Tris Cl buffer pH 7.4 containing 150 mmol·l$^{-1}$ NaCl, and 10% glycerol. Proteins were concentrated with Amicon® Ultra-15 10 K device (cat. #UFC901008, Merck Millipore, Billerica, USA) and flash frozen in liquid $N_2$.

DNA sequence of 8-His-SUMO
(SEQ ID NO: 7)
ATGTCGCATCACCATCATCATCACCACCATGGGATGTCGGACTCAGAAGT

CAATCAAGAAGCTAAGCCAGAGGTCAAGCCAGAAGTCAAGCCTGAGACTC

ACATCAATTTAAAGGTGTCCGATGGATCTTCAGAGATCTTCTTCAAGATC

AAAAAGACCACTCCTTTAAGAAGGCTGATGGAAGCGTTCGCTAAAAGACA

GGGTAAGGAAATGGACTCCTTAAGATTCTTGTACGACGGTATTAGAATTC

AAGCTGATCAGACCCCTGAAGATTTGGACATGGAGGATAACGATATTATT

GAGGCTCACCGCGAACAGATTGGTGGATCC.

Amino acid sequence of 8-His-SUMO
(SEQ ID NO: 8)
MSHHHHHHHHGMSDSEVNQEAKPEVKPEVKPETHINLKVSDGSSEIFFKI

KKTTPLRRLMEAFAKRQGKEMDSLRFLYDGIRIQADQTPEDLDMEDNDII

EAHREQIGGS.

Amino acid sequence of truncated WT STING
(SEQ ID NO: 9)
APAEISAVCEKGNFNVAHGLAWSYYIGYLRLILPELQARIRTYNQHYNNL

LRGAVSQRLYILLPLDCGVPDNLSMADPNIRFLDKLPQQTGDRAGIKDRV

YSNSIYELLENGQRAGTCVLEYATPLQTLFAMSQYSQAGFSREDRLEQAK

LFCRTLEDILADAPESQNNCRLIAYQEPADDSSFSLSQEVLRHLRQEEKE

EVTV.

-continued

Amino acid sequence of truncated AQ STING
(SEQ ID NO: 10)
APAEISAVCEKGNFNVAHGLAWSYYIGYLRLILPELQARIRTYNQHYNNL

LRGAVSQRLYILLPLDCGVPDNLSMADPNIRFLDKLPQQTADRAGIKDRV

YSNSIYELLENGQRAGTCVLEYATPLQTLFAMSQYSQAGFSREDRLEQAK

LFCQTLEDILADAPESQNNCRLIAYQEPADDSSFSLSQEVLRHLRQEEKE

EVTV.

Differential Scanning Fluorimetry With WT STING and AQ STING

WT and AQ allelic forms of STING protein were diluted to the final concentration 0.1 mg/ml in 100 mmol·l$^{-1}$ TrisCl buffer pH 7.4 containing, 150 mmol·l$^{-1}$ NaCl, 1:500 SYPRO Orange (cat. #S6650, ThermoFisher, Waltham, USA) and 150 μM CDN or water. 20 μL solutions of the reaction mixtures were pipetted in triplicates into 96 well optical reaction plates and thermal denaturation of samples were performed on real time PCR cycler (LightCycler® 480 Instrument II—Roche, Basel, Switzerland). The first derivative of the thermal denaturation curves was performed to calculate denaturing temperatures of STING—CDN complexes and STING apoproteins. The thermal shift for each CDN was calculated by subtracting the average denaturing temperature of STING apoprotein from the average denaturing temperature of STING CDN complex.

Mouse cGAS Enzyme

A recombinant DNA encoding cDNA of murine cGAS (residues 147-507) was chemically synthesized by GenScript (Piscataway, NJ). This sequence was cloned into the vector pET-22b(+) in-frame between pelB leader and His-tag by homologous recombination using Gibson Assembly® Master Mix (New England Biolabs). The protein was overexpressed in *E. coli* BL21 (DE3) (ThermoFisher, Waltham, USA). Bacterial pellet was re-suspended in ice-cold lysis buffer containing 20 mM Phosphate Na buffer (pH 7.4), 500 mM NaCl, 10% glycerol, and 20 mM imidazole using Dounce homogenizer. DNase I and RNase A were added (final concentration 50 μg/ml) together with $MgCl_2$ (final concentration 5 mM) to the homogenate and bacteria were lysed using MSE Soniprep 150 (3 mm Tip Solid Titanium Exponential Probe, 2 min, 50% power, amplitude 12 microns). The lysate was spun 30,000×g for 20 minutes and supernatant was loaded onto 5 mL HisTrap column (GE Healthcare BioSciences, Pittsburgh, USA). The resin was washed with 50 ml lysis buffer and mcGAS was eluted with 15 ml 20 mM Phosphate-Na buffer (pH 7.4) buffer containing 500 mM NaCl; 10% glycerol, and 300 mM imidazole. The protein was further purified by size exclusion chromatography using HiLoad 16/60 Superdex 75 in buffer containing 150 mM NaCl; 50 mM Tris (pH 7.4), and 10% glycerol. The protein buffer was exchanged for 50% glycerol, 50 mM Tris (pH 7.6), 100 mM NaCl, 1 mM DTT, 1 mM EDTA with Amicon® Ultra-15 10 K Device (Merck Millipore Ltd.), and mcGAS was flash frozen in liquid $N_2$.

Murine cGAS amino acid sequence including pelB leader and His-tag
(SEQ ID NO: 11)
MKYLLPTAAAGLLLLAAQPAMAMPDKLKKVLDKLRLKRKDISEAAETVNK

VVERLLRRMQKRESEFKGVEQLNTGSYYEHVKISAPNEFDVMFKLEVPRI

ELQEYYETGAFYLVKFKRIPRGNPLSHFLEGEVLSATKMLSKFRKIIKEE

VKEIKDIDVSVEKEKPGSPAVTLLIRNPEEISVDIILALESKGSWPISTK

-continued

```
EGLPIQGWLGTKVRTNLRREPFYLVPKNAKDGNSFQGETWRLSFSHTEKY

ILNNHGIEKTCCESSGAKCCRKECLKLMKYLLEQLKKEFQELDAFCSYHV

KTAIFHMWTQDPQDSQWDPRNLSSCFDKLLAFFLECLRTEKLDHYFIPKF

NLFSQELIDRKSKEFLSKKIEYERNNGFPIFDKLLEHHHHHH.
```

TABLE 2

Biological Data

| Compound | DSF $\Delta T_m$ (° C.) WT STING | DSF $\Delta T_m$ (° C.) AQ STING | Digitonin assay $EC_{50}$ (μmol · $l^{-1}$) WT STING |
|---|---|---|---|
| 28 | 5.6 | 13.3 | 0.02 |
| 24 | 8.5 | 16.9 | 0.03 |
| 34 | 1.6 | 9.2 | 0.45 |
| 50 | 1.8 | 9.3 | 0.28 |
| 51 | 6.8 | 15.8 | 0.08 |
| 52 | 2.4 | 10.7 | 1.35 |
| 53 | 2.9 | 11.5 | 0.28 |

TABLE 2-continued

Biological Data

| Compound | DSF $\Delta T_m$ (° C.) WT STING | DSF $\Delta T_m$ (° C.) AQ STING | Digitonin assay $EC_{50}$ (μmol · $l^{-1}$) WT STING |
|---|---|---|---|
| 54 | 8.5 | 17.2 | 0.01 |
| 55 | 11.0 | 20.0 | 0.01 |

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

Synthesis and Characterization of 3'3' Isonucleotidic CDN Prodrugs

The synthesis of compound 36 from compound 27 was accomplished according to the synthetic scheme depicted below, and detailed in the following description.

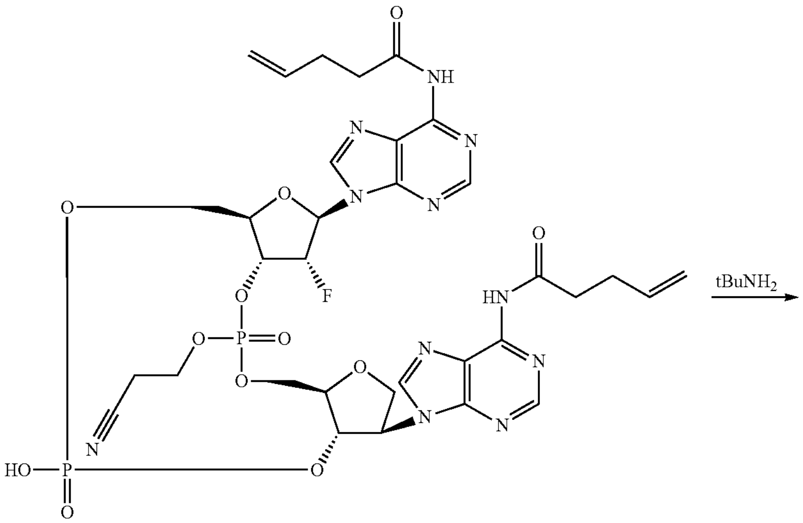

27

-continued

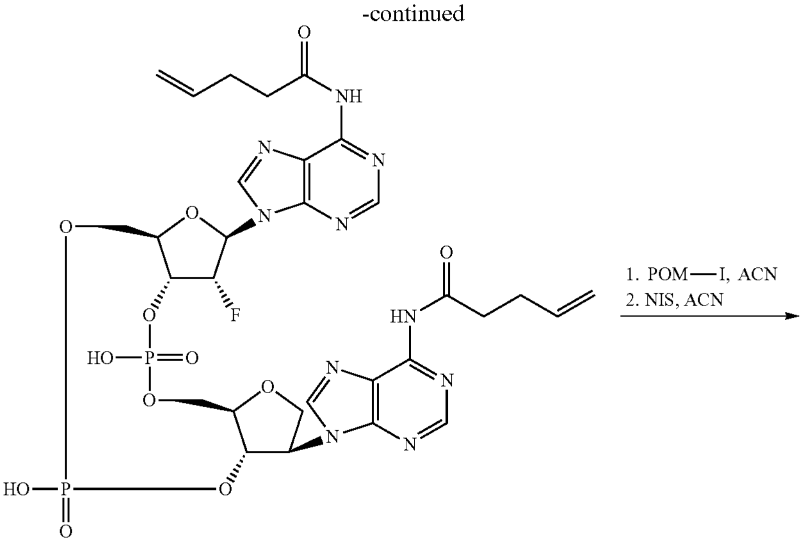

35

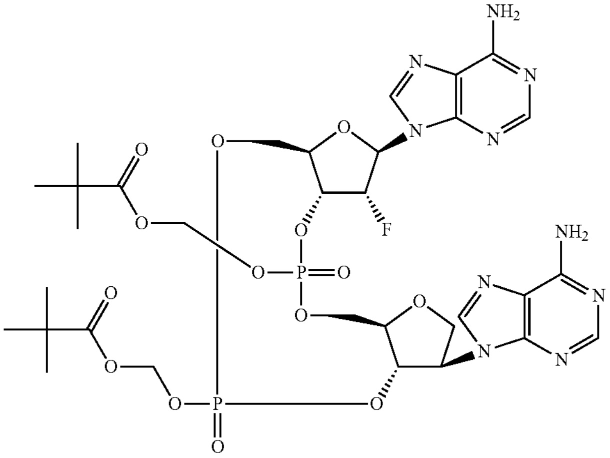

36

Crude 27 (cyclization starting from 46 mg of 9) was treated with neat $tBuNH_2$ (5 mL) at ambient temperature for 20 minutes. Volatiles were evaporated and 35 was purified on RP FCC (ACN in 50 mM $NH_4HCO_3$, 0-100%, elution 40%) to afford base-only protected cyclic dinucleotide (32 mg, $TEA^+$ salt). $TEA^+$ was exchanged for a tetrabutylammonium cation on a DOWEX 50 ($TBA^+$ cycle)

Nucleobase-protected CDN (2 lima tetrabutylammonium salt) was azeotroped with dry toluene (1×500 μL) and dry ACN (2×500 μL), dissolved in dry ACN (700 uL) and treated with pivaloyloxymethyl iodide (20 μmol, 5.3 μL, J. E. Coughlin et al.; Bioorg. Med. Chem. Lett. 20 (2010) 1783-1786) under argon atmosphere at ambient temperature for 1 hour. The reaction mixture was quenched with 1 ml of 50% $H_2O$/ACN and further diluted with 3 ml of water and purified on HPLC column (HPLC method 1). Fractions containing products (all 4 diastereoisomers) were pooled, evaporated and azeotroped with dry ACN (3×2 mL). To a solution of this intermediate in dry ACN (1 mL) under argon atmosphere was added NIS (2.2 mg, 10 μmol). The reaction mixture was stirred at ambient temperature for 1 hour, after which water (100 μL) was added followed by acetic acid (10 μL). After 30 minutes of further stirring the reaction was quenched with saturated aqueous solution of $Na_2S_2O_3$ (until decolorization), mixture was diluted with water (2 mL) and purified on HPLC column (HPLC method 2) affording 4 separate diastereisomers (the chiral centres being the phosphorus atoms) in approximately equimolar ratio (ca 150 nmol each)

HPLC Method 1

| Time (min) | Flow (mL/min) | $H_2O$ (%) | 1:1 $H_2O$/ACN (%) | ACN (%) |
|---|---|---|---|---|
| 0 | 2 | 100 | — | — |
| 2 | 3 | 100 | — | — |
| 10 | 3 | 100 | — | — |
| 30 | 3 | — | 100 | — |
| 50 | 3 | — | — | 100 |
| 70 | 3 | — | — | 100 |

HPLC Method 2

| Time (min) | Flow (mL/min) | $H_2O$ (%) | 1:1 $H_2O$/ACN (%) | ACN (%) |
|---|---|---|---|---|
| 0 | 2 | 80 | 20 | — |
| 2 | 3 | 80 | 20 | — |

-continued

| Time (min) | Flow (mL/min) | $H_2O$ (%) | 1:1 $H_2O$/ACN (%) | ACN (%) |
|---|---|---|---|---|
| 10 | 3 | 80 | 20 | — |
| 40 | 3 | — | 100 | — |
| 60 | 3 | — | 50 | 50 |
| 80 | 3 | — | — | 100 |

Preparative HPLC purifications were performed on Ingos LCP5020 chromatography system with columns packed with C18 reversed phase resin (Phenomenex Luna® RP18 Column, 5 μm, 10×150 mm). In all methods were used linear gradients.

The C18 analytical HPLC method described above was used for standard analysis.

The following compounds were synthesized using the aforementioned methods using the compounds described above.

TABLE 3

| Exemplary compounds and characterization data | | |
|---|---|---|
| Compound | Structure / Data | Mass $[M + H]^+$ |
| 36a-d | 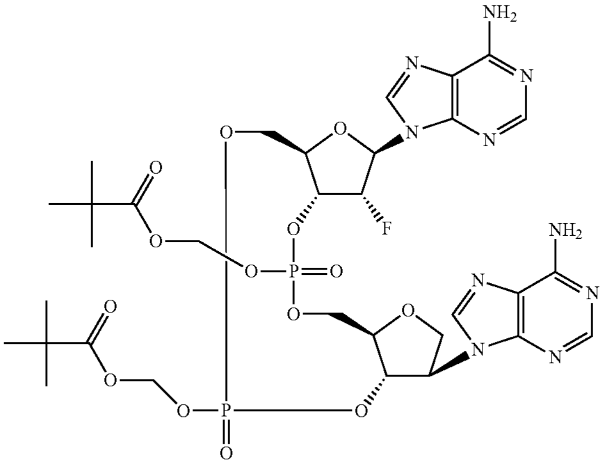 [SMILES: CC(C)(C)C(=O)OCOP1(=O)OC[C@H]2OC[C@@H](n3cnc4c(N)ncnc43)[C@@H]2OP(=O)(OCOC(=O)C(C)(C)C)OC[C@H]2O[C@@H](n3cnc4c(N)ncnc43)[C@H](F)[C@@H]2O1] {[(1R,6R,9R,10S,15R,17R,18R)-9,17-bis(6-amino-9H-purin-9-yl)-12-{[(2,2-dimethylpropanoyl)oxy]methoxy}-18-fluoro-3,12-dioxo-2,4,7,11,13,16-hexaoxa-3λ$^5$,12λ$^5$-diphosphatricyclo[13.3.0.0$^{6,10}$]octadecan-3-yl]oxy}methyl 2,2-dimethylpropanoate<br>36a: HPLC retention time (C18, min): 3.42. $^1$H NMR (501 MHz, $CD_3CN$) δ 8.29 (s, 1H), 7.81 (s, 1H), 7.97 (s, 1H), 7.87 (s, 1H), 6.26 (bs, 2H), 6.18 (m, 1H), 6.16 (bs, 2H), 5.60 - 5.76 (m, 4H), 5.52 (m, 1H), 5.28 (td, J = 6.9, 4.6 Hz, 1H), 4.82 - 4.91 (m, 2H), 4.27-4.45 (m, 8H), 1.15 (s, 9H), 0.95 (s, 9H). $^{31}$P NMR (202.4 MHz, $CD_3CN$) δ −4.78 (s), −5.18 (s). $^{19}$F NMR (470.4 MHz, $CD_3CN$) δ −196.67 (dm, J = 52.5 Hz).<br>36b: HPLC retention time (C18, min): 3.61. $^1$H NMR (501 MHz, $CD_3CN$) δ 8.29 (s, 1H), 7.77 (s, 1H), 8.03 (s, 1H), 7.87 (s, 1H), 6.19 (dd, 1H, J = 21.7, 1.1 Hz), 6.18 (bs, 2H), 6.12 (bs, 2H), 5.63 - 5.82 (m, 4H), 5.32 - 5.39 (m, 2H), 5.15 (dd, J = 15.4, 5.2 Hz, 1H), 5.03 (dd, J = 12.6, 5.2 Hz, 1H), 4.27 - 4.44 (m, 8H), 1.23 (s, 9H), 0.93 (s, 9H). $^{31}$P NMR (202.4 MHz, $CD_3CN$) δ −2.38 (s), −4.98 (s). $^{19}$F NMR (470.4 MHz, $CD_3CN$) δ −195.22 (dt, J = 52.5, 21.0 Hz).<br>36c: HPLC retention time (C18, min): 3.62. $^1$H NMR (501 MHz, $CD_3CN$) δ 8.21 (s, 1H), 8.01 (s, 1H), 7.97 (s, 1H), 7.93 (s, 1H), 6.23 (dd, 1H, J = 18.8, 1.5 Hz), 6.04 (bs, 4H), 5.47 - 5.73 (m, 7H), 5.31 (m, 1H), 4.27 - 4.49 (m, 8H), 1.16 (s, 9H), 1.14 (s, 9H). $^{31}$P NMR (202.4 MHz, $CD_3CN$) δ −2.82 (s), −4.78 (s). $^{19}$F NMR (470.4 MHz, $CD_3CN$) δ −198.00 (dt, J = 51.8, 18.7 Hz).<br>36d: HPLC retention time (C18, min): 3.84. D: $^1$H NMR (501 MHz, $CD_3CN$) δ 8.22 (s, 1H), 8.02 (s, 2H), 7.92 (s, 1H), 6.23 (dd, J = 20.3, 1.2 Hz, 1H), 6.05 (bs, 2H), 6.04 (bs, 2H), 5.49 - 5.77 (m, 7H), 5.35 (m, 1H), 4.17-4.49 (m, 8H), 1.23 (s, 9H), 1.15 (s, 9H). $^{31}$P NMR (202.4 MHz, $CD_3CN$) δ −2.15 (s), −2.42 (s). $^{19}$F NMR (470.4 MHz, $CD_3CN$) δ −195.73 (dt, J = 51.9, 19.9 Hz). | 873.3 |

TABLE 3-continued

Exemplary compounds and characterization data

| Compound | Structure / Data | Mass $[M + H]^+$ |
| --- | --- | --- |
| 56a-d | 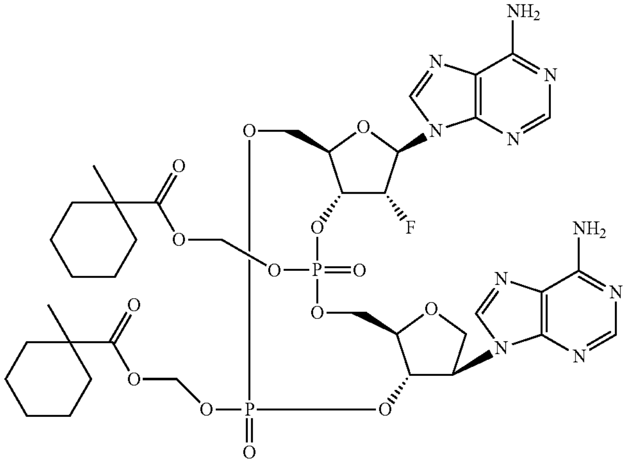 [SMILES: CC1(C(=O)OCOP2(=O)OC[C@H]3OC[C@@H](n4cnc5c(N)ncnc54)[C@@H]3OP(=O)(OCOC(=O)C3(C)CCCCC3)OC[C@H]3O[C@@H](n4cnc5c(N)ncnc54)[C@H](F)[C@@H]3O2)CCCCC1] {[(1S,6R,8R,9R,10R,15R,18R)-8,18-bis(6-amino-9H-purin-9-yl)-9-fluoro-12-[(1-methylcyclohexanecarbonyloxy)methoxy]-3,12-dioxo-2,4,7,11,13,16-hexaoxa-3$\lambda^5$,12$\lambda^5$-diphosphatricyclo[13.3.0.0$^{6,10}$]octadecan-3-yl]oxy}methyl 1-methylcyclohexane-1-carboxylate<br>56a: HPLC retention time (C18, min): 3.88.<br>56b: HPLC retention time (C18, min): 4.14.<br>56c: HPLC retention time (C18, min): 4.14.<br>56d: HPLC retention time (C18, min): 4.41. $^1$H NMR (501 MHz, $CD_3CN$) δ 8.22 (s, 1H), 8.02 (s, 1H), 8.02 (s, 1H), 7.92 (s, 1H), 6.23 (dd, J = 20.2, 1.2 Hz, 1H), 6.09 (bs, 2H), 6.07 (bs, 2H), 5.51 - 5.78 (m, 7H), 5.35 (m, 1H), 4.17 - 4.50 (m, 8H), 1.98 - 2.05 (m, 4H), 1.19 - 1.62 (m, 16H), 1.19 (s, 3H), 1.11 (s, 3H). $^{31}$P NMR (202.4 MHz, $CD_3CN$) δ −2.18, −2.27. $^{19}$F NMR (470.4 MHz, $CD_3CN$) δ −195.70 (dt, J = 52.0, 19.9 Hz). | 953.3 |
| 57a-d | 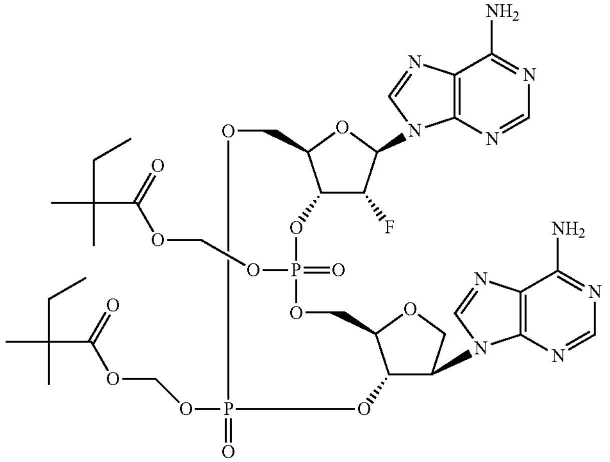 [SMILES: CCC(C)(C)C(=O)OCOP1(=O)OC[C@H]2OC[C@@H](n3cnc4c(N)ncnc43)[C@@H]2OP(=O)(OCOC(=O)C(C)(C)CC)OC[C@H]2O[C@@H](n3cnc4c(N)ncnc43)[C@H](F)[C@@H]2O1] {[(1R,6R,9R,10S,15R,17R,18R)-9,17-bis(6-amino-9H-purin-9-yl)-12-{[(2,2-dimethylbutanoyl)oxy]methoxy}-18-fluoro-3,12-dioxo-2,4,7,11,13,16-hexaoxa-3$\lambda^5$,12$\lambda^5$-diphosphatricyclo[13.3.0.0$^{6,10}$]octadecan-3-yl]oxy}methyl 2,2-dimethylbutanoate<br>57a: HPLC retention time (C18, min): 3.61.<br>57b: HPLC retention time (C18, min): 3.83.<br>57c: HPLC retention time (C18, min): 3.84.<br>57d: HPLC retention time (C18, min): 4.08. $^1$H NMR (501 MHz, $CD_3CN$) δ 8.22 (s, 1H), 8.02 (s, 1H), 8.02 (s, 1H), 7.92 (s, 1H), 6.24 (dd, J = 20.2, 1.2 Hz, IH), 6.05 (bs, 2H), 6.03 (bs, 2H), 5.49 - 5.77 (m, 7H), 5.35 (m, 1H), 4.17 - 4.49 (m, 8H), 1.61 (q, 2H, J = 7.5 Hz), 1.54 (q, 2H, J = 7.5 Hz), 1.18 (s, 6H), 1.12 (s, 3H), 1.11 (s, 3H), 0.86 (t, J = 7.5 Hz, 3H), 0.79 (t, J = 7.5 Hz, 3H). $^{31}$P NMR (202.4 MHz, $CD_3CN$) δ −2.16, −2.34. $^{19}$F NMR (470.4 MHz, $CD_3CN$) δ −195.71 (dt, J = 52.0, 19.9 Hz). | 901.3 |

TABLE 3-continued

| Exemplary compounds and characterization data | | |
|---|---|---|
| Compound | Structure / Data | Mass $[M + H]^+$ |
| 58a-d | 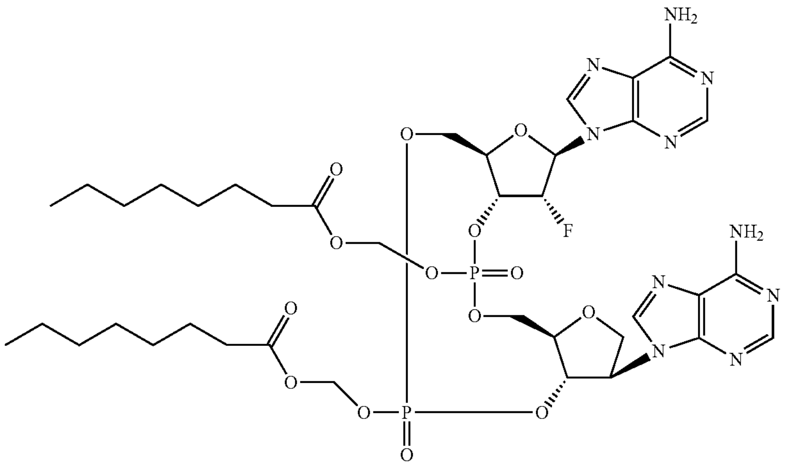 [SMILES: CCCCCCCC(=O)OCOP1(=O)OC[C@H]2OC[C@@H](n3cnc4c(N)ncnc43)[C@@H]2OP(=O)(OCOC(=O)CCCCCCC)OC[C@H]2O[C@@H](n3cnc4c(N)ncnc43)[C@H](F)[C@@H]2O1]<br>{[(1R,6R,9R,10S,15R,17R,18R)-9,17-bis(6-amino-9H-purin-9-yl)-18-fluoro-12-[(octanoyloxy)methoxy]-3,12-dioxo-2,4,7,11,13,16-hexaoxa-3$\lambda^5$,12$\lambda^5$-diphosphatricyclo[13.3.0.$0^{6,10}$]octadecan-3-yl]oxy}methyl octanoate<br>58a: HPLC retention time (C18, min): 4.38.<br>58b: HPLC retention time (C18, min): 4.55.<br>58c: HPLC retention time (C18, min): 4.57.<br>58d: HPLC retention time (C18, min): 4.81. $^1$H NMR (501 MHz, $CD_3CN$) δ 8.22 (s, 1H), 8.05 (s, 1H), 8.02 (s, 1H), 7.93 (s, 1H), 6.24 (dd, J = 20.1, 1.3 Hz, 1H), 6.03 (bs, 2H), 6.01 (bs, 2H), 5.48 - 5.75 (m, 7H), 5.34 (m, 1H), 4.17 - 4.48 (m, 8H), 2.41 (t, J = 7.5 Hz, 2H), 2.33 (m, 2H), 1.52 - 1.63 (m, 4H), 1.20 - 1.40 (m, 16H), 0.87 (t, 3H, J = 7.1 Hz), 0.86 (t, 3H, J = 7.1 Hz). $^{31}$P NMR (202.4 MHz, $CD_3CN$) δ −2.15, −2.37. $^{19}$F NMR (470.4 MHz, $CD_3CN$) δ −195.95 (dt, J = 52.1, 19.9 Hz). | 957.3 |

293T WT STING Standard Reporter Assay 293T wtSTING-FL cells were seeded at density of 250,000 cells per $cm^2$ onto 96 well poly-D-lysine coated white micro plates in 100 ill DMEM medium with high glucose supplemented with 10% heat inactivated FBS. The medium was removed next day and three-fold serial dilutions of compounds in 100 μl medium were added to the cells. The plates with cells were incubated for 7 hours at 37° C. with 5% $CO_2$. After 50 μl of the medium was removed, 30 μl of ONE-Glo™ Luciferase Assay System reagent (cat. #E6120, Promega, Madison, USA) was added to each well and luminescence was read on Synergy H1 (Biotek, Winooski, USA). GraphPad Prism (La Jolla, USA) was used to calculate the 50% effective concentration ($EC_{50}$) from an 8-point dose-response curve. Control compounds 3'3'-cGAMP (cat. #tlrl-nacga), 2'3'-cGAMP (cat. #tlrl-nacga23), and 2'2'-cGAMP (cat. #tlrl-nacga22) were purchased from Invivogen (San Diego, USA).

TABLE 4

| 293T WT STING standard reporter assay data | |
|---|---|
| Compound | 293T WT STING $EC_{50}$ (μM) |
| 54 | 0.156 |
| 55 | 0.340 |
| 36a | 0.088 |
| 36b | 0.077 |
| 36c | 0.052 |
| 36d | 0.028 |
| 56a | 0.285 |
| 56b | 0.044 |
| 56c | 0.021 |

TABLE 4-continued

| 293T WT STING standard reporter assay data | |
|---|---|
| Compound | 293T WT STING $EC_{50}$ (μM) |
| 56d | 0.041 |
| 57a | 0.032 |
| 57b | 0.018 |
| 57c | 0.013 |
| 57d | 0.014 |
| 58a | 0.005 |
| 58b | 0.001 |
| 58c | 0.002 |
| 58d | 0.002 |
| 3'3'-cGAMP | 68.4 |
| 2'2'-cGAMP | 10.2 |
| 2'3'-cGAMP | 36.9 |

Peripheral Blood Mononuclear Cell Assay

Selected compounds were tested in an in vitro peripheral blood mononuclear cell (PBMC) assay. Freshly isolated PBMCs were seeded into U-shaped shaped 96-well plates at desity 500,000 cells per well in 50 μl of RPMI 1640 medium supplemented with 10% heat inactivated FBS. Serially diluted tested compounds were added to wells in 50 μl of cultivation medium and cell were incubated with compounds for 1 h at 37° C. with 5% $CO_2$. Plates with cells were then spun 500 g for 5 minutes and medium was removed. Cells were washed twice with the cell culture medium by the use of centrifugation and gently resuspended in 100 μl medium without compounds. After 15 hour incubation at 37° C. with 5% $CO_2$, the cell culture medium was collected and the levels of interferon-alpha (INF-α), interferon-gamma (INF-γ) and tumor necrosis factor-alpha (TNF-α)

were determined with ProcartaPlex Assays (ThermoFisher, Waltham, USA) and MAGPIX System (Merck KGaA, Darmstadt, Germany). GraphPad Prism (San Diego, CA, USA) was used to calculate the 50% effective concentration ($EC_{50}$) from a 6-point dose-response curve. Values reported are an average of runs from at least two donors.

TABLE 5

Peripheral blood mononuclear cell data

| Compound | PBMC $EC_{50}$ (μM) | | |
|---|---|---|---|
| | IFN-γ | TNF-α | IFN-α |
| 36d | 0.115 | 0.326 | 0.184 |
| 56d | 0.048 | 0.159 | 0.325 |
| 57d | 0.080 | 0.206 | 0.258 |
| 58d | 0.016 | 0.037 | 0.038 |

The invention claimed is:

1. A compound of formula (J):

(J)

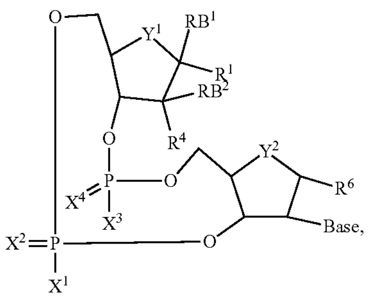

or an enantiomer, hydrate, solvate, or pharmaceutically acceptable salt or addition salt thereof, wherein $Y^1$ and $Y^2$ are each independently —O— or —$CH_2$—;

$X^1$ and $X^3$ are each independently OH, SH, $OR^{15}$, or $SR^{15}$, $X^2$ and $X^4$ are each independently O or S;

$RB^1$ is selected from Base' and H, $RB^2$ is selected from Base' and H, wherein one of $RB^1$ and $RB^2$ is Base';

$R^1$ is H or CN or F or Cl;

$R^4$ is H or OH or F;

$R^6$ is selected from H, CN, $N_3$, F, Cl, $COOR^{15}$, $CON(R^{15})_2$, $C_1$-$C_6$ alkyl, $C_2$-$C_6$ alkenyl, $C_2$-$C_6$ alkynyl, $OR^{15}$, $SR^{15}$, and $N(R^{15})_2$;

each $R^{15}$ is independently H, —C(=Z)$R^{16}$, —C(=Z)$OR^{16}$, —C(=Z)$SR^{16}$, —C(=Z)$N(R^{16})_2$, —$CH_2$—Z—C(=Z)$R^{16}$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each $R^{16}$ is independently H, $C_1$-$C_{12}$ alkyl, $C_2$-$C_{12}$ alkenyl, $C_2$-$C_{12}$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl; preferably each $R^{16}$ is independently H, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each Z is independently O or S;

Base' and Base are each independently:

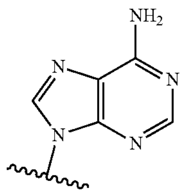
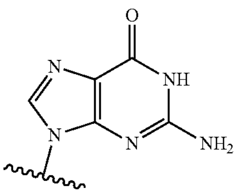
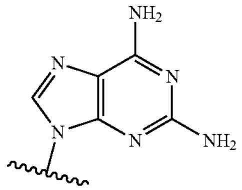
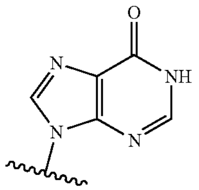
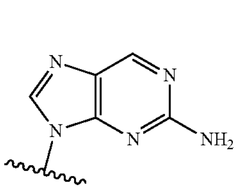
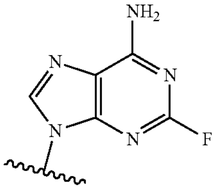
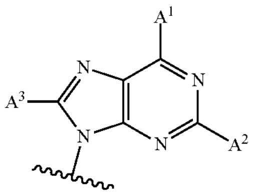
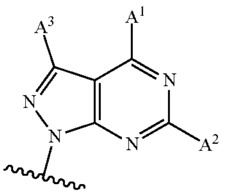
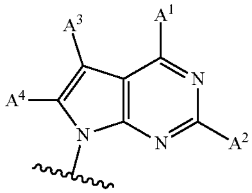
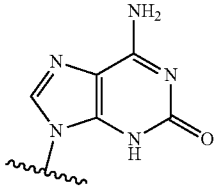

-continued

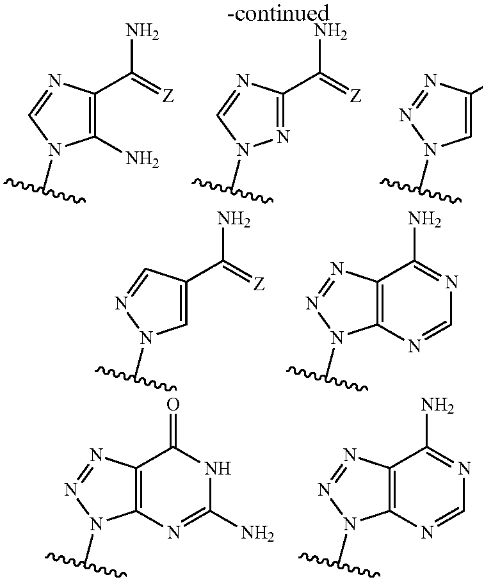

or

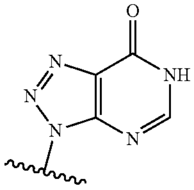

wherein $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$, and wherein the $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl independently in each instance is optionally substituted with 1, 2, or 3 substituents independently selected from —OH; —SH; —$NH_2$; —O; =NH; —S; halogen; —$N_3$; $C_6$-$C_{10}$ aryl optionally substituted with 1, 2, or 3 substituents independently selected from —OH, —CN, —O(C=O)$OR^B$, —O(C=O)$R^B$, and —$COOR^B$; unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino; unsubstituted $C_1$-$C_6$ dialkylamino; —CN; —O(C=O)$OR^B$; —O(C=O)$R^B$; and —$COOR^B$; wherein $R^B$ is H or unsubstituted $C_1$-$C_6$ alkyl.

2. The compound according to claim 1, having the structure Ja (Ja)

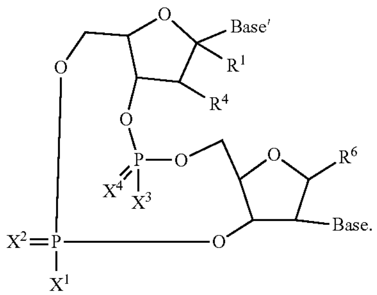

3. The compound according to claim 1, having the structure I (I)

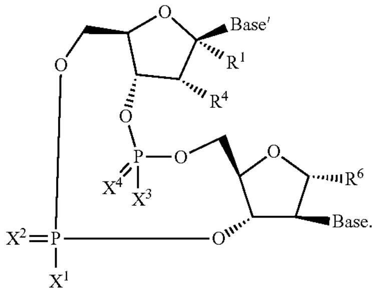

4. The compound according to claim 1, having the structure II (II)

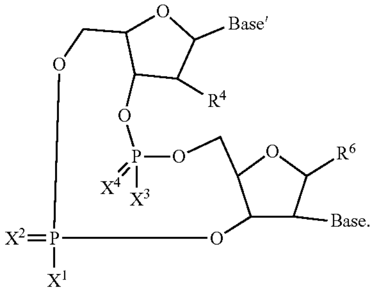

5. The compound according to claim 1, having the structure III (III)

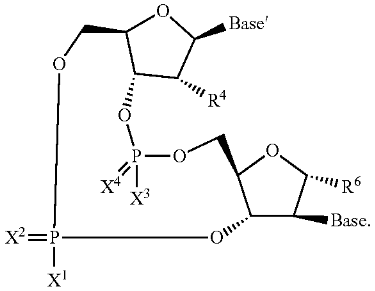

6. The compound according to claim 1, wherein $R^4$ is H or F.

7. The compound according to claim 1, wherein Base and Base' are each independently selected from:

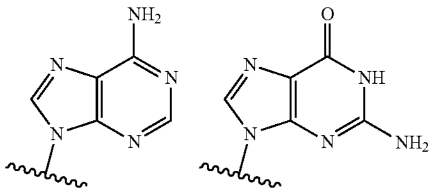

-continued
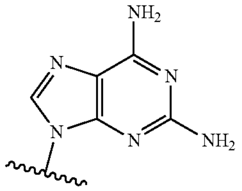
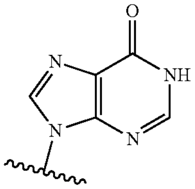
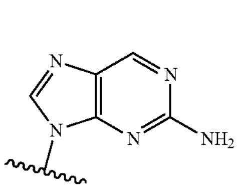
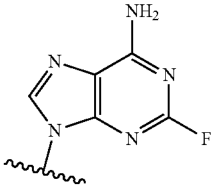
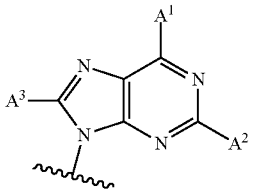
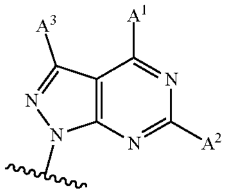
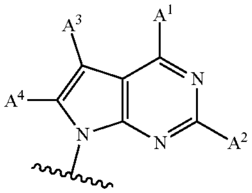
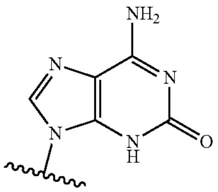
wherein
A, $A^1$, $A^2$, $A^3$ and $A^4$ are each independently H, OH, SH, F, Cl, Br, I, $NH_2$, $OR^{15}$, $SR^{15}$, $NHR^{15}$ $N(R^{15})_2$, or $R^{16}$.
8. The compound according to claim 1, wherein Base and Base' are each independently selected from:
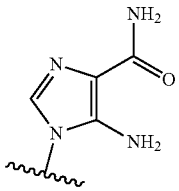
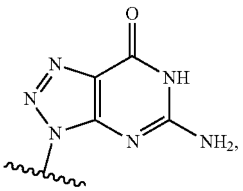
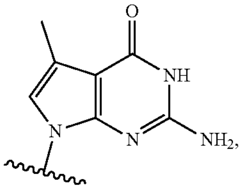
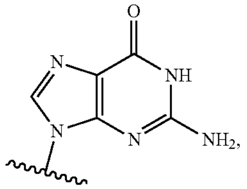
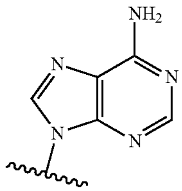
,
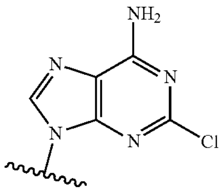
,
-continued
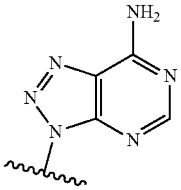
,
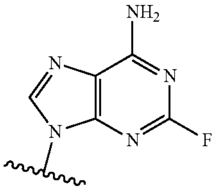
,
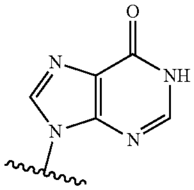
,
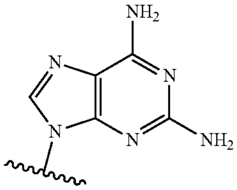
,
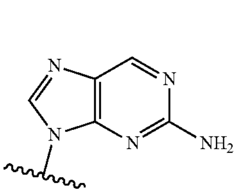
,
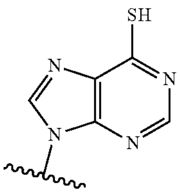
,
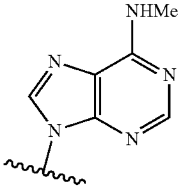
,
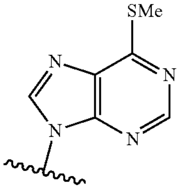
,
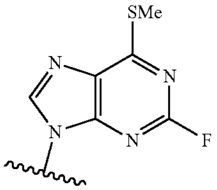
,
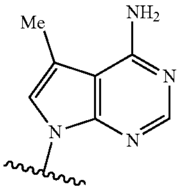
,
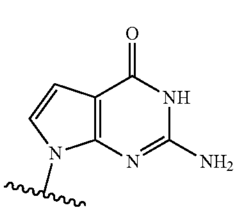
,
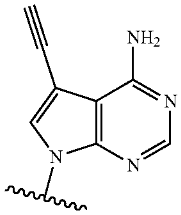
,
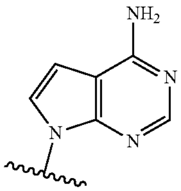
, and
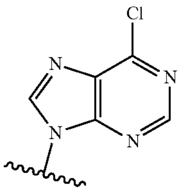
.
9. The compound according to claim 1, wherein Base and Base' are each independently selected from:
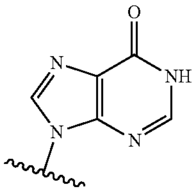
,
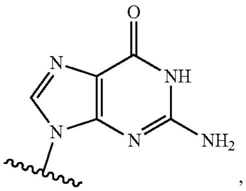
, and -continued
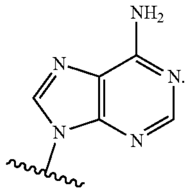
10. The compound according to, wherein Base' is and Base is
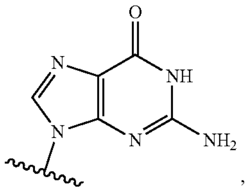
,
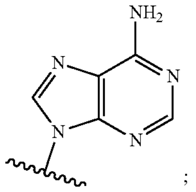
;
or Base' is and Base is
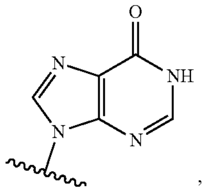
,
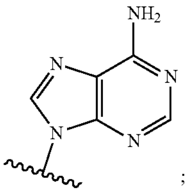
;
or Base' is and Base is
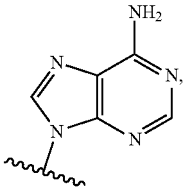
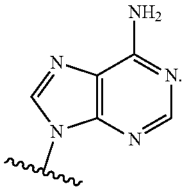
11. The compound of claim 1, wherein the compound is selected from:
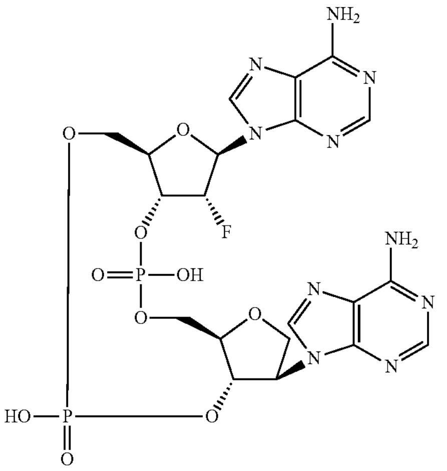
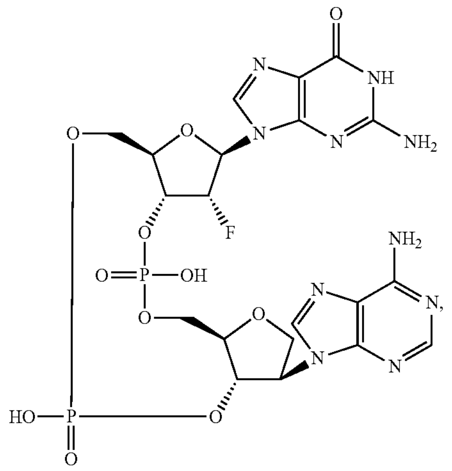
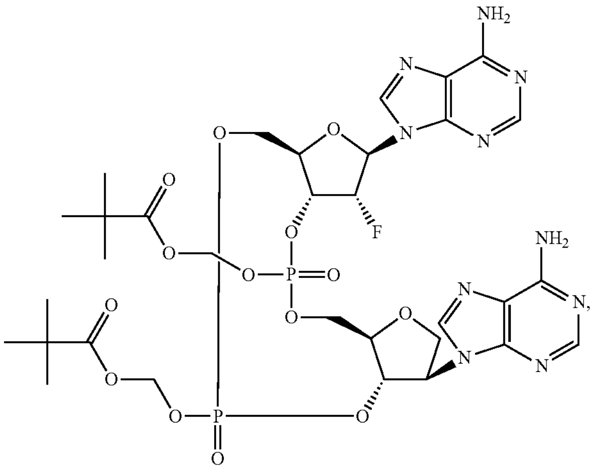

-continued
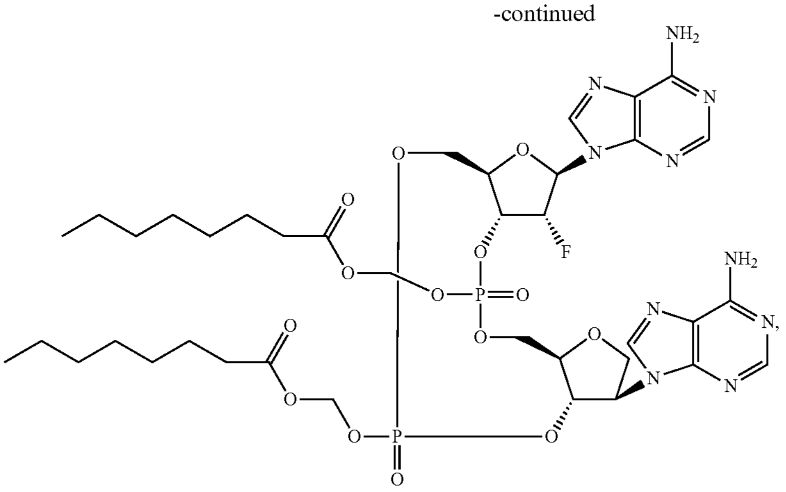
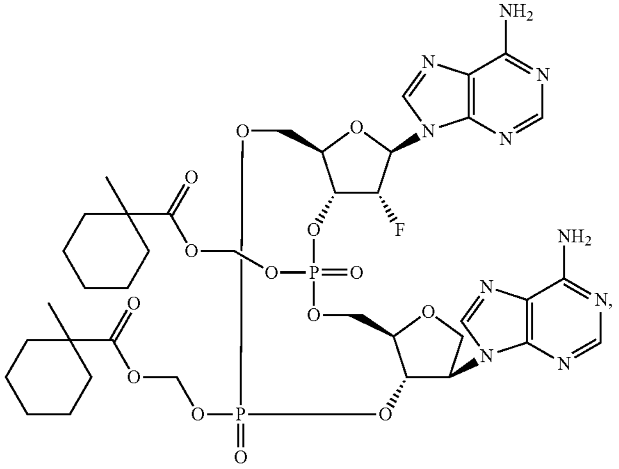
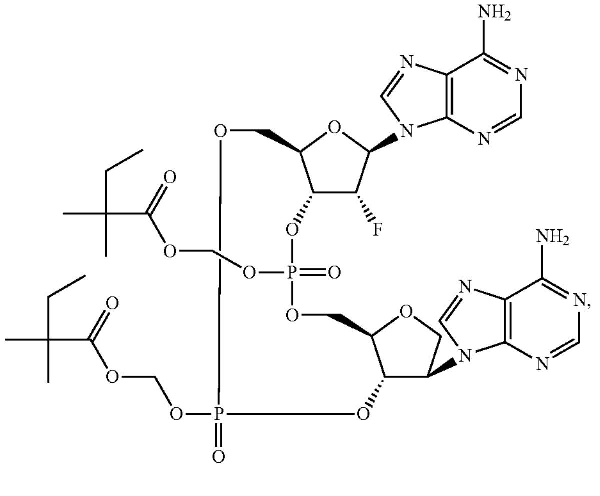
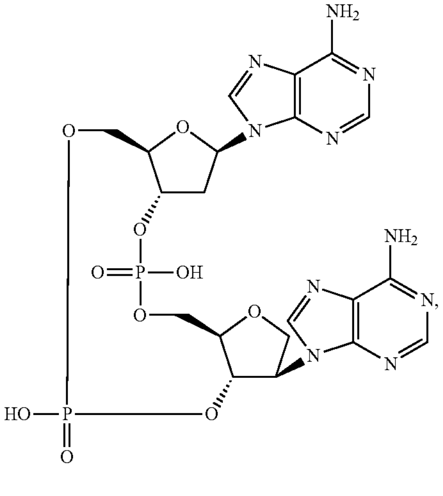

-continued
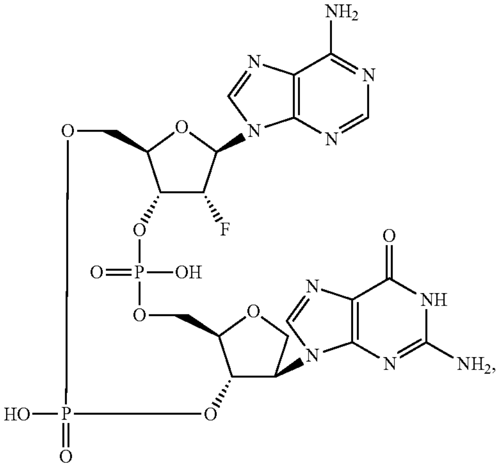
,
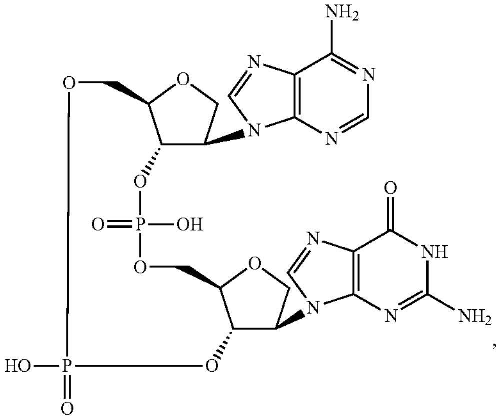
,
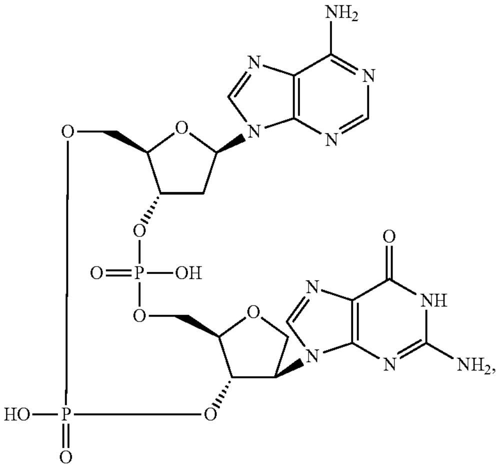
,
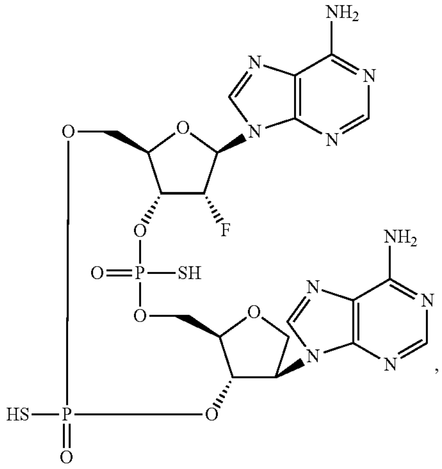
,
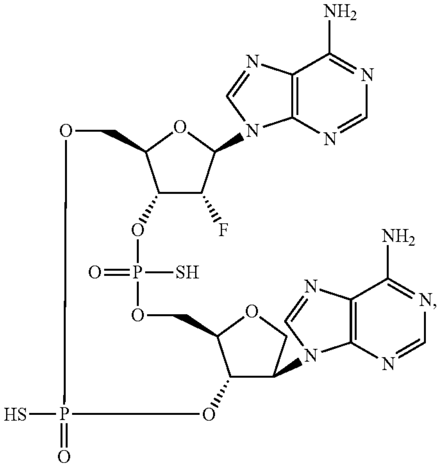
,
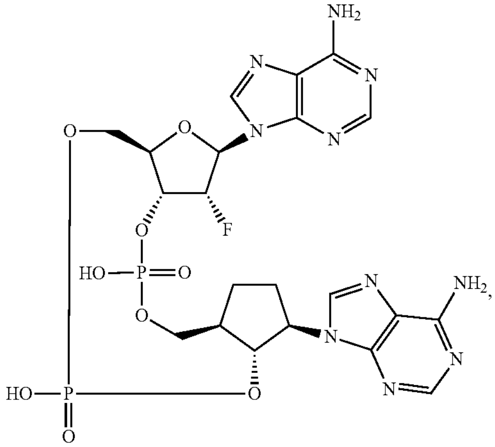
, -continued

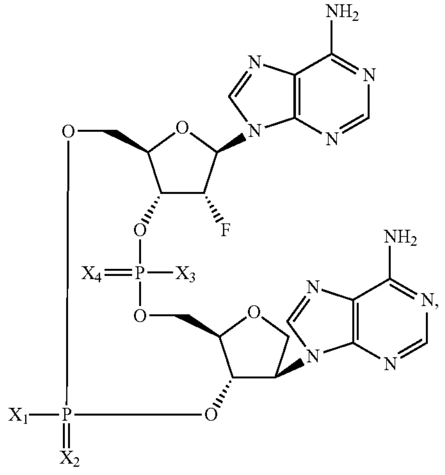

wherein $X^1$, $X^2$, $X^3$, $X^4$ are as defined in claim 1.

12. A pharmaceutical composition comprising the compound of claim 1, or an enantiomer, solvate, hydrate, or a pharmaceutically acceptable salt thereof, and a pharmaceutically acceptable carrier, excipient, and/or diluent.

13. A method of administering a medicament comprising the step of administering the compound according to claim 1 for treatment to a subject in need thereof.

14. A method of treatment comprising the step of administering the compound according to claim 1 for in vivo modulating the activity of STING adaptor protein to induce production of a type I interferon, cytokine and/or chemokine dependent on the STING adaptor protein.

15. A method of treatment comprising the step of administering the compound according to claim 1 in treating a viral infection, hepatitis B virus infection, HIV infection, a coronavirus infection (including SARS-CoV-2 infection), a flavivirus infection, allergic diseases, inflammatory diseases, hyperproliferative disease or cancer in a human or animal.

16. A method of treatment comprising the step of administering the compound according to claim 1 for in vitro modulating the activity of STING adaptor protein to induce production of a type I interferon, cytokine and/or chemokine dependent on the STING adaptor protein.

17. A method of treatment comprising the step of administering the compound according to claim 1 as a vaccine adjuvant.

* * * * *

SEQUENCE LISTING

<160> NUMBER OF SEQ ID NOS: 11

<210> SEQ ID NO 1
<211> LENGTH: 75
<212> TYPE: DNA
<213> ORGANISM: artificial
<220> FEATURE:
<223> OTHER INFORMATION: synthetic oligonucleotide

<400> SEQUENCE: 1
aaagatcttg gaaagtgaaa ccttggaaaa cgaaactgga caaagggaaa ctgcagaaac 60
tgaaacaaag cttaa 75

<210> SEQ ID NO 2
<211> LENGTH: 75
<212> TYPE: DNA
<213> ORGANISM: artificial
<220> FEATURE:
<223> OTHER INFORMATION: synthetic oligonucleotide

<400> SEQUENCE: 2
ttaagctttg tttcagtttc tgcagtttcc ctttgtccag tttcgttttc caaggtttca 60
ctttccaaga tcttt 75

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
tgcttgctca actctacgtc 20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
gtggtttgtc caaactcatc 20

<210> SEQ ID NO 5
<211> LENGTH: 31
<212> TYPE: DNA
<213> ORGANISM: artificial
<220> FEATURE:
<223> OTHER INFORMATION: primer

<400> SEQUENCE: 5
gtgggatccg ccccagctga gatctctgca g 31

<210> SEQ ID NO 6
<211> LENGTH: 38
<212> TYPE: DNA
<213> ORGANISM: artificial
<220> FEATURE:
<223> OTHER INFORMATION: primer

<400> SEQUENCE: 6
tatgcggccg cctattacac agtaacctct tccttttc 38

<210> SEQ ID NO 7
<211> LENGTH: 330
<212> TYPE: DNA
<213> ORGANISM: artificial
<220> FEATURE:
<223> OTHER INFORMATION: DNA sequence of 8-His-SUMO

<400> SEQUENCE: 7
atgtcgcatc accatcatca tcaccaccat gggatgtcgg actcagaagt caatcaagaa 60
gctaagccag aggtcaagcc agaagtcaag cctgagactc acatcaattt aaaggtgtcc 120
gatggatctt cagagatctt cttcaagatc aaaaagacca ctcctttaag aaggctgatg 180
gaagcgttcg ctaaaagaca gggtaaggaa atggactcct taagattctt gtacgacggt 240
attagaattc aagctgatca gacccctgaa gatttggaca tggaggataa cgatattatt 300
gaggctcacc gcgaacagat tggtggatcc 330

<210> SEQ ID NO 8
<211> LENGTH: 110
<212> TYPE: PRT
<213> ORGANISM: artificial
<220> FEATURE:
<223> OTHER INFORMATION: Amino acid sequence of 8-His-SUMO

<400> SEQUENCE: 8

Met Ser His His His His His His His His Gly Met Ser Asp Ser Glu
1 5 10 15

Val Asn Gln Glu Ala Lys Pro Glu Val Lys Pro Glu Val Lys Pro Glu
20 25 30

Thr His Ile Asn Leu Lys Val Ser Asp Gly Ser Ser Glu Ile Phe Phe
35 40 45

Lys Ile Lys Lys Thr Thr Pro Leu Arg Arg Leu Met Glu Ala Phe Ala
50 55 60

Lys Arg Gln Gly Lys Glu Met Asp Ser Leu Arg Phe Leu Tyr Asp Gly
65 70 75 80

Ile Arg Ile Gln Ala Asp Gln Thr Pro Glu Asp Leu Asp Met Glu Asp
85 90 95

Asn Asp Ile Ile Glu Ala His Arg Glu Gln Ile Gly Gly Ser
100 105 110

<210> SEQ ID NO 9
<211> LENGTH: 204

```
<212> TYPE: PRT
<213> ORGANISM: artificial
<220> FEATURE:
<223> OTHER INFORMATION: Amino acid sequence of truncated WT STING

<400> SEQUENCE: 9

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
            20                  25                  30

Leu Pro Glu Leu Gln Ala Arg Ile Arg Thr Tyr Asn Gln His Tyr Asn
        35                  40                  45

Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

Arg Phe Leu Asp Lys Leu Pro Gln Gln Thr Gly Asp Arg Ala Gly Ile
                85                  90                  95

Lys Asp Arg Val Tyr Ser Asn Ser Ile Tyr Glu Leu Leu Glu Asn Gly
            100                 105                 110

Gln Arg Ala Gly Thr Cys Val Leu Glu Tyr Ala Thr Pro Leu Gln Thr
        115                 120                 125

Leu Phe Ala Met Ser Gln Tyr Ser Gln Ala Gly Phe Ser Arg Glu Asp
    130                 135                 140

Arg Leu Glu Gln Ala Lys Leu Phe Cys Arg Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
            180                 185                 190

His Leu Arg Gln Glu Glu Lys Glu Glu Val Thr Val
        195                 200


<210> SEQ ID NO 10
<211> LENGTH: 204
<212> TYPE: PRT
<213> ORGANISM: artificial
<220> FEATURE:
<223> OTHER INFORMATION: Amino acid sequence of truncated AQ STING

<400> SEQUENCE: 10

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
            20                  25                  30

Leu Pro Glu Leu Gln Ala Arg Ile Arg Thr Tyr Asn Gln His Tyr Asn
        35                  40                  45

Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

Arg Phe Leu Asp Lys Leu Pro Gln Gln Thr Ala Asp Arg Ala Gly Ile
                85                  90                  95

Lys Asp Arg Val Tyr Ser Asn Ser Ile Tyr Glu Leu Leu Glu Asn Gly
            100                 105                 110

Gln Arg Ala Gly Thr Cys Val Leu Glu Tyr Ala Thr Pro Leu Gln Thr
        115                 120                 125
```

```
Leu Phe Ala Met Ser Gln Tyr Ser Gln Ala Gly Phe Ser Arg Glu Asp
    130                 135                 140

Arg Leu Glu Gln Ala Lys Leu Phe Cys Gln Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
            180                 185                 190

His Leu Arg Gln Glu Glu Lys Glu Glu Val Thr Val
        195                 200


<210> SEQ ID NO 11
<211> LENGTH: 392
<212> TYPE: PRT
<213> ORGANISM: artificial
<220> FEATURE:
<223> OTHER INFORMATION: Murine cGAS amino acid sequence including pelB
      leader and His-tag

<400> SEQUENCE: 11

Met Lys Tyr Leu Leu Pro Thr Ala Ala Ala Gly Leu Leu Leu Leu Ala
1               5                   10                  15

Ala Gln Pro Ala Met Ala Met Pro Asp Lys Leu Lys Lys Val Leu Asp
            20                  25                  30

Lys Leu Arg Leu Lys Arg Lys Asp Ile Ser Glu Ala Ala Glu Thr Val
        35                  40                  45

Asn Lys Val Val Glu Arg Leu Leu Arg Arg Met Gln Lys Arg Glu Ser
    50                  55                  60

Glu Phe Lys Gly Val Glu Gln Leu Asn Thr Gly Ser Tyr Tyr Glu His
65                  70                  75                  80

Val Lys Ile Ser Ala Pro Asn Glu Phe Asp Val Met Phe Lys Leu Glu
                85                  90                  95

Val Pro Arg Ile Glu Leu Gln Glu Tyr Tyr Glu Thr Gly Ala Phe Tyr
            100                 105                 110

Leu Val Lys Phe Lys Arg Ile Pro Arg Gly Asn Pro Leu Ser His Phe
        115                 120                 125

Leu Glu Gly Glu Val Leu Ser Ala Thr Lys Met Leu Ser Lys Phe Arg
    130                 135                 140

Lys Ile Ile Lys Glu Glu Val Lys Glu Ile Lys Asp Ile Asp Val Ser
145                 150                 155                 160

Val Glu Lys Glu Lys Pro Gly Ser Pro Ala Val Thr Leu Leu Ile Arg
                165                 170                 175

Asn Pro Glu Glu Ile Ser Val Asp Ile Ile Leu Ala Leu Glu Ser Lys
            180                 185                 190

Gly Ser Trp Pro Ile Ser Thr Lys Glu Gly Leu Pro Ile Gln Gly Trp
        195                 200                 205

Leu Gly Thr Lys Val Arg Thr Asn Leu Arg Arg Glu Pro Phe Tyr Leu
    210                 215                 220

Val Pro Lys Asn Ala Lys Asp Gly Asn Ser Phe Gln Gly Glu Thr Trp
225                 230                 235                 240

Arg Leu Ser Phe Ser His Thr Glu Lys Tyr Ile Leu Asn Asn His Gly
                245                 250                 255

Ile Glu Lys Thr Cys Cys Glu Ser Ser Gly Ala Lys Cys Cys Arg Lys
            260                 265                 270

Glu Cys Leu Lys Leu Met Lys Tyr Leu Leu Glu Gln Leu Lys Lys Glu
```

-continued

```
        275                 280                 285

Phe Gln Glu Leu Asp Ala Phe Cys Ser Tyr His Val Lys Thr Ala Ile
    290                 295                 300

Phe His Met Trp Thr Gln Asp Pro Gln Asp Ser Gln Trp Asp Pro Arg
305                 310                 315                 320

Asn Leu Ser Ser Cys Phe Asp Lys Leu Leu Ala Phe Phe Leu Glu Cys
                325                 330                 335

Leu Arg Thr Glu Lys Leu Asp His Tyr Phe Ile Pro Lys Phe Asn Leu
            340                 345                 350

Phe Ser Gln Glu Leu Ile Asp Arg Lys Ser Lys Glu Phe Leu Ser Lys
        355                 360                 365

Lys Ile Glu Tyr Glu Arg Asn Asn Gly Phe Pro Ile Phe Asp Lys Leu
    370                 375                 380

Leu Glu His His His His His His
385                 390
```